US012281065B2

(12) United States Patent
Che et al.

(10) Patent No.: US 12,281,065 B2
(45) Date of Patent: Apr. 22, 2025

(54) IRON CATALYZED HIGHLY ENANTIOSELECTIVE CIS-DIHYDROXYLATION OF QUINONES

(71) Applicants: Versitech Limited, Hong Kong (CN); Laboratory for Synthetic Chemistry and Chemical Biology Limited, Hong Kong (CN)

(72) Inventors: Chi Ming Che, Hong Kong (CN); Tingting Wang, Hong Kong (CN); Haixu Wang, Hong Kong (CN)

(73) Assignees: Versitech Limited, Hong Kong (CN); Laboratory for Synthetic Chemistry and Chemical Biology Limited, Hong Kong (CN)

( * ) Notice: Subject to any disclaimer, the term of this patent is extended or adjusted under 35 U.S.C. 154(b) by 0 days.

(21) Appl. No.: 18/155,431

(22) Filed: Jan. 17, 2023

(65) Prior Publication Data

US 2023/0227393 A1   Jul. 20, 2023

Related U.S. Application Data

(60) Provisional application No. 63/300,198, filed on Jan. 17, 2022.

(51) Int. Cl.
| | | |
|---|---|---|
| *C07C 50/04* | (2006.01) | |
| *B01J 31/40* | (2006.01) | |
| *C07C 50/12* | (2006.01) | |
| *C07C 50/30* | (2006.01) | |
| *C07C 50/34* | (2006.01) | |
| *C07C 50/36* | (2006.01) | |

(52) U.S. Cl.
CPC ............ *C07C 50/04* (2013.01); *B01J 31/4023* (2013.01); *C07C 50/12* (2013.01); *C07C 50/30* (2013.01); *C07C 50/34* (2013.01); *C07C 50/36* (2013.01)

(58) Field of Classification Search
CPC ......... C07C 50/04; C07C 50/12; C07C 50/30; C07C 50/34; C07C 50/36; B01J 31/4023
See application file for complete search history.

(56) References Cited

PUBLICATIONS

Caldwell et al. "Novel Use of a Selenoalkyne Within Untraditionally Mild Dötz Benzannulation Processes; Total Synthesis of a *Calceolaria andina* L. Natural Hydroxylated Naphthoquinone" Synlett, 2001, vol. 2001, No. 9, pp. 1428-1430.*
Zang et al. "Highly Enantioselective Iron-Catalyzed cis-Dihydroxylation of Alkenes with Hydrogen Peroxide Oxidant via an FeIII-OOH Reactive Intermediate" Angew. Chem. Int. Ed. 2016, vol. 55, pp. 10253-10257.*

Adachi, et al., "Total Syntheses of Lactonamycin and Lactonamycin Z with Late-Stage A-Ring Formation and Glycosylation", Angew Chem Int Ed, 52:2087-2091 (2013).
Adduci, et al., "Metal-Free Deoxygenation of Carbohydrates", Angew Chem Int Ed, 53:1646-1649 (2014).
Adolfsson, et al., "Recent Developments in Asymmetric Dihydroxylations" Synthesis, (11):1725-1756 (2006).
Barry, et al., "Mechanism and Catalytic Diversity of Rieske Non-Heme Iron-Dependent Oxygenases", ACS catalysis, 3:2362-2370 (2013).
Bataille, et al., "Osmium-free direct syn-dihydroxylation of alkenes", Chem Soc Rev, 40:114-128 (2011).
Bebbington, "Natural product analogues: towards a blueprint for analogue-focused synthesis", Chemical Society Reviews , 46:5059-5109 (2017).
Bhunnoo, et al., "An Asymmetric Phase-Transfer Dihydroxylation Reaction", Angewandte Chemie International Edition, 41:3479-3480 (2002).
Borrell, et al., "Greening Oxidation Catalysis: Iron Catalyzed Alkene syn-Dihydroxylation with Aqueous Hydrogen Peroxide in Green Solvents", ACS Sustainable Chemistry & Engineering, 6:8410-8416 (2018).
Borrell, et al., "Mechanistically Driven Development of an Iron Catalyst for Selective Syn-Dihydroxylation of Alkenes with Aqueous Hydrogen Peroxide", J Am Chem Soc, 139:12821-12829 (2017).
Boyd, et al., "Aromatic dioxygenases: molecular biocatalysis and applications," Current Opinion in Biotechnology, 12:564-573 (2001).
Bruijnincx, et al., "Mononuclear non-heme iron enzymes with the 2-His-1-carboxylate facial triad: recent developments in enzymology and modeling studies", Chemical Society Reviews, 37: 2716-2744 (2008).
Caldwell, et al., "Novel Use of a Selenoalkyne Within Untraditionally Mild Dötz Benzannulation Processes; Total Synthesis of a *Calceolaria andina* L. Natural Hydroxylated Naphthoquinone", Synlett, 2001(9:1428-1430 (2001).
Carless, et al., "Enantiospecific synthesis of (4S,5S,6S)-4,5,6-trihydroxycyclohex-2-enone and (+)-conduritol C from fluorobenzene via microbial oxidation", Chemical Communications, 61-62 (1991).
Chow, et al., "Practical manganese-catalysed highly enantioselective cis-dihydroxylation of electron-deficient alkenes and detection of a cis-dioxomanganese(v) intermediate by high resolution ESI-MS analysis", Chemical Communications, 47:11204-11206 (2011).
Chow, et al., "cis-Dihydroxylation of Alkenes with Oxone Catalyzed by Iron Complexes of a Macrocyclic Tetraaza Ligand and Reaction Mechanism by ESI-MS Spectrometry and DFT Calculations", Journal of the American Chemical Society , 132:13229-13239 (2010).

(Continued)

*Primary Examiner* — Matthew P Coughlin
*Assistant Examiner* — Quincy McKoy
(74) *Attorney, Agent, or Firm* — PABST PATENT GROUP LLP

(57) ABSTRACT

Methods for asymmetric cis-dihydroxylation ("AD") of quinones to produce cis-diols of quinones with high yield (i.e. a yield ≥30%) and high enantioselectivity (i.e. an enantiometric excess ≥30%) are disclosed. The method uses an iron-based catalyst, such as one or more Fe(II) complexes, as the catalyst, and can be performed under mild reaction conditions (e.g. a temperature ≤50° C. at 1 atom in open air). The method generally includes: (i) maintaining a reaction mixture at a temperature for a period of time sufficient to form a product, where the reaction mixture contains a quinone, one or more iron-based catalyst(s), and a solvent, and where the product contains a chiral cis-diol. Optionally, the method also includes adding an oxidant into the reaction mixture prior to and/or during step (i), such as a hydrogen peroxide solution.

28 Claims, 1 Drawing Sheet

(56) References Cited

PUBLICATIONS

Costas, et al., "Modeling Rieske Dioxygenases: The First Example of Iron-Catalyzed Asymmetric cis-Dihydroxylation of Olefins", Journal of the American Chemical Society, 123:6722-6723 (2001).
Cox, et al.., "Concise Synthesis of a Lactonamycin Model System by Diastereoselective Dihydroxylation of a Highly Functionalized Naphthoquinone", Organic Letters, 3:2899-2902 (2001).
Feng, et al., "Synthesis of plasmodione metabolites and 13C-enriched plasmodione as chemical tools for drug metabolism investigation", Organic & Biomolecular Chemistry, 16:2647-2665 (2018).
Fujita, et al., "Enantioselective Prévost and Woodward reactions using chiral hypervalent iodine(iii): switchover of stereochemical course of an optically active 1,3-dioxolan-2-yl cation", Chemical Communications, 47:3983-3985 (2011).
Fujiwara, et al., "Practical C-H Functionalization of Quinones with Boronic Acids", Journal of the American Chemical Society, 133:3292-3295 (2011).
Gally, et al., "Engineering Rieske Non-Heme Iron Oxygenases for the Asymmetric Dihydroxylation of Alkenes", Angewandte Chemie International Edition, 54:12952-12956 (2015).
Henderson, et al., "Studies on the Total Synthesis of Lactonamycin: Construction of Model ABCD Ring Systems", The Journal of Organic Chemistry 2006, 71:2434-2444 (2006).
Hochalter, et al., "Quantitation of a Minor Enantiomer of Phenanthrene Tetraol in Human Urine: Correlations with Levels of Overall Phenanthrene Tetraol, Benzo[a]pyrene Tetraol, and 1-Hydroxypyrene", Chem Res Toxicol, 24:262-268 (2011).
Hussein, et al., "Mechanism of Os-Catalyzed Oxidative Cyclization of 1,5-Dienes", The Journal of Organic Chemistry, 84:15173-15183 (2019).
Jones, et al., "Topical nonsteroidal antipsoriatic agents. 1. 1,2,3,4-Tetraoxygenated naphthalene derivatives", Journal of Medicinal Chemistry, 29:1504-1511 (1986).
Kadota, et al., "A New Convergent Route to Conduritols A-F from a Common Chiral Building Block", Organic Letters, 3:1769-1772 (2001).
Kolb, et al., "Catalytic Asymmetric Dihydroxylation", Chemical Reviews, 94:2483 2547 (1994).
Lowe, et al., "Boron-Catalyzed Site-Selective Reduction of Carbohydrate Derivatives with Catecholborane", ACS Catalysis, 8: 8192-8198 (2018).
Maeda, et al., "Oxygenated Cyclohexene Derivatives and Other Constituents from the Roots of Monanthotaxis trichocarpa", J Nat Prod, 83:210-215 (2020).
Mechsner, et al., "Enantioselective total synthesis of altersolanol A and N", Bioorganic & Medicinal Chemistry 2019, 27:2991-2997 (2019).
Milic, et al., "Synthesis and antiproliferative activity of A-ring aromatised and conduritol-like steroidal compounds", Steroids, 70:922-932 (2005).
Moelands, et al., "Bioinspired Nonheme Iron Complexes Derived from an Extended Series of N,N,O-Ligated BAIP Ligands", Inorganic Chemistry, 52:7394-7410 (2013).
Neisius, et al., "Diastereoselective Ru-Catalyzed Cross-Metathesis-Dihydroxylation Sequence. An Efficient Approach toward Enantiomerically Enriched syn-Diols", The Journal of Organic Chemistry, 73:3218-3227 (2008).
Noe, et al., "Asymmetric dihydroxylation of alkenes", Organic Reactions, 109-625 (2005).
Novikov, et al., "Oxidation of 7-ethyl-2,3,5,6,8-pentahydroxy-1,4-naphthoquinone (echinochrome A) by atmospheric oxygen 1. Structure of dehydroechinochrome", Russian Chemical Bulletin, 67:282-290 (2018).
Oldenburg, et al., "Iron-Catalyzed Olefin cis-Dihydroxylation Using a Bio-Inspired N,N, OLigand", Journal of the American Chemical Society, 127:15672-15673 (2005).
Olivo, et al., "Oxidation of alkane and alkene moieties with biologically inspired nonheme iron catalysts and hydrogen peroxide: from free radicals to stereoselective transformations", Journal of Biological Inorganic Chemistry22:425-452 (2017,).
Ottenbacher, et al., "Recent advances in catalytic asymmetric dihydroxylation of olefins", Russian Chemical Reviews, 88:1094-1103 (2019).
Patti, et al., "Enantioselective Synthesis of (-)- and (+)-Conduritol F via Enzymatic Asymmetrization of cis-Cyclohexa-3,5-diene-1,2-diol", The Journal of Organic Chemistry, 61, 6458-6461 (1996).
Prat, et al., "Fe(PyTACN)-Catalyzed cis-Dihydroxylation of Olefins with Hydrogen Peroxide", Advanced Synthesis & Catalysis, 355:947-956 (2013).
Prat, et al., "Assessing the Impact of Electronic and Steric Tuning of the Ligand in the Spin State and Catalytic Oxidation Ability of the FeII(Pytacn) Family of Complexes", Inorganic Chemistry, 52:9229-9244 (2013).
Rodo, et al., "A Platform of Regioselective Methodologies to Access Polysubstituted 2-Methyl-1,4-naphthoquinone Derivatives: Scope and Limitations", European Journal of Organic Chemistry, 2016:1982-1993 (2016).
Sakai, et al., "Pestynol, an Antifungal Compound Discovered Using a *Saccharomyces cerevisiae* 12geneΔ0HSR-iERG6-Based Assay," J Nat Prod, 81:1604-1609 (2018).
Sharpless, et al., "The osmium-catalyzed asymmetric dihydroxylation: a new ligand class and a process improvement", The Journal of Organic Chemistry, 57:2768-2771 (1992).
Siu, et al., "Total Synthesis of Lactonamycinone", Angew Chem Int Ed, 42, 5629-5634 (2003).
Southgate, et al., "Dearomative dihydroxylation with arenophiles", Nat Chem, 8:922-928 (2016).
Sugimoto, et al., "An Osmium(III)/Osmium(V) Redox Couple Generating OsV(O)(OH) Center for cis-1,2-Dihydroxylation of Alkenes with H2O2: Os Complex with a Nitrogen-Based Tetradentate Ligand", Journal of the American Chemical Society, 134:19270-19280 (2012).
Suzuki, et al., "Iron-Catalyzed Asymmetric Olefin cis-Dihydroxylation with 97 % Enantiomeric Excess", Angew Chem Int Ed, 47:1887-1889 (2008).
Talsi, et al., "Chemo- and stereoselective Csingle bondH oxidations and epoxidations/cis-dihydroxylations with H2O2, catalyzed by non-heme iron and manganese complexes", Coordination Chemistry Reviews, 256:1418-1434 (2012).
Toribatake, et al., "Asymmetric Diboration of Terminal Alkenes with a Rhodium Catalyst and Subsequent Oxidation: Enantioselective Synthesis of Optically Active 1,2-Diols", Angew Chem Int Ed, 52:11011-11015 (2013).
Veldkamp, et al., "Mechanism of the Enantioselective Dihydroxylation of Olefins by OsO4 in the Presence of Chiral Bases", JACS, 116:4937-4946 (1994).
Viault, et al., "Synthesis of a Focused Chemical Library Based on Derivatives of Embelin, a Natural Product with Proapoptotic and Anticancer Properties", European Journal of Organic Chemistry, 2011:1233-1241 (2011).
Wang, et al., "Facile Synthesis of Enantiopure Sugar Alcohols: Asymmetric Hydrogenation and Dynamic Kinetic Resolution Combined", Angewandte Chemie International Edition, 59:18166-18171 (2020).
Wang, et al., "Enantioselective Oxidation of Alkenes with Potassium Permanganate Catalyzed by Chiral Dicationic Bisguanidinium", J Am Chem Soc, 137:10677-10682 (2015).
Watanabe, et al., "Synthetic Studies on Lactonamycins: Synthesis of the Model BCDEF Aglycon", J Org Chem, 75:5573-5579 (2010).
Wei, et al., "Transforming Flask Reaction into Cell-Based Synthesis: Production of Polyhydroxylated Molecules via Engineered *Escherichia coli*", ACS Catalysis, 5:4060-4065 (2015).
Wei, et al., "Iron-Catalyzed Highly Enantioselective cis-Dihydroxylation of Trisubstituted Alkenes with Aqueous H2O2", Angewandte Chemie International Edition, 59:16561-16571 (2020).
Wolfe, et al., "Hydrogen Peroxide-coupled cis-Diol Formation Catalyzed by Naphthalene 1,2-Dioxygenase", Journal of Biological Chemistry, 278:829-835 (2003).
Zang, et al., "Highly Enantioselective Iron-Catalyzed cis-Dihydroxylation of Alkenes with Hydrogen Peroxide Oxidant via an

(56) References Cited

PUBLICATIONS

FeIII-OOH Reactive Intermediate", Angewandte Chemie International Edition, 55:10253-10257 (2016).

* cited by examiner

IRON CATALYZED HIGHLY ENANTIOSELECTIVE CIS-DIHYDROXYLATION OF QUINONES

CROSS REFERENCE TO RELATED APPLICATION

This application claims priority to U.S. Provisional Patent Application No. 63/300,198 filed Jan. 17, 2022, the disclosure of which is incorporated herein by reference.

FIELD OF THE INVENTION

This invention is generally in the field of asymmetric hydroxylation of quinones using iron-based catalysts.

BACKGROUND OF THE INVENTION

Catalytic asymmetric cis-dihydroxylation (AD) reactions of alkenes is an important synthetic methodology that gives direct access to chiral cis-diol structures that are prevalent in natural products and bioactive compounds (Kolb, et al., *Chemical Reviews* 1994, 94, 2483-2547; Bataille and Donohoe, *Chem Soc Rev* 2011, 40, 114-128; Bebbington, *Chemical Society Reviews* 2017, 46, 5059-5109; Ottenbacher, et al., *Russian Chemical Reviews* 2019, 88, 1094-1103).

Currently, AD reactions are mainly performed with osmium-based catalysts such as the commercial products AD-mix-α/β developed by Sharpless and co-workers (Kolb, et al., *Chemical Reviews* 1994, 94, 2483-2547; Noe, et al., *Organic Reactions* 2005, 109-625; Adolfsson and Zaitsev, *Synthesis* 2006, 2006, 1725-1756; Sugimoto, et al., *Journal of the American Chemical Society* 2012, 134, 19270-19280). However, the high toxicity of Os catalysts, their high cost, and poor atom economy, raise concerns in pharmaceutical industry and other practical synthetic applications. Further, given the electrophilic nature of the Os-based catalysts (Veldkamp and Frenking, *Journal of the American Chemical Society* 1994, 116, 4937-4946; Hussein, et al., *The Journal of Organic Chemistry* 2019, 84, 15173-15183), AD reactions of electron-deficient alkenes remain underdeveloped, including the dihydroxylation reactions of quinones, which are key steps in the total synthesis of many useful compounds (Cox and Danishefsky, *Organic Letters* 2001, 3, 2899-2902; Siu, et al., *Angewandte Chemie International Edition* 2003, 42, 5629-5634; Henderson, et al., *The Journal of Organic Chemistry* 2006, 71, 2434-2444; Kamo, et al., *Angewandte Chemie International Edition* 2016, 55, 10317-10320). Organic quinones are highly electron-deficient alkenes and planar in structure, which make the asymmetric catalysis a great challenge. Up to now, there has been no report on the asymmetric dihydroxylation of quinones using osmium (Os) catalysts.

There are a few Os-free alkene cis-dihydroxylation and related protocols reported in the literature. However, it is still challenging for these methods to replace the current Sharpless dihydroxylation reaction, due to their limitations in substrate scope, product yield, stereoselectivity (enantioselectivity and cis-/trans-diol selectivity), and/or chemoselectivity (diol/epoxide selectivity) (Bhunnoo, et al., *Angewandte Chemie International Edition* 2002, 41, 3479-3480; Neisius and Plietker, *The Journal of Organic Chemistry* 2008, 73, 3218-3227; Chow, et al., *Chemical Communications* 2011, 47, 11204-11206; Fujita, et al., *Chemical Communications* 2011, 47, 3983-3985; Toribatake and Nishiyama, *Angew Chem Int Ed* 2013, 52, 11011-11015; Wang, et al., *Journal of the American Chemical Society* 2015, 137, 10677-10682; Wang, et al., *J Am Chem Soc* 2015, 137, 10677-10682). In particular, AD reactions of quinones remain elusive in the literature.

There remains a need to develop improved methods for asymmetric cis-dihydroxylation of quinones.

Therefore, it is the object of the present invention to provide methods for asymmetric cis-dihydroxylation of quinones.

It is a further object of the present invention to provide iron-based catalysts for catalyzing the asymmetric cis-dihydroxylation of quinones.

It is a further object of the present invention to provide cis-diol products formed from asymmetric cis-dihydroxylation of quinones.

SUMMARY OF THE INVENTION

Methods for asymmetric cis-dihydroxylation (AD) of quinones to produce cis-diols of quinones with high yield (i.e. a yield ≥30%) and high enantioselectivity (i.e. an enantiometric excess ≥30%), iron complexes for catalyzing the AD of quinones have been developed. The cis-diols of quinones produced from the methods described herein are powerful building blocks for the bioactive natural products and active pharmaceutical ingredients ("APIs"). The methods described herein use an iron-based catalyst, such as one or more Fe(II) complexes, as the catalyst, and can be performed under mild reaction conditions (e.g. a temperature ≤50° C. at 1 atm in open air). The methods described herein have at least the following advantages: (1) cis-diols of quinones can be produced with high yield and high enantioselectivity; (2) the use of biocompatible iron-based catalysts is environmentally friendly and cost efficient; (3) the waste generated from the reaction is non-toxic; and (4) the reactions can be performed under ambient conditions, such as at room temperature and 1 atm.

The method generally includes: (i) maintaining a reaction mixture at a temperature for a period of time sufficient to form a product, where the reaction mixture contains a quinone, one or more iron-based catalyst(s), and a solvent, and where the product contains a cis-diol. The solvent for forming the reaction mixture can be an alcohol, optionally a $C_1$-$C_6$ alcohol, or acetonitrile, or a combination thereof. In some forms, the reaction mixture can be maintained at room temperature for a period of time in a range from about 20 minutes to about 3 hours, from about 30 minutes to about 2 hours, or from about 30 minutes to 1 hour to form the product containing the cis-diol.

Optionally, the method can also include adding an oxidant (e.g. a hydrogen peroxide solution) into the reaction mixture prior to and/or during step (i); adding one or more additive(s) into the reaction mixture prior to and/or during step (i); stirring the reaction mixture prior to and/or during step (i); and/or purifying the product, optionally by column chromatography, subsequent to step (i). When an oxidant is added in the reaction mixture, the total mole amount of the oxidant can be in a range from about 1-time to about 10-time, from about 1.5-time to about 6-time, or from about 2-time to about 5-time of the total mole amount of the quinone.

In some forms, the quinone can have a structure of:

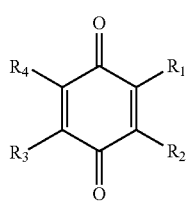

Formula I where: (a) $R_1$-$R_4$ can be independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (b) the substituents can be independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms, at least one of $R_1$-$R_4$, at least two of $R_1$-$R_4$, or at least three of $R_1$-$R_4$ can be an or are electron-donating group(s). In some forms, at least one of $R_1$-$R_4$ can be hydrogen. In some forms, $R_1$-$R_4$ can be independently a hydrogen, a substituted or unsubstituted alkyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic group, a substituted or unsubstituted aralkyl, an alkoxyl, or a carbonyl, or two neighboring R groups form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

In some forms, $R_1$-$R_4$ can be independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

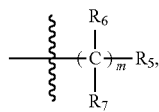

$R_5$ can be a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ can be independently a hydrogen or a substituted or unsubstituted alkyl, and m can be an integer from 1 to 10, or two neighboring R groups can form a substituted or unsubstituted aryl or a substituted or unsubstituted polyaryl.

In some forms, $R_1$-$R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

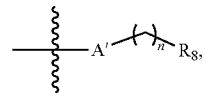

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, or two neighboring R groups can form a substituted or unsubstituted aryl or a substituted or unsubstituted polyaryl.

In some forms, the quinone can have a structure of:

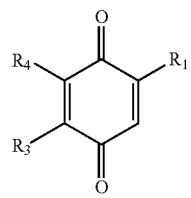

Formula III wherein $R_1$, $R_3$, and $R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

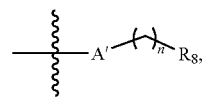

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, or $R_3$ and $R_4$ together can form a substituted or unsubstituted aryl or a substituted or unsubstituted polyaryl.

In some forms, the quinone can have a structure of:

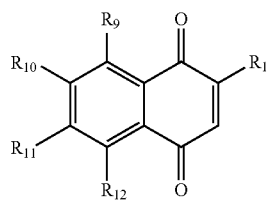

Formula IV where: (a) $R_1$ can be a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

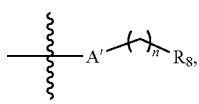

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8; and (b) $R_9$-$R_{12}$ can be independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

In some forms, $R_9$-$R_{12}$ can be independently a hydrogen, a halide, a hydroxyl, an aroxy, an alkoxyl, or $R_{11}$ and $R_{12}$ together can form a substituted or unsubstituted cycloalkenyl, a substituted or unsubstituted polycycloalkenyl, a substituted or unsubstituted aryl or a substituted or unsubstituted polyaryl.

In some forms, the quinone can have a structure of:

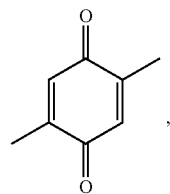

1a

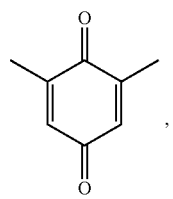

1b

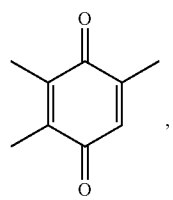

1c

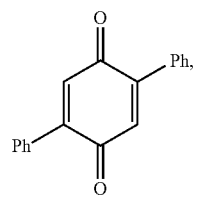

1d

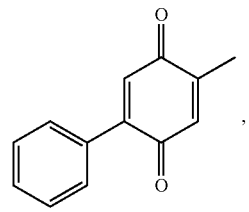

1e

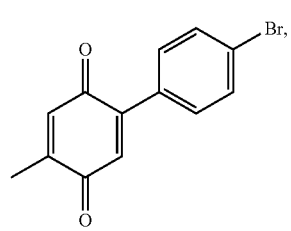

1f

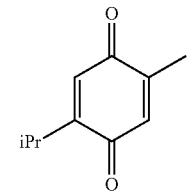

1g

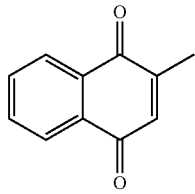

1h

7
-continued
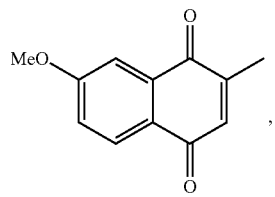
1i
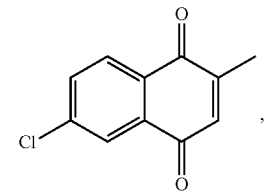
1j
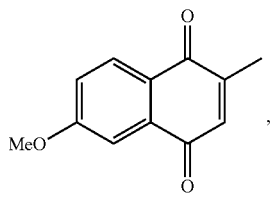
1k
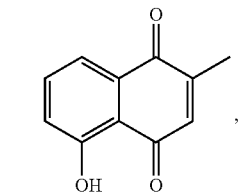
1l
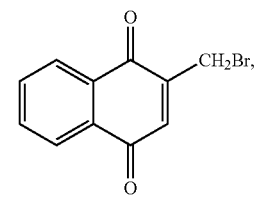
1m
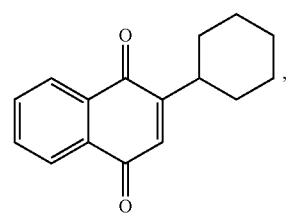
1n
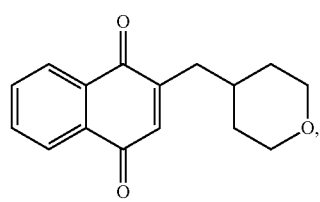
1o
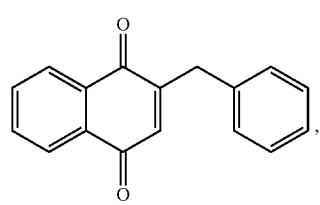
1p
8
-continued
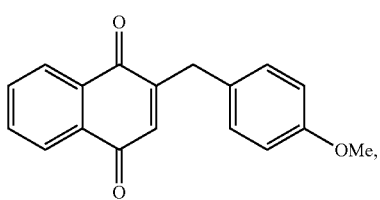
1q
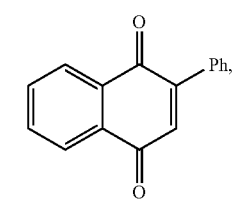
1r
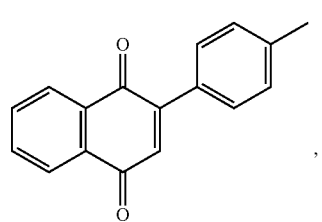
1s
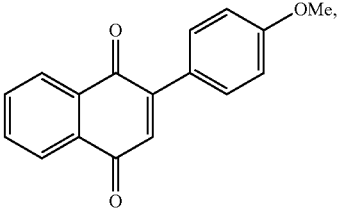
1t
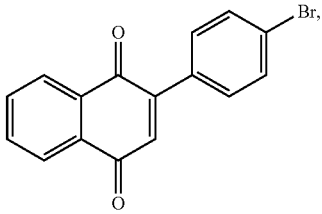
1u
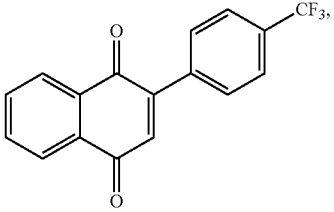
1v
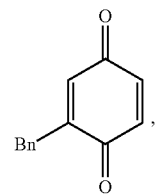
3b 3c 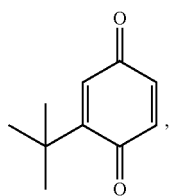

3d 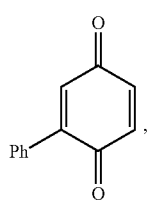

3e 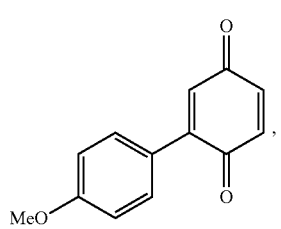

3f 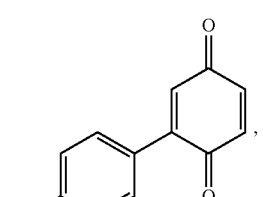

3g 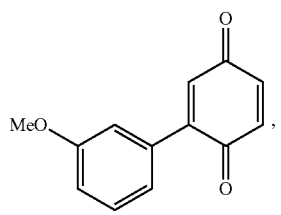

3h 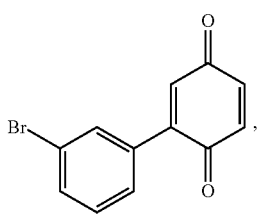

3i 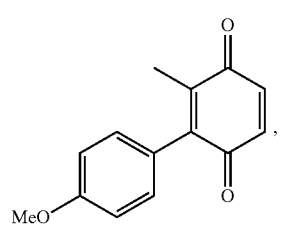

3j 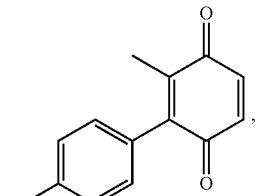

3k 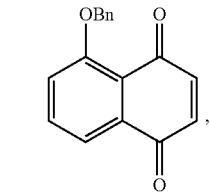

3l 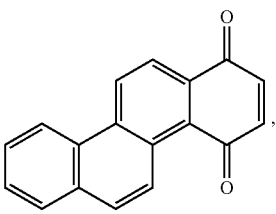

3m 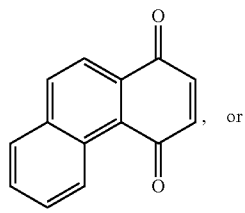, or

3n 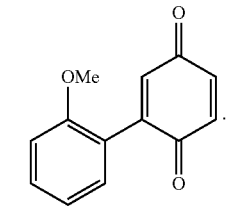.

In some forms, the cis-diol can have a structure of:

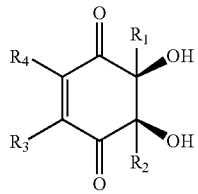

Formula V where: (a) $R_1$-$R_4$ can be independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (b) the substituents can be independently a substituted or unsubstituted alkyl (such as a haloalkyl, e.g., —CF$_3$), a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms, $R_1$-$R_4$ can be independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

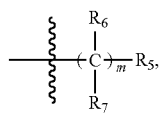

$R_5$ can be a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ can be independently a hydrogen or a substituted or unsubstituted alkyl, and m can be an integer from 1 to 10, or two neighboring R groups can form a substituted or unsubstituted aryl or a substituted or unsubstituted polyaryl.

In some forms, $R_1$-$R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

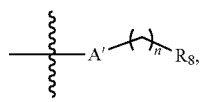

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, or two neighboring R groups can form a substituted or unsubstituted aryl or a substituted or unsubstituted polyaryl.

In some forms, the cis-diol can have a structure of:

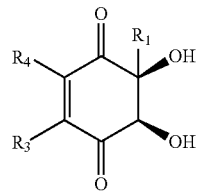

Formula VII where $R_1$, $R_3$, and $R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

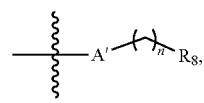

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, or $R_3$ and $R_4$ together can form a substituted or unsubstituted aryl or a substituted or unsubstituted polyaryl.

In some forms, the cis-diol can have a structure of:

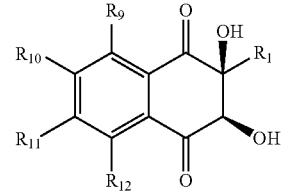

Formula VIII where: (a) $R_1$ can be a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

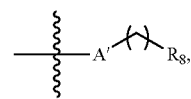

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8; and (b) $R_9$-$R_{12}$ can be independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

In some forms, $R_9$-$R_{12}$ can be independently a hydrogen, a halide, a hydroxyl, an aroxy, an alkoxyl, or $R_{11}$ and $R_{12}$ together with the carbon atoms to which they are attached can form a substituted or unsubstituted cycloalkenyl, a substituted or unsubstituted polycycloalkenyl, a substituted or unsubstituted aryl or a substituted or unsubstituted polyaryl.

In some forms, the cis-diol can have a structure of:

15
-continued
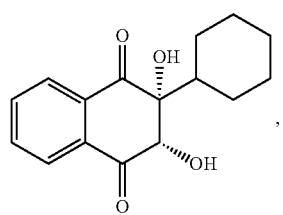
2n
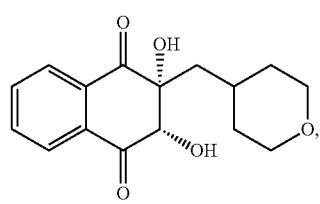
2o
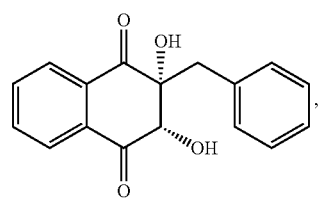
2p
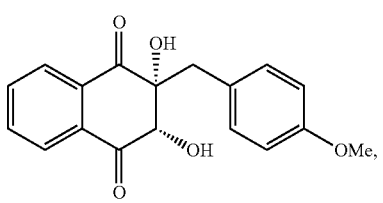
2q
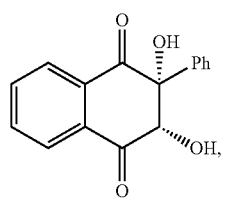
2r
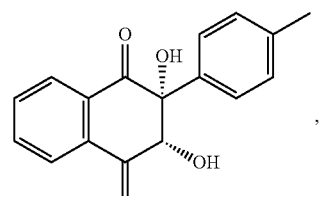
2s
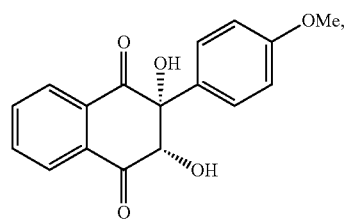
2t
16
-continued
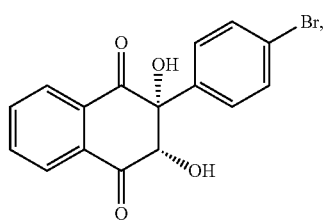
2u
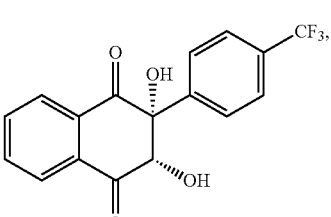
2v
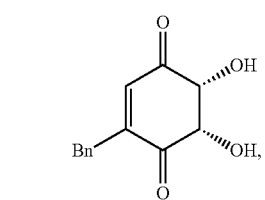
4b
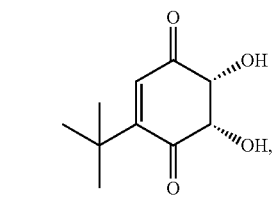
4c
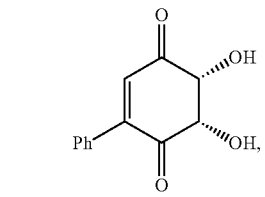
4d
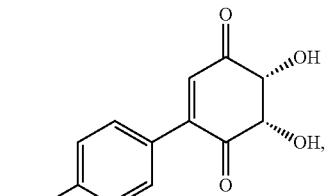
4e
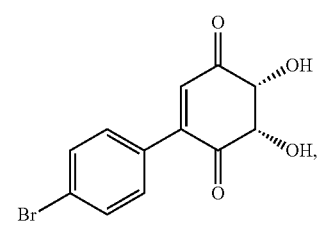
4f -continued 4g 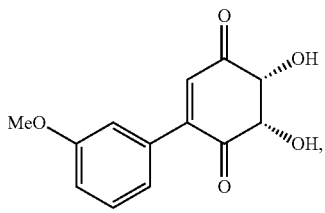

4h 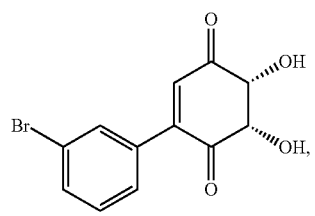

4i 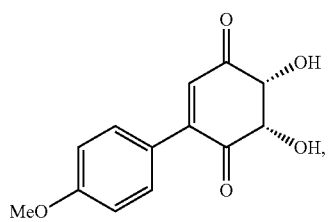

4j 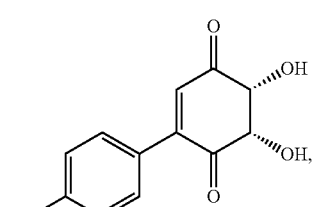

4k 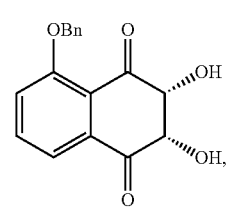

4l 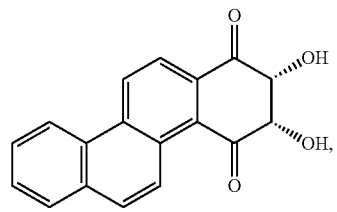

4m 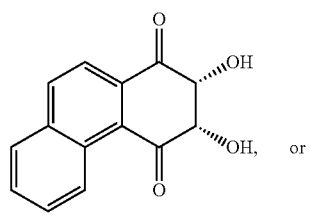 or

-continued

4n 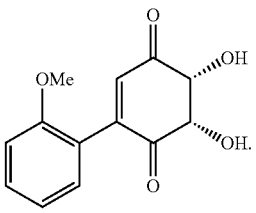

In some forms, each of the one or more iron-based catalyst(s) can have a structure of:

Formula IX

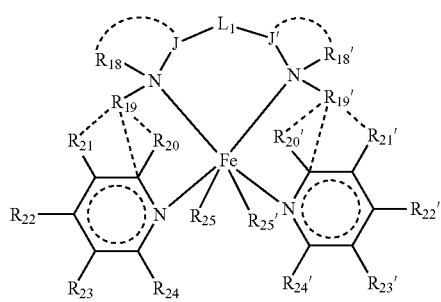

where: (a) J and J' can be independently a bond (single, double, or triple), a substituted or unsubstituted alkyl, a substituted or unsubstituted alkenyl, a substituted or unsubstituted cyclic group, a substituted or unsubstituted aryl, or a substituted or unsubstituted polyaryl; (b) $L_1$ can be a bond or

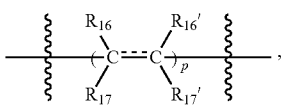

$R_{16}$, $R_{16}'$, $R_{17}$, and $R_{17}'$ can be independently a hydrogen, a substituted or unsubstituted alkyl, a substituted or unsubstituted alkenyl, a substituted or unsubstituted aryl, a substituted or unsubstituted polyaryl, or a substituted or unsubstituted cyclic group, or $R_{16}$ and $R_{16}'$ together and/or $R_{17}$ and $R_{17}'$ together, with the carbon atoms to which they are attached, can form a substituted or unsubstituted aryl, a substituted or unsubstituted polyaryl, or a substituted or unsubstituted cyclic group, and p can be an integer from 1 to 10; (c) $R_{18}$-$R_{24}$ and $R_{18}'$-$R_{24}'$ can be independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl; (d) $R_{25}$ and $R_{25}'$ can be independently a leaving group; (e)—can be absent or a bond (single, double, or triple); and (f) the substituents can be independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms, $R_{19}$, $R_{20}$, and $R_{21}$ together and/or $R_{19}'$, $R_{20}'$, and $R_{21}'$ together, with the carbon atoms to which they are attached, can form a substituted or unsubstituted aryl, a substituted or unsubstituted polyaryl, or a substituted or unsubstituted cyclic group.

In some forms, each of the one or more iron-based catalyst(s) can have a structure of Formula X, XI, or XIII:

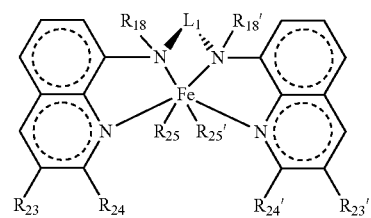
Formula X

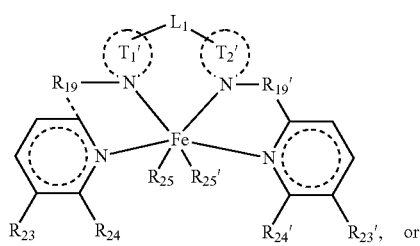
Formula XI

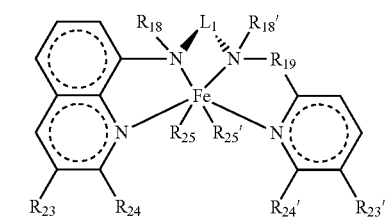
Formula XIII

Where: (a) $L_1$ can be a bond or

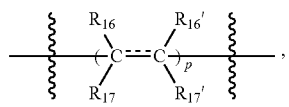

$R_{16}$, $R_{16}'$, $R_{17}$, and $R_{17}'$ can be independently a hydrogen, a substituted or unsubstituted alkyl, a substituted or unsubstituted alkenyl, a substituted or unsubstituted aryl, a substituted or unsubstituted polyaryl, or a substituted or unsubstituted cyclic group, or $R_{16}$ and $R_{16}'$ together and/or $R_{17}$ and $R_{17}'$ together, with the carbon atoms to which they are attached, can form a substituted or unsubstituted aryl, a substituted or unsubstituted polyaryl, or a substituted or unsubstituted cyclic group, and p can be an integer from 1 to 10; (b) $T_1'$ and $T_2'$ can be independently a substituted or unsubstituted heteroaryl, a substituted or unsubstituted heteropolyaryl, or a substituted or unsubstituted heterocyclic group; (c) $R_{18}$, $R_{19}$, $R_{23}$, $R_{24}$, $R_{18}'$, $R_{19}'$, $R_{23}'$, and $R_{24}'$ can be independently a hydrogen, a substituted or unsubstituted alkyl, a substituted or unsubstituted alkenyl, or a substituted or unsubstituted aryl; (d) $R_{25}$ and $R_{25}'$ can be independently a leaving group; and (e) the substituents can be independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms, $L_1$ can be

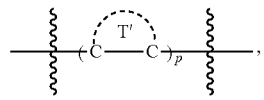

each occurrence of T' can be a substituted or unsubstituted monocyclic group or a substituted or unsubstituted polycyclic group and p can be an integer from 1 to 3, such as 1. In some forms, $R_{25}$ and $R_{25}'$ can be independently a triflate, a tosylate, a mesylate, a halide, a nitrate, a phosphate, a thioether, an amino, a carboxylate, a phenoxide, an alkoxyl, or an amido. In some forms, $R_{25}$ and $R_{25}'$ can be triflate.

In some forms, the Fe(II) complex for catalyzing the AD of quinones can have the structure of Formula XII, XIV, or XV.

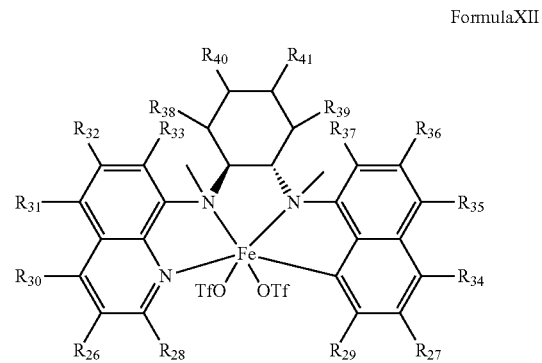
Formula XII

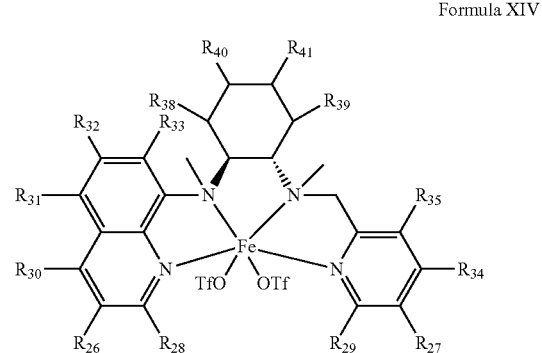
Formula XIV

Formula XV

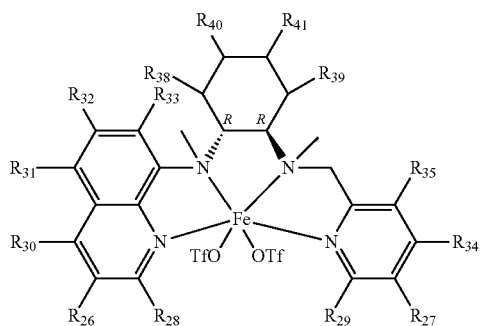

where: (a) $R_{26}$ and $R_{27}$ can be independently hydrogen, a substituted or unsubstituted cyclic group, a substituted or unsubstituted aryl, or a substituted or unsubstituted polyaryl; (b) $R_{28}$-$R_{41}$ can be independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl; and (c) the substituents can be independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof. In some forms of Formula XII, $R_{26}$ and $R_{27}$ are not hydrogen.

In some forms, for any of Formulae XII, XIV, and XV, $R_{26}$ and $R_{27}$ can be independently hydrogen, a substituted or unsubstituted aryl, or a substituted or unsubstituted polyaryl; (b) $R_{28}$-$R_{41}$ can be independently a hydrogen, a substituted or unsubstituted alkyl, or a substituted or unsubstituted alkenyl; and (c) the substituents can be independently a substituted or unsubstituted alkyl, a substituted or unsubstituted alkenyl, or a substituted or unsubstituted alkynyl, or a combination thereof. In some forms, $R_{26}$ and $R_{27}$ of Formula XII are not hydrogen.

In some forms, for any of Formulae XII, XIV, and XV, (a) $R_{26}$ and $R_{27}$ can be independently hydrogen or a substituted or unsubstituted aryl; (b) $R_{28}$-$R_{41}$ can be independently a hydrogen, an unsubstituted alkyl, or an unsubstituted alkenyl; and (c) the substituents can be independently an unsubstituted alkyl, an unsubstituted alkenyl, an unsubstituted alkynyl, or a combination thereof. In some forms, $R_{26}$ and $R_{27}$ of Formula XII are not hydrogen.

In some forms, for any of Formulae XII, XIV, and XV, (a) $R_{26}$ and $R_{27}$ can be independently hydrogen or an unsubstituted aryl and (b) $R_{28}$-$R_{41}$ can be independently a hydrogen, an unsubstituted alkyl, or an unsubstituted alkenyl. In some forms, $R_{26}$ and $R_{27}$ of Formula XII are not hydrogen.

In some forms, for any of Formulae XIV and XV, (a) $R_{26}$ and $R_{27}$ can be hydrogen, (b) $R_{28}$ and $R_{29}$ can be independently a substituted or unsubstituted alkyl, such as an unsubstituted alkyl, and (c) $R_{30}$-$R_{40}$ can be hydrogen.

In some forms, the catalyst can have a structure of:

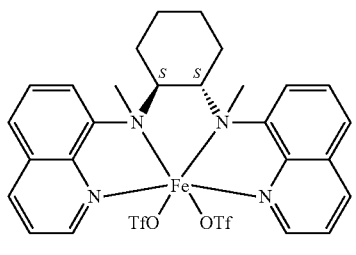

$Fe^{II}(L1)(OTf)_2$

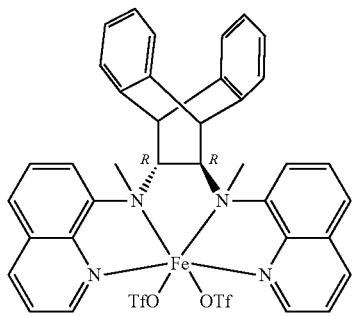

$[Fe^{II}(L2)(OTf)_2]$

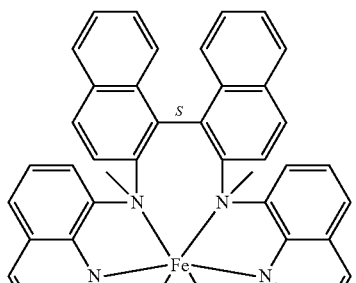

$Fe^{II}(L3)(OTf)_2$

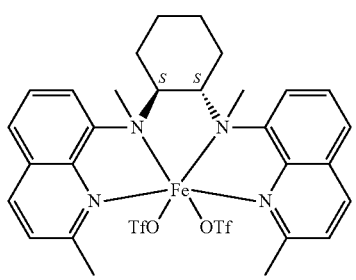

$Fe^{II}(L4)(OTf)_2$

-continued

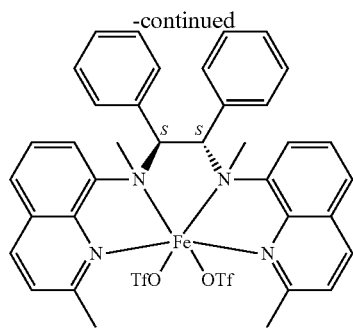

Fe^II(L5)(OTf)_2

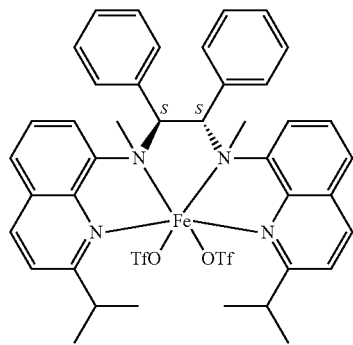

Fe^II(L6)(OTf)_2

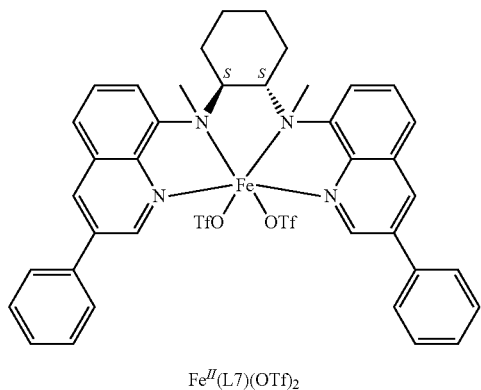

Fe^II(L7)(OTf)_2

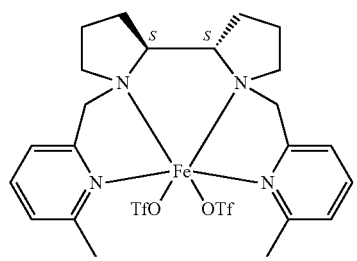

Fe^II(L8)(OTf)_2

-continued

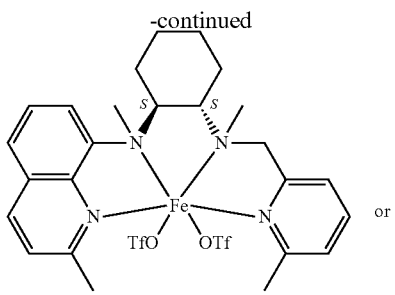

Fe^II(L9)(OTf)_2 or

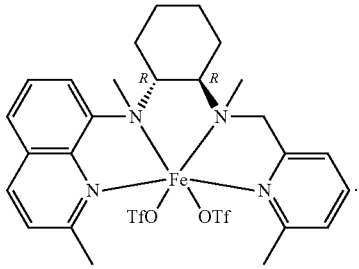

Fe^II(L9-R)(OTf)_2.

Generally, the total amount of the one or more iron-based catalyst(s) in the reaction mixture can be up to 10 mol %, up to 5 mol %, up to 3 mol %, at least 0.1 mol %, at least 0.5 mol %, in a range from about 0.1 mol % to about 10 mol %, from about 0.1 mol % to about 5 mol %, from about 0.1 mol % to about 3 mol %, from about 0.5 mol % to about 10 mol %, from about 0.5 mol % to about 5 mol %, from about 0.5 mol % to about 3 mol %, from about 1 mol % to about 10 mol %, from about 1 mol % to about 5 mol %, or from about 0.5 mol % to about 2 mol %.

Generally, the cis-diol produced from AD of a quinone using the methods described herein can have a yield of at least 30%, at least 40%, at least 50%, in a range from about 30% to about 99%, from about 40% to about 99%, from about 50% to about 99%, from about 60% to about 99%, from about 70% to about 99%, or from about 80% to about 99%, and/or an enantiometric excess of at least 30%, at least 40%, at least 50%, at least 60%, up to 100%, in a range from about 35% to 100%, from about 60% to 100%, from about 70% to 100%, from about 80% to 100%, from about 90% to 100%, or from about 95% to 100%, as determined by chiral HPLC.

Typically, the yield and enantioselectivity of cis-diols of quinones produced using the methods described herein are higher compared to Os-based catalysts (such as $OsO_4$ and AD-mix-β). In some forms, the cis-diol produced from AD of a quinone using the methods described herein can have a yield and/or an enantioselectivity that are/is higher than the yield and/or enantioselectivity of the same cis-diol produced from the same reaction (e.g. using the same quinones to form the same cis-diol products), using the same loading or a higher loading of $OsO_4$ and/or AD-mix-α/β compared to the loading of the iron-based catalyst disclosed herein.

For example, the cis-diol of quinones produced using the methods described herein has a yield that is at least 4-time, at least 4.5-time, at least 5-time, or at least 5.5-time higher than the yield of the same cis-diol, and/or an enantiometric excess that is at least 3-time, at least 3.5-time, at least 4-time, at least 5-time, or at least 5.5-time higher than the enantiometric excess of the same cis-diol, formed from the same reaction, using the same amount or a higher amount of $OsO_4$ or AD-mix-α/β compared to the total amount of the iron-based catalyst.

DETAILED DESCRIPTION OF THE INVENTION

I. Definitions

Figure 1A:
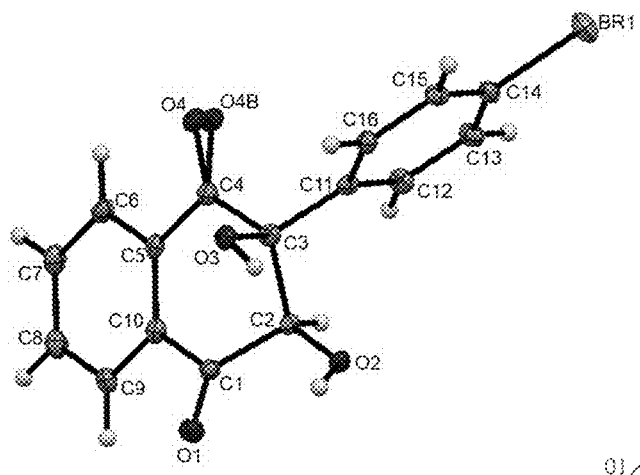
FIGS. 1A-1C are schematic diagrams showing the absolute configuration of product 2u (FIG. 1A), product 2m (FIG. 1B), and exemplary catalyst $Fe^{II}(L9)(OTf)_2$ (FIG. 1C) determined by X-ray crystallography.

It is to be understood that the disclosed compounds, compositions, and methods are not limited to specific synthetic methods, specific analytical techniques, or to particular reagents unless otherwise specified, and, as such, may vary. It is also to be understood that the terminology used herein is for the purpose of describing particular forms and embodiments only and is not intended to be limiting.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, an amino acid. Such a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, and an amino acid can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl groups, branched-chain alkyl, and cycloalkyl (alicyclic). In some forms, a straight chain or branched chain alkyl has 30 or fewer carbon atoms in its backbone (e.g., $C_1$-$C_{30}$ for straight chains, $C_3$-$C_{30}$ for branched chains), 20 or fewer, 15 or fewer, or 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Likewise, a cycloalkyl is a non-aromatic carbon-based ring composed of at least three carbon atoms, such as a nonaromatic monocyclic or nonaromatic polycyclic ring containing 3-30 carbon atoms, 3-20 carbon atoms, or 3-10 carbon atoms in their ring structure, and have 5, 6 or 7 carbons in the ring structure. Cycloalkyls containing a polycyclic ring system can have two or more non-aromatic rings in which two or more carbons are common to two adjoining rings (i.e., "fused cycloalkyl rings"). Examples of cycloalkyl groups include, but are not limited to, cyclopropyl, cyclobutyl, cyclopentyl, cyclohexyl, cycloheptyl, cyclooctanyl, etc.

The term "alkyl" as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents can be any substituents described above, e.g., halogen (such as fluorine, chlorine, bromine, or iodine), hydroxyl, carbonyl (such as a carboxyl, alkoxycarbonyl, formyl, or an acyl), thiocarbonyl (such as a thioester, a thioacetate, or a thioformate), aryl, alkoxyl, aralkyl, phosphonium, phosphanyl, phosphonyl, phosphoryl, phosphate, phosphonate, a phosphinate, amino, amido, amidine, imine, cyano, nitro, azido, oxo, sulfhydryl, thiol, alkylthio, silyl, sulfinyl, sulfate, sulfonate, sulfamoyl, sulfonamido, sulfonyl, heterocyclyl, an aromatic or heteroaromatic moiety. —NRR', wherein R and R' are independently hydrogen, alkyl, or aryl, and wherein the nitrogen atom is optionally quaternized; —SR, wherein R is a phosphonyl, a sulfinyl, a silyl a hydrogen, an alkyl, or an aryl; —CN; —$NO_2$; —COOH; carboxylate; —COR, —COOR, or —$CON(R)_2$, wherein R is hydrogen, alkyl, or aryl; imino, silyl, ether, haloalkyl (such as —CF3, —$CH_2$—$CF_3$, —$CCl_3$); —CN; —$NCOCOCH_2CH_2$, —NCOCOCHCH; and —NCS; and combinations thereof. The term "alkyl" also includes "heteroalkyl".

It will be understood by those skilled in the art that the moieties substituted on the hydrocarbon chain can themselves be substituted, if appropriate. For instance, the substituents of a substituted alkyl may include halogen, hydroxy, nitro, thiols, amino, aralkyl, azido, imino, amido, phosphonium, phosphanyl, phosphoryl (including phosphonate and phosphinate), oxo, sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

"Heteroalkyl," as used herein, refers to straight or branched chain, or cyclic carbon-containing alkyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "alkenyl" as used herein is a hydrocarbon group of from 2 to 24 carbon atoms and structural formula containing at least one carbon-carbon double bond. Alkenyl groups include straight-chain alkenyl groups, branched-chain alkenyl, and cycloalkenyl. A cycloalkenyl is a non-aromatic carbon-based ring composed of at least three carbon atoms and at least one carbon-carbon double bond, such as a nonaromatic monocyclic or nonaromatic polycyclic ring containing 3-30 carbon atoms and at least one carbon-carbon double bond, 3-20 carbon atoms and at least one carbon-carbon double bond, or 3-10 carbon atoms and at least one carbon-carbon double bond in their ring structure, and have 5, 6 or 7 carbons and at least one carbon-carbon double bond in the ring structure. Cycloalkenyls containing a polycyclic ring system can have two or more non-aromatic rings in which two or more carbons are common to two adjoining rings (i.e., "fused cycloalkenyl rings") and contain at least one carbon-carbon double bond. Asymmetric structures such as $(AB)C=C(C'D)$ are intended to include both the E and Z isomers. This may be presumed in structural formulae herein wherein an asymmetric alkene is present, or it may be explicitly indicated by the bond symbol C. The term "alkenyl" as used throughout the specification, examples, and claims is intended to include both "unsubstituted alkenyls" and "substituted alkenyls," the latter of which refers to alkenyl moieties having one or more substituents replacing a hydrogen on one or more carbons of the hydrocarbon backbone. The term "alkenyl" also includes "heteroalkenyl".

The term "substituted alkenyl" refers to alkenyl moieties having one or more substituents replacing one or more hydrogen atoms on one or more carbons of the hydrocarbon backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, oxo, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

"Heteroalkenyl," as used herein, refers to straight or branched chain, or cyclic carbon-containing alkynyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkenyl group" is a cycloalkenyl group where at least one of the carbon atoms of the ring is substituted with a heteroatom such as, but not limited to, nitrogen, oxygen, sulphur, or phosphorus.

The term "alkynyl group" as used herein is a hydrocarbon group of 2 to 24 carbon atoms and a structural formula containing at least one carbon-carbon triple bond. Alkynyl groups include straight-chain alkynyl groups, branched-chain alkynyl, and cycloalkynyl. A cycloalkynyl is a non-aromatic carbon-based ring composed of at least three carbon atoms and at least one carbon-carbon triple bond, such as a nonaromatic monocyclic or nonaromatic polycyclic ring containing 3-30 carbon atoms and at least one carbon-carbon triple bond, 3-20 carbon atoms and at least one carbon-carbon triple bond, or 3-10 carbon atoms and at least one carbon-carbon triple bond in their ring structure, and have 5, 6 or 7 carbons and at least one carbon-carbon triple bond in the ring structure. Cycloalkynyls containing a polycyclic ring system can have two or more non-aromatic rings in which two or more carbons are common to two adjoining rings (i.e., "fused cycloalkynyl rings") and contain at least one carbon-carbon triple bond. Asymmetric structures such as $(AB)C\equiv C(C'D)$ are intended to include both the E and Z isomers. This may be presumed in structural formulae herein wherein an asymmetric alkyne is present, or it may be explicitly indicated by the bond symbol C. The term "alkynyl" as used throughout the specification, examples, and claims is intended to include both "unsubstituted alkynyls" and "substituted alkynyls," the latter of which refers to alkynyl moieties having one or more substituents replacing a hydrogen on one or more carbons of the hydrocarbon backbone. The term "alkynyl" also includes "heteroalkynyl".

The term "substituted alkynyl" refers to alkynyl moieties having one or more substituents replacing one or more hydrogen atoms on one or more carbons of the hydrocarbon backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

"Heteroalkynyl," as used herein, refers to straight or branched chain, or cyclic carbon-containing alkynyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkynyl group" is a cycloalkynyl group where at least one of the carbon atoms of the ring is substituted with a heteroatom such as, but not limited to, nitrogen, oxygen, sulphur, or phosphorus.

The term "aryl" as used herein is any $C_5$-$C_{26}$ carbon-based aromatic group, heteroaromatic, fused aromatic, or fused heteroaromatic. For example, "aryl," as used herein can include 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused aromatic rings"), wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents. Such substituents can be any substituents described above, e.g., halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle" and "heterocyclyl" are used interchangeably, and refer to a cyclic radical attached via a ring carbon or nitrogen atom of a non-aromatic monocyclic or polycyclic ring containing 3-30 ring atoms, 3-20 ring atoms, 3-10 ring atoms, or 5-6 ring atoms, where each ring contains carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Heterocycles can be a heterocycloalkyl, a heterocycloalkenyl, a heterocycloalkynyl, etc, such as piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{30}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents. Such substituents can be any substituents described above, e.g., halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. For example, a "polyaryl" can be polycyclic ring systems having two or more cyclic rings in which two or more carbons are common to two adjoining rings (i.e., "fused aromatic rings"), wherein two or more of the rings are aromatic. When two or more heteroaryls are involved, the chemical moiety can be referred to as a "polyheteroaryl."

The term "substituted polyaryl" refers to a polyaryl in which one or more of the aryls, heteroaryls are substituted, with one or more substituents. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a "substituted polyheteroaryl."

The term "cyclic ring" or "cyclic group" refers to a substituted or unsubstituted monocyclic ring or a substituted or unsubstituted polycyclic ring (such as those formed from single or fused ring systems), such as a substituted or unsubstituted cycloalkyl, a substituted or unsubstituted cycloalkenyl, a substituted or unsubstituted cycloalkynyl, or a substituted or unsubstituted heterocyclyl, that have from three to 30 carbon atoms, as geometric constraints permit. The substituted cycloalkyls, cycloalkenyls, cycloalkynyls, and heterocyclyls are substituted as defined above for the alkyls, alkenyls, alkynyls, and heterocyclyls, respectively.

The term "aralkyl" as used herein is an aryl group or a heteroaryl group having an alkyl, alkynyl, or alkenyl group as defined above attached to the aromatic group, such as an aryl, a heteroaryl, a polyaryl, or a polyheteroaryl. An example of an aralkyl group is a benzyl group.

The terms "alkoxyl" or "alkoxy," "aroxy" or "aryloxy," generally describe compounds represented by the formula —OR", wherein $R^v$ includes, but is not limited to, a substituted or unsubstituted alkyl, a substituted or unsubstituted alkenyl, a substituted or unsubstituted alkynyl, a substituted or unsubstituted cycloalkyl, a substituted or unsubstituted heterocyclyl, a substituted or unsubstituted cycloalkenyl, a substituted or unsubstituted heterocycloalkenyl, a substituted or unsubstituted aryl, a substituted or unsubstituted heteroaryl, a substituted or unsubstituted polyaryl, a substituted or unsubstituted polyheteroaryl, a substituted or unsubstituted arylalkyl, a substituted or unsubstituted heteroalkyl, a substituted or unsubstituted alkylaryl, a substituted or unsubstituted alkylheteroaryl, a substituted or unsubstituted aralkyl, a substituted or unsubstituted carbonyl, a phosphonium, a phosphanyl, a phosphonyl, a sulfinyl, a silyl, a thiol, an amido, and an amino. Exemplary alkoxyl groups include methoxy, ethoxy, propyloxy, tert-butoxy and the like. A "lower alkoxy" group is an alkoxy group containing from one to six carbon atoms. An "ether" is two functional groups covalently linked by an oxygen as defined below. Accordingly, the substituent of an alkyl that renders that alkyl an ether is or resembles an alkoxyl, such as can be represented by one of —O-alkyl, —O-alkenyl, —O-alkynyl, —O-aralkyl, —O-aryl, —O-heteroaryl, —O-polyaryl, —O-polyheteroaryl, —O-heterocyclyl, etc.

The term "substituted alkoxy" refers to an alkoxy group having one or more substituents replacing one or more hydrogen atoms on one or more carbons of the alkoxy backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, oxo, sulfate, sulfonate, sulfamoyl, sulfonamido, sulfonyl, heterocyclyl, alkylaryl, haloalkyl, —CN, aryl, heteroaryl, and combinations thereof.

The term "ether" as used herein is represented by the formula $A^2OA^1$, where $A^2$ and $A^1$ can be, independently, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl, a substituted or unsubstituted polyaryl, a substituted or unsubstituted polyheteroaryl, a phosphonium, a phosphanyl, a phosphonyl, a sulfinyl, a silyl, a thiol, a substituted or unsubstituted carbonyl, an alkoxy, an amido, or an amino, described above.

The term "polyether" as used herein is represented by the formula:

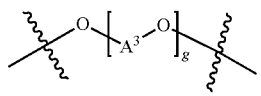

where $A^3$, $A^2$, and $A^1$ can be, independently, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl, a substituted or unsubstituted polyaryl, a substituted or unsubstituted polyheteroaryl, a phosphonium, a phosphanyl, a substituted or unsubstituted carbonyl, an alkoxy, an amido, or an amino, described above; g can be a positive integer from 1 to 30.

The term "phenoxy" is art recognized and refers to a compound of the formula —$OR^v$ wherein $R^v$ is $C_6H_5$ (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "amino" as used herein includes the group

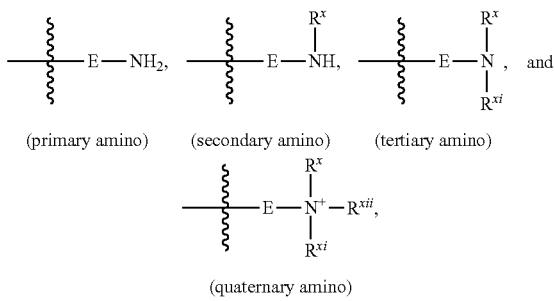

wherein, E is absent, or E is substituted or unsubstituted alkyl, substituted or unsubstituted alkenyl, substituted or unsubstituted alkynyl, substituted or unsubstituted aralkyl, substituted or unsubstituted aryl, substituted or unsubstituted heteroaryl, a substituted or unsubstituted polyaryl, a substituted or unsubstituted polyheteroaryl, substituted or unsubstituted heterocyclyl, wherein independently of E, $R^x$, $R^{xi}$, and $R^{xii}$ each independently represent a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—R'''; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8. The term "quaternary amino" also includes the groups where the nitrogen, $R^x$, $R^{xi}$, and $R^{xii}$ with the $N^+$ to which they are attached complete a heterocyclyl or heteroaryl having from 3 to 14 atoms in the ring structure.

The terms "amide" or "amido" are used interchangeably, refer to both "unsubstituted amido" and "substituted amido" and are represented by the general formula:

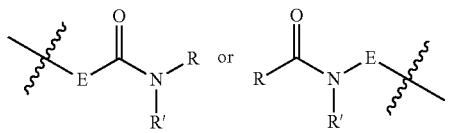

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted aryl, substituted or unsubstituted heteroaryl, a substituted or unsubstituted polyaryl, a substituted or unsubstituted polyheteroaryl, or a substituted or unsubstituted heterocyclyl, wherein independently of E, R and R' each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—R''', or R and R' taken together with the N atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8. In some forms, when E is oxygen, a carbamate is formed.

"Carbonyl," as used herein, is art-recognized and includes such moieties as can be represented by the general formula:

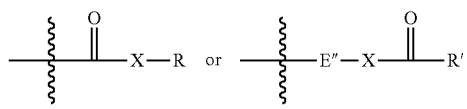

wherein X is a bond, or represents an oxygen or a sulfur, and R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or —$(CH_2)_m$—R''', or a pharmaceutical acceptable salt; E'' is absent, or E'' is substituted or unsubstituted alkyl, substituted or unsubstituted alkenyl, substituted or unsubstituted alkynyl, substituted or unsubstituted aralkyl, substituted or unsubstituted aryl, substituted or unsubstituted heteroaryl, a substituted or unsubstituted polyaryl, a substituted or unsubstituted polyheteroaryl, substituted or unsubstituted heterocyclyl; R' represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or —$(CH_2)_m$—R''; R'' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8. Where X is oxygen and R is defined as above, the moiety is also referred to as a carboxyl group. When X is oxygen and R is hydrogen, the formula represents a "carboxylic acid". Where X is oxygen and R' is hydrogen, the formula represents a "formate". Where X is oxygen and R or R' is not hydrogen, the formula represents an "ester". In general, where the oxygen atom of the above formula is replaced by a sulfur atom, the formula represents a "thiocarbonyl" group. Where X is sulfur and R or R' is not hydrogen, the formula represents a "thioester". Where X is sulfur and R is hydrogen, the formula represents a "thiocarboxylic acid". Where X is sulfur and R' is hydrogen, the formula represents a "thioformate". Where X is a bond and R is not hydrogen, the above formula represents a "ketone". Where X is a bond and R is hydrogen, the above formula represents an "aldehyde".

The term "substituted carbonyl" refers to a carbonyl, as defined above, wherein one or more hydrogen atoms in R, R' or a group to which the moiety

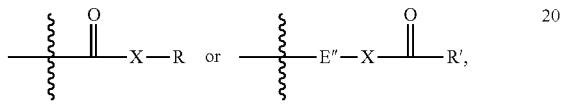

is attached, are independently substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for carbonyl and is defined more specifically by the formula —$R^{iv}$COOH, wherein $R^{iv}$ is a substituted or unsubstituted alkyl, a substituted or unsubstituted alkenyl, a substituted or unsubstituted alkynyl, a substituted or unsubstituted heterocyclyl, a substituted or unsubstituted alkylaryl, a substituted or unsubstituted arylalkyl, a substituted or unsubstituted aryl, a substituted or unsubstituted polyaryl, a substituted or unsubstituted polyheteroaryl, or a substituted or unsubstituted heteroaryl.

The term "substituted carboxyl" refers to a carboxyl, as defined above, wherein one or more hydrogen atoms in $R^{iv}$ are substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "phosphanyl" is represented by the formula

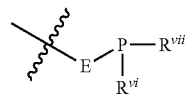

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted cycloalkyl, a substituted or unsubstituted aryl, a substituted or unsubstituted heteroaryl, a substituted or unsubstituted polyaryl, a substituted or unsubstituted polyheteroaryl, a substituted or unsubstituted heterocyclyl, wherein independently of E, $R^{vi}$ and $R^{vii}$ each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—$R'''$, or $R^{vi}$ and $R^{vii}$ taken together with the P atom to which they are attached complete a heterocycle having from 3 to 14 atoms in the ring structure; $R'''$ represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "phosphonium" is represented by the formula

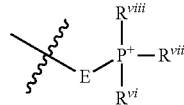

wherein, E is absent, or E is a substituted or unsubstituted alkyl, a substituted or unsubstituted alkenyl, a substituted or unsubstituted alkynyl, a substituted or unsubstituted aralkyl, a substituted or unsubstituted cycloalkyl, a substituted or unsubstituted aryl, a substituted or unsubstituted heteroaryl, a substituted or unsubstituted polyaryl, a substituted or unsubstituted polyheteroaryl, a substituted or unsubstituted heterocyclyl, wherein independently of E, $R^{vi}$, $R^{vii}$, and $R^{viii}$ each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—$R'''$, or $R^{vi}$, $R^{vii}$, and $R^{viii}$ taken together with the $P^+$ atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "phosphonyl" is represented by the formula

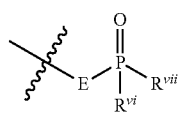

wherein E is absent, or E is a substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, oxygen, alkoxy, aroxy, or substituted alkoxy or substituted aroxy, wherein, independently of E, $R^{vi}$ and $R^{vii}$ are independently a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a sulfinyl, a silyl, a thiol, an amido, an amino, or —$(CH_2)_m$—R''', or $R^{vi}$ and $R^{vii}$ taken together with the P atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "substituted phosphonyl" represents a phosphonyl in which E, $R^{vi}$ and $R^{vii}$ are independently substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "sulfinyl" is represented by the formula

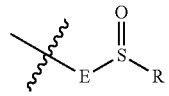

wherein E is absent, or E is a substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted arylalkyl, etc.), a substituted or unsubstituted aryl, a substituted or unsubstituted heteroaryl, a substituted or unsubstituted heterocyclyl, a substituted or unsubstituted polyaryl, a substituted or unsubstituted polyheteroaryl, wherein independently of E, R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, a phosphonyl, a silyl, a thiol, an amido, an amino, or —$(CH_2)_m$—R''', or E and R taken together with the S atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "sulfonyl" is represented by the formula

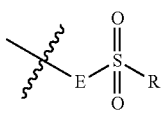

wherein E is absent, or E is a substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted arylalkyl, etc.), a substituted or unsubstituted aryl, a substituted or unsubstituted heteroaryl, a substituted or unsubstituted heterocyclyl, a substituted or unsubstituted polyaryl, a substituted or unsubstituted polyheteroaryl, wherein independently of E, R represents a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or —$(CH_2)_m$—R''', or E and R taken together with the S atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "substituted sulfonyl" represents a sulfonyl in which E, R, or both, are independently substituted. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, a substituted or unsubstituted polyaryl, a substituted or unsubstituted polyheteroaryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amino, substituted or unsubstituted cycloalkyl, substituted or unsubstituted heterocyclyl, substituted or unsubstituted aralkyl, substituted or unsubstituted alkylaryl, substituted or unsubstituted arylalkyl, substituted or unsubstituted aryl, substituted or unsubstituted heteroaryl, a substituted or unsubstituted polyaryl, a substituted or unsubstituted polyheteroaryl, —$(CH_2)_m$—R''', R''' represents a hydroxy group, substituted or unsubstituted carbonyl group, an aryl, a cycloalkyl ring, a cycloalkenyl ring, a heterocycle, an amido, an amino, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

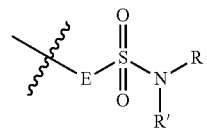

wherein E is absent, or E is substituted or unsubstituted alkyl, a substituted or unsubstituted alkenyl, a substituted or unsubstituted alkynyl, a substituted or unsubstituted aralkyl (e.g., a substituted or unsubstituted alkylaryl, a substituted or unsubstituted cycloalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, wherein independently of E, R and R' each independently represent a hydrogen, a substituted or unsubstituted alkyl, a substituted or unsubstituted alkenyl, a substituted or unsubstituted alkynyl, a substituted or unsubstituted carbonyl, a substituted or unsubstituted heterocyclyl, a substituted or unsubstituted aralkyl (e.g. a substituted or unsubstituted alkylaryl, a substituted or unsubstituted arylalkyl, etc.), a substituted or unsubstituted aryl, a substituted or unsubstituted heteroaryl, a substituted or unsubstituted polyaryl, a substituted or unsubstituted polyheteroaryl, a substituted or unsubstituted heterocyclyl, a hydroxyl, an alkoxy, a phosphonium, a phosphanyl, an amido, an amino, or —$(CH_2)_m$—R''', or R and R' taken together with the N atom to which they are attached complete a heterocycle having from 3 to 14 atoms in the ring structure; R''' represents a hydroxyl group, a substituted or unsubstituted carbonyl group, a substituted or unsubstituted aryl, a substituted or unsubstituted cycloalkyl, a substituted or unsubstituted cycloalkenyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, an alkoxy, a phosphonium, a phosphanyl, an amido, or an amino; and m is zero or an integer ranging from 1 to 8.

The term "silyl group" as used herein is represented by the formula —SiRR'R", where R, R', and R" can be, independently, a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl (e.g. a substituted or unsubstituted alkylaryl, a substituted or unsubstituted arylalkyl, etc.), a substituted or unsubstituted polyaryl, a substituted or unsubstituted polyheteroaryl, a substituted or unsubstituted carbonyl, a phosphonium, a phosphanyl, a phosphonyl, a sulfinyl, a thiol, an amido, an amino, an alkoxy, or an oxo, described above.

The terms "thiol" are used interchangeably and are represented by —SR, where R can be a hydrogen, a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted aralkyl (e.g. a substituted or unsubstituted alkylaryl, a substituted or unsubstituted arylalkyl, etc.), a substituted or unsubstituted polyaryl, a substituted or unsubstituted polyheteroaryl, a substituted or unsubstituted carbonyl, a phosphonium, a phosphanyl, an amido, an amino, an alkoxy, an oxo, a phosphonyl, a sulfinyl, or a silyl, described above.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "hydroxyl" and "hydroxy" are used interchangeably and are represented by —OH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The compounds and substituents can be substituted with, independently, with the substituents described above in the definition of "substituted."

II. Methods for Asymmetric Cis-Dihydroxylation of Quinones

Methods for asymmetric cis-dihydroxylation ("AD") of quinones to produce cis-diols of quinones with high yield (i.e. a yield ≥30%, such as a yield of about 90%) and high enantioselectivity (i.e. an enantiometric excess ("ee")≥30%, such as an ee of about 99.8%) have been developed. The cis-diols of quinones produced from the methods described herein are powerful building blocks for the bioactive natural products and active pharmaceutical ingredients ("APIs").

Due to the electron-deficient nature of quinones and their planar structures, conventional AD reactions of electron-rich and/or non- or less-planar alkenes (such as olefins and phenyl alkenes) can hardly be extended to AD of quinones, see, for example, experimental results using $OsO_4$ or AD-mix-beta as catalysts for AD reactions as shown in Table 7 in the Examples. The methods described herein use an iron-based catalyst, such as one or more Fe(II) complexes, as the catalyst, and can be performed under mild reaction conditions (e.g., a temperature ≤50° C. at 1 atm in open air). The methods described herein have at least the following advantages: (1) cis-diols of quinones can be produced with high yield and high enantioselectivity; (2) the use of biocompatible iron-based catalysts is environmentally friendly and cost efficient; (3) the waste generated from the reaction is non-toxic; and (4) the reactions can be performed under ambient conditions.

The methods described herein overcome the disadvantages associated with conventional AD reactions of alkenes using Os-based catalysts (e.g., the commercial products AD-mix-α/β developed by Sharpless and co-workers), which are expensive due to the low abundance of osmium metal on earth and have environmental and health concerns due to the production of overstoichiometric amounts of toxic wastes. For example, in AD reactions using osmium-based catalysts, $K_3Fe(CN)_6$ is typically added as a terminal oxidant, which produces an equivalent waste of $K_4Fe(CN)_6$. Over-stoichiometric amount of $K_2CO_3$ is also needed as an additive in osmium-based catalysis. The methods described herein can use hydrogen peroxide as the terminal oxidant, which is a green oxidant and is converted to the two hydroxyl (OH) groups onto product molecules with 100% atom efficiency and do not need any additive. Additionally, the yield and enantioselectivity of cis-diol(s) of quinones produced using the methods described herein are higher compared to Os-based catalysts (such as $OsO_4$ and AD-mix-β). For example, the cis-diol(s) produced from AD of a quinone using the methods described herein has a yield and/or an enantioselectivity that are/is higher than the yield and/or enantioselectivity of the same cis-diol(s) produced from the same reaction (e.g. using the same quinones to form the same cis-diol products), using the same loading or a higher loading of $OsO_4$ and/or AD-mix-α/β compared to the loading of the iron-based catalyst disclosed herein.

The method generally includes: (i) maintaining a reaction mixture at a temperature for a period of time sufficient to form a product, where the reaction mixture contains a quinone, one or more iron-based catalyst(s), and a solvent, and where the product contains a cis-diol.

Optionally, the method also includes adding an oxidant (e.g., a hydrogen peroxide solution) into the reaction mixture prior to and/or during step (i); adding one or more additive(s) into the reaction mixture prior to and/or during step (i); stirring the reaction mixture prior to and/or during step (i); and/or purifying the product, optionally by column chromatography, subsequent to step (i).

A. Maintaining a Reaction Mixture at a Temperature for a Period of Time Sufficient to Form a Product Generally, a reaction mixture containing a quinone and one or more iron-based catalyst(s) disclosed herein in a suitable solvent is maintained at a suitable temperature for a period of time sufficient to form a product containing cis-diols of the quinone. Typically, the reaction conditions for performing the reaction are mild and simple. For example, the temperature for performing the reaction can be up to about 50° C., in a range from about 20° C. to about 50° C., from about 20° C. to about 40° C., from about 20° C. to about 30° C., or from about 20° C. to about 25° C., at 1 atm, for example, room temperature (i.e. from about 20° C. to about 22° C., at 1 atm); the time period for performing the reaction at any of the temperature ranges described above can be up to 3 hours, up to 2 hours, or up to 1 hour, in a range from about 20 minutes to about 3 hours, from about 30 minutes to about 2 hours, or from about 30 minutes to 1 hour; and the reaction can be performed in open air.

The reaction mixture can be formed by dissolving the quinone and the iron-based catalyst(s) in the solvent prior to reaction. Suitable solvents for forming the reaction mixture can dissolve the quinone and the iron-based catalyst(s). For example, the quinone has a solubility of at least 0.01 M and the iron-based catalyst(s) has a solubility of at least 0.0015 M in the solvent. Examples of solvents suitable for forming the reaction mixture include, but are not limited to an alcohol (e.g. a $C_1$-$C_6$ alcohol, such as methanol, ethanol, propanol, etc.), acetonitrile, tetrahydrofuran, and a combination thereof. In some forms, the solvent forming the reaction mixture is not dichloromethane.

1. Quinones

The reaction mixture contains a quinone, optionally more than one quinones, serving as the substrate in the catalytic reaction. The quinone(s) in the reaction mixture can be 1,4-quinone or 1,2-quinones, or a mixture thereof. Preferably, the quinone(s) in the reaction mixture are 1,4-quinones.

In some forms, the quinone or each of the two or more quinones in the reaction mixture can have the structure of Formula I or Formula II:

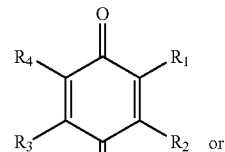

Formula I

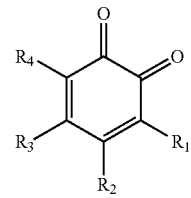

Formula II where: (a) $R_1$-$R_4$ can be independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (b) the substituents can be independently a substituted or unsubstituted alkyl (such as haloalkyl, e.g., —$CF_3$), a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms of Formulae I and II, at least one of $R_1$-$R_4$, at least two of $R_1$-$R_4$, or at least three of $R_1$-$R_4$ can be an or are electron-donating group(s). In some forms of Formulae I and II, at least one of $R_1$-$R_4$ can be hydrogen. In some forms of Formulae I and II, at least one of $R_1$-$R_4$ can be an electron-donating group and at least one of $R_1$-$R_4$ can be hydrogen. In some forms of Formulae I and II, $R_2$ can be hydrogen and $R_1$, $R_3$, and $R_4$ can be any of the groups as defined for Formulae I and II above. In some forms of Formulae I and II, $R_3$ can be hydrogen and $R_1$, $R_2$, and $R_4$ can be any of the groups as defined for Formulae I and II above. In some forms of Formulae I and II, $R_1$ and $R_2$ can be hydrogen and $R_3$ and $R_4$ can be any of the groups as defined for Formulae I and II above. In some forms of Formulae I and II, $R_3$ and $R_4$ can be hydrogen and $R_1$ and $R_2$ can be any of the groups as defined for Formulae I and II above. In some forms of Formulae I and II, at least $R_3$ is not hydrogen. In some forms of Formula I, at least $R_3$ is not an electron-withdrawing group, such as halide, carbonyl, nitro, ammonium, trihalomethylsulfonyl, sulfonic acid, sulfonyl, cyano, trihalomethyl, haloformyl, aminocarbonyl, or nitroso.

In some forms of Formulae I and II, $R_1$-$R_4$ can be independently a hydrogen, a substituted or unsubstituted alkyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic group, a substituted or unsubstituted aralkyl, an alkoxyl, or a carbonyl, or two neighboring R groups together with the carbon atoms to which they are attached can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group. In some forms of Formula I, $R_1$ and $R_2$ together and/or $R_3$ and $R_4$ together, with the carbon atoms to which they are attached, can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group. In some forms of Formula II, $R_1$ and $R_2$ together, $R_2$ and $R_3$ together, and/or $R_3$ and $R_4$ together, with the carbon atoms to which they are attached, can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

In some forms of Formulae I and II, $R_1$-$R_4$ can be independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

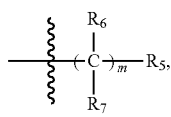

$R_5$ can be a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ can be independently a hydrogen or a substituted or unsubstituted alkyl, and m can be an integer from 1 to 10, from 1 to 8, from 1 to 6, from 1 to 4, from 1 to 3, or 1 or 2, or two neighboring R groups together with the carbon atoms to which they are attached can form a substituted or unsubstituted aryl or a substituted or unsubstituted polyaryl.

In some forms of Formulae I and II, $R_1$-$R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

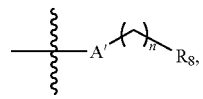

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, from 1 to 6, from 1 to 4, from 1 to 3, or 1 or 2, or two neighboring R groups can form a substituted or unsubstituted aryl or a substituted or unsubstituted polyaryl.

In some forms of Formulae I and II, $R_1$-$R_4$ can be selected to control the location of the AD reaction. For example, $R_3$ and/or $R_4$ of Formula I are functional groups that are bulkier than $R_1$ and $R_2$, such that the AD reaction occurs at the less sterically hindered $R_1$ and $R_2$ substituted C=C double bond. For example, $R_1$ and/or $R_2$ of Formula I are electron-deficient functional group, such as a halide-substituted phenyl group, such that the AD reaction occurs at the $R_1$ and/or $R_2$ substituted C=C double bond.

In some forms, the quinone or each of the two or more quinones in the reaction mixture has the structure of Formula I as defined above. In some forms, the quinone or each of the two or more quinones in the reaction mixture is not a 1,4-quinone.

In some forms, the quinone or each of the two or more quinones in the reaction mixture can have a structure of Formula III:

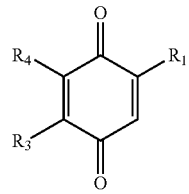

Formula III where $R_1$, $R_3$, and $R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

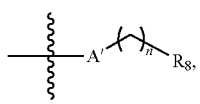

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, from 1 to 6, from 1 to 4, from 1 to 3, or 1 or 2, or $R_3$ and $R_4$ together can form a substituted or unsubstituted aryl or a substituted or unsubstituted polyaryl; and the substituents can be as defined above for Formulae I and II.

In some forms of Formula III, $R_3$ is not hydrogen. In some forms of Formula III, $R_1$ and $R_3$ are not hydrogen. In some forms of Formula III, $R_1$, $R_3$, and $R_4$ are not hydrogen. In some forms of Formula III, $R_1$-$R_4$ can be selected to control the location of the AD reaction. For example, $R_3$ and/or $R_4$ of Formula III are functional groups that are bulkier than $R_1$, such that the AD reaction occurs at the less sterically hindered $R_1$ and $R_2$ substituted C═C double bond. For example, $R_1$ of Formula III is an electron-deficient functional group, such as a halide-substituted phenyl group, such that the AD reaction occurs at the $R_1$ substituted C═C double bond.

In some forms, the quinone or each of the two or more quinones in the reaction mixture can have a structure of Formula IV:

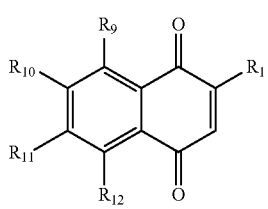

Formula IV where: (a) $R_1$ can be a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

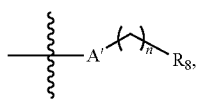

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, from 1 to 6, from 1 to 4, from 1 to 3, or 1 or 2; and (b) $R_9$-$R_{12}$ can be independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

In some forms of Formula IV, $R_9$-$R_{12}$ can be independently a hydrogen, a halide, a hydroxyl, an aroxy, an alkoxyl, or $R_{11}$ and $R_{12}$ together with the carbon atoms to which they are attached can form a substituted or unsubstituted cycloalkenyl, a substituted or unsubstituted polycycloalkenyl, a substituted or unsubstituted aryl or a substituted or unsubstituted polyaryl.

In some forms, the quinone or each of the two or more quinones in the reaction mixture meets all of the following criteria: (1) is not a 1,2-quinone; (2) is not a tetrasubstituted quinone; and (3) at least one of $R_2$ and $R_3$ is not an electron-withdrawing group, such as those described above.

Exemplary quinones suitable for use in the reaction are presented below.

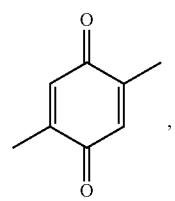

1a

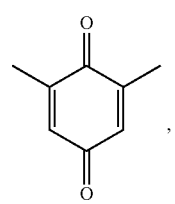

1b

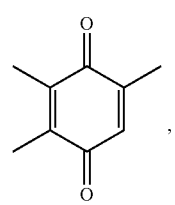

1c

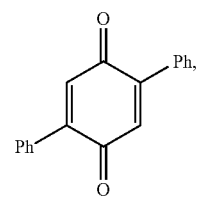

1d

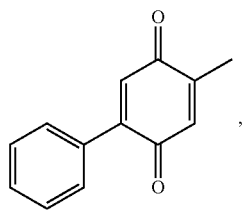
1e,
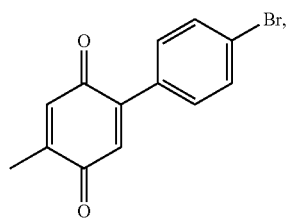
1f,
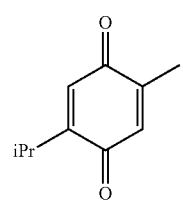
1g,
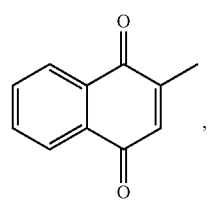
1h,
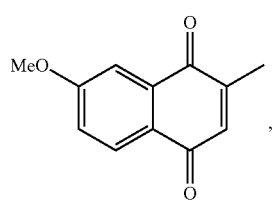
1i,
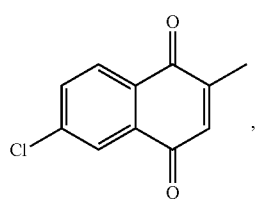
1j,
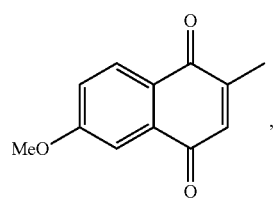
1k,
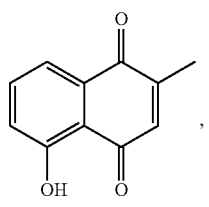
1l,
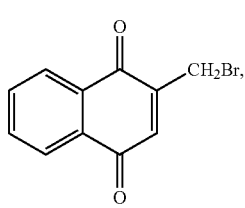
1m,
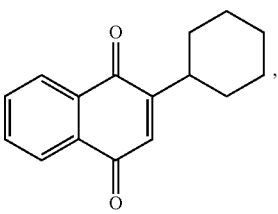
1n,
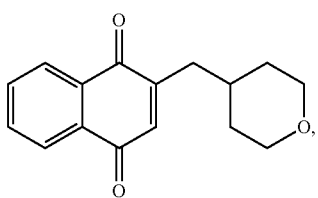
1o,
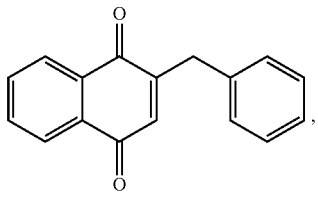
1p,
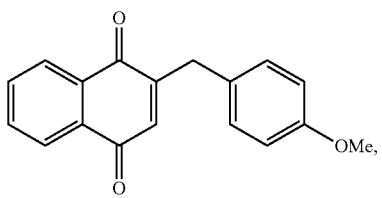
1q,
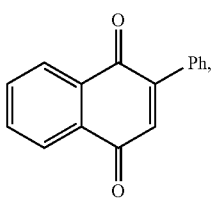
1r,

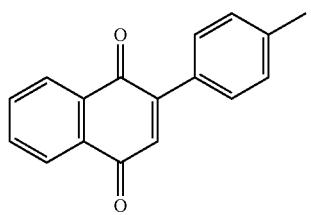
1s
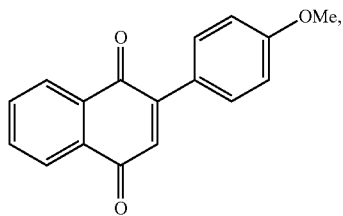
1t
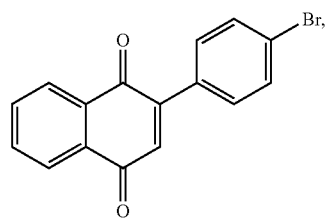
1u
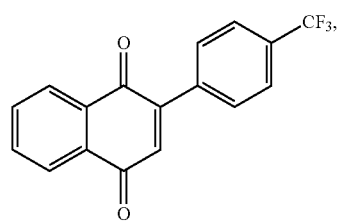
1v
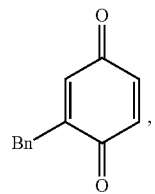
3b
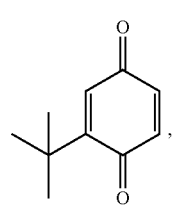
3c
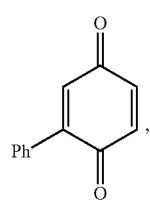
3d
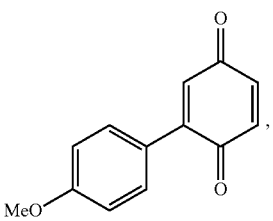
3e
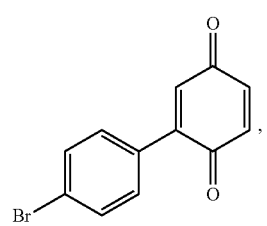
3f
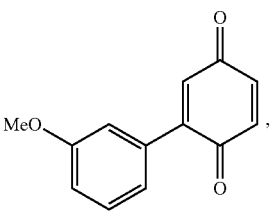
3g
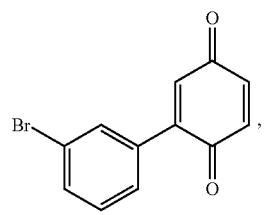
3h
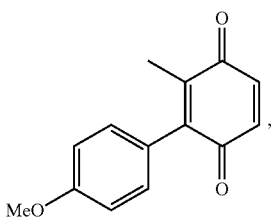
3i
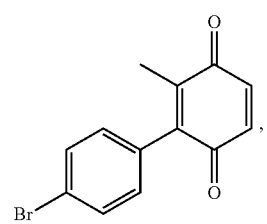
3j
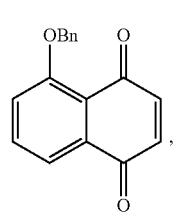
3k

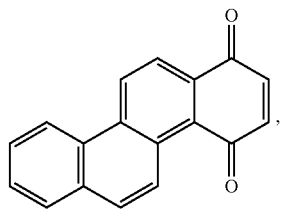

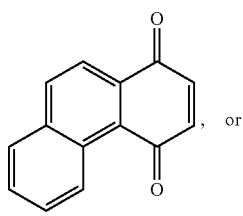, or

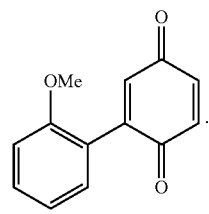.

In some forms, the quinone or each of the two or more quinones in the reaction mixture is not the following:

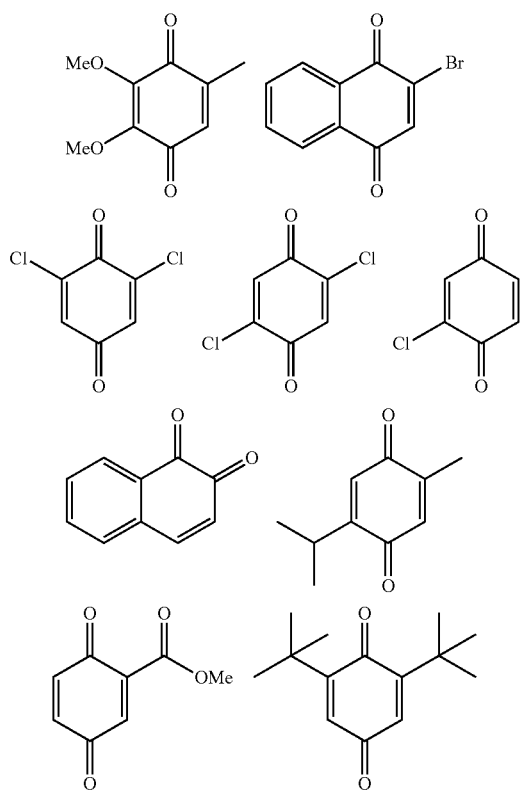

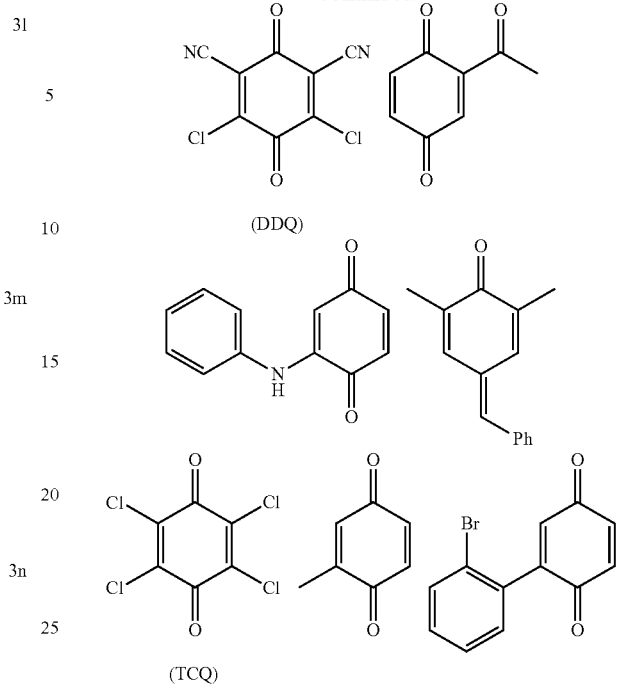

The substrates, i.e. the quinones, described herein can be synthesized using methods known in the art of organic chemical synthesis. For example, the target substrates can be synthesized by reacting one or more corresponding reactants in a suitable solvent.

The reaction solution containing the one or more corresponding reactants can be stirred at a suitable temperature for a suitable time to form a product containing the target substrates. The product containing the target substrates can be purified to isolate the target substrates. More specific reagents and reaction conditions are described in the Examples.

2. Iron-Based Catalysts

The AD reactions of quinone(s) described herein are catalyzed by an iron-based catalyst, optionally more than one iron-based catalysts. For example, the AD reactions of the one or more quinone(s) of any of Formulae I-IV in the reaction mixture are catalyzed by one or more Fe(II) complex(es). In some forms, the Fe(II) complex or each Fe(II) complex of the two or more catalysts in the reaction mixture can have the structure of Formula IX:

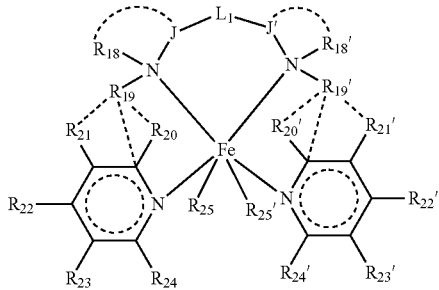

Formula IX where: (a) J and J' can be independently a bond (single, double, or triple), a substituted or unsubstituted alkyl, a substituted or unsubstituted alkenyl, a substituted or unsubstituted cyclic group, a substituted or unsubstituted aryl, or a substituted or unsubstituted polyaryl; (b) $L_1$ can be a bond or

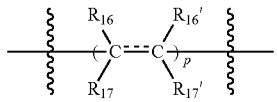

$R_{16}$, $R_{16}'$, $R_{17}$, and $R_{17}'$ can be independently a hydrogen, a substituted or unsubstituted alkyl, a substituted or unsubstituted alkenyl, a substituted or unsubstituted aryl, a substituted or unsubstituted polyaryl, or a substituted or unsubstituted cyclic group, or $R_{16}$ and $R_{16}'$ together and/or $R_{17}$ and $R_{17}'$ together, with the carbon atoms to which they are attached, can form a substituted or unsubstituted aryl, a substituted or unsubstituted polyaryl, or a substituted or unsubstituted cyclic group, and p can be an integer from 1 to 10, from 1 to 8, from 1 to 6, from 1 to 4, from 1 to 3, or 1 or 2; (c) $R_{18}$-$R_{24}$ and $R_{18}'$-$R_{24}'$ can be independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl; (d) $R_{25}$ and $R_{25}'$ can be independently a leaving group; (e)—can be absent or a bond (single, double, or triple); and (f) the substituents can be independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms of Formula IX, $R_{19}$, $R_{20}$, and $R_{21}$ together and/or $R_{19}'$, $R_{20}'$, and $R_{21}'$ together, with the carbon atoms to which they are attached, can be form a substituted or unsubstituted aryl, a substituted or unsubstituted polyaryl, or a substituted or unsubstituted cyclic group.

In some forms, the Fe(II) complex or each Fe(II) complex of the two or more catalysts in the reaction mixture can have the structure of Formula X, XI, or XIII

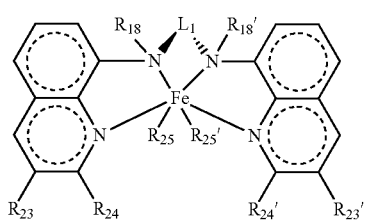

Formula X

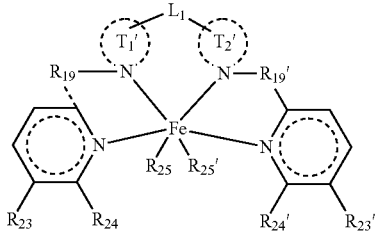

Formula XI

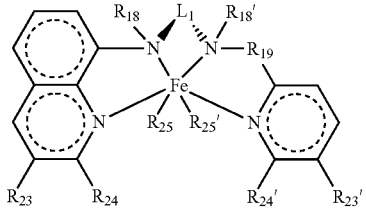

Formula XIII where: (a) $L_1$ can be a bond or

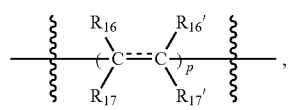

$R_{16}$, $R_{16}'$, $R_{17}$, and $R_{17}'$ can be independently a hydrogen, a substituted or unsubstituted alkyl, a substituted or unsubstituted alkenyl, a substituted or unsubstituted aryl, a substituted or unsubstituted polyaryl, or a substituted or unsubstituted cyclic group, or $R_{16}$ and $R_{16}'$ together and/or $R_{17}$ and $R_{17}'$ together, with the carbon atoms to which they are attached, can form a substituted or unsubstituted aryl, a substituted or unsubstituted polyaryl, or a substituted or unsubstituted cyclic group, and p is an integer from 1 to 10, from 1 to 8, from 1 to 6, from 1 to 4, from 1 to 3, or 1 or 2; (b) $T_1'$ and $T_2'$ can be independently a substituted or unsubstituted heteroaryl, a substituted or unsubstituted heteropolyaryl, or a substituted or unsubstituted heterocyclic group; (c) $R_{18}$, $R_{19}$, $R_{23}$, $R_{24}$, $R_{18}'$, $R_{19}'$, $R_{23}'$, and $R_{24}'$ can be independently a hydrogen, a substituted or unsubstituted alkyl, a substituted or unsubstituted alkenyl, or a substituted or unsubstituted aryl; (d) $R_{25}$ and $R_{25}'$ can be independently a leaving group; and (e) the substituents can be as defined above for Formula IX.

In some forms of Formulae IX-XI and XIII, $L_1$ can be a bond,

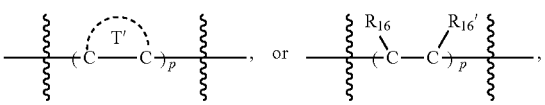

each occurrence of T' can be a substituted or unsubstituted monocyclic group, a substituted or unsubstituted polycyclic group, a substituted or unsubstituted aryl, or a substituted or unsubstituted polyaryl, each occurrence of $R_{16}$ and $R_{16}'$ can be independently a substituted or unsubstituted phenyl, and p is an integer from 1 to 10, from 1 to 8, from 1 to 6, from 1 to 4, from 1 to 3, or 1 or 2.

In some forms of Formulae IX-XI and XIII, $L_1$ can be

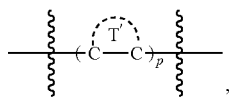

each occurrence of T' is a substituted or unsubstituted monocyclic group (e.g. an unsubstituted monocycloalkyl, such as an unsubstituted $C_3$-$C_6$ monocycloalkyl) or a substituted or unsubstituted polycyclic group (e.g. an unsubstituted polycycloalkyl) and p is an integer from 1 to 3, or 1 or 2, such as 1.

In some forms of Formulae IX-XI and XIII, $R_{25}$ and $R_{25'}$ can be independently a triflate, a tosylate, a mesylate, a halide, a nitrate, a phosphate, a thioether, an amino, a carboxylate, a phenoxide, an alkoxyl, or an amido, such as a triflate.

In some forms, the Fe(II) complex for catalyzing the AD of quinones can have the structure of Formula XII, XIV, or XV.

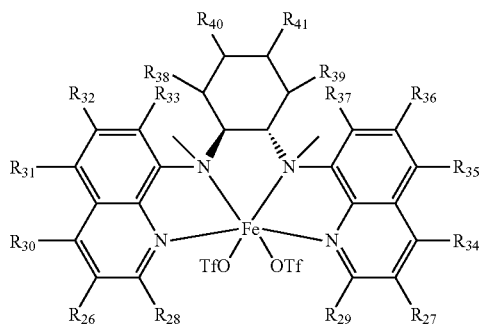

Formula XII

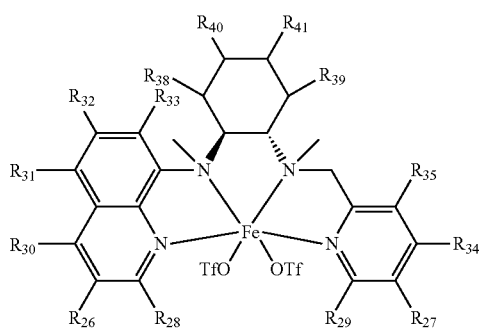

Formula XIV

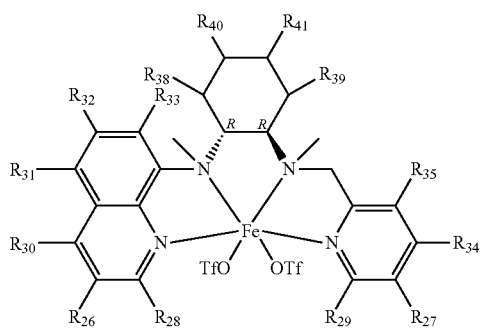

Formula XV where: (a) $R_{26}$ and $R_{27}$ can be independently hydrogen, a substituted or unsubstituted cyclic group, a substituted or unsubstituted aryl, or a substituted or unsubstituted polyaryl; (b) $R_{28}$-$R_{41}$ can be independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl; and (c) the substituents can be independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof. In some forms of Formula XII, $R_{26}$ and $R_{27}$ are not hydrogen.

In some forms of Formula XII, $R_{26}$ and $R_{27}$ can be independently a substituted or unsubstituted aryl, or a substituted or unsubstituted polyaryl; (b) $R_{28}$-$R_{41}$ can be independently a hydrogen, a substituted or unsubstituted alkyl, or a substituted or unsubstituted alkenyl; and (c) the substituents can be independently a substituted or unsubstituted alkyl, a substituted or unsubstituted alkenyl, or a substituted or unsubstituted alkynyl, or a combination thereof.

In some forms, for any of Formulae XIV and XV, $R_{26}$ and $R_{27}$ can be independently hydrogen, a substituted or unsubstituted alkyl, or a substituted or unsubstituted aryl; (b) $R_{28}$ and $R_{29}$ can be independently a hydrogen, a substituted or unsubstituted alkyl, or a substituted or unsubstituted alkenyl; (c) $R_{30}$-$R_{41}$ can be independently hydrogen or a substituted or unsubstituted alkyl; and (d) the substituents can be independently a substituted or unsubstituted alkyl, a substituted or unsubstituted alkenyl, or a substituted or unsubstituted alkynyl, or a combination thereof.

In some forms of Formula XII, (a) $R_{26}$ and $R_{27}$ can be independently a substituted or unsubstituted aryl; (b) $R_{28}$-$R_{41}$ can be independently a hydrogen, an unsubstituted alkyl, or an unsubstituted alkenyl; and (c) the substituents can be independently an unsubstituted alkyl, an unsubstituted alkenyl, an unsubstituted alkynyl, or a combination thereof.

In some forms of Formula XII, (a) $R_{26}$ and $R_{27}$ can be independently an unsubstituted aryl and (b) $R_{28}$-$R_{41}$ can be independently a hydrogen, an unsubstituted alkyl, or an unsubstituted alkenyl.

In some forms, for any of Formulae XIV and XV, (a) $R_{26}$ and $R_{27}$ can be hydrogen, (b) $R_{28}$ and $R_{29}$ can be independently a substituted or unsubstituted alkyl, such as an unsubstituted $C_1$-$C_8$ alkyl, and (c) $R_{30}$-$R_{40}$ can be hydrogen.

Exemplary iron-based catalysts suitable for use in the reaction are presented below.

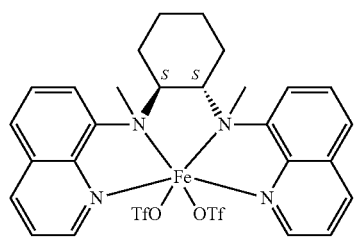
Fe<sup>II</sup>(L1)(OTf)₂
[Fe<sup>II</sup>(L2)(OTf)₂]
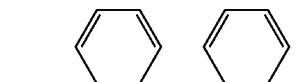
Fe<sup>II</sup>(L3)(OTf)₂]
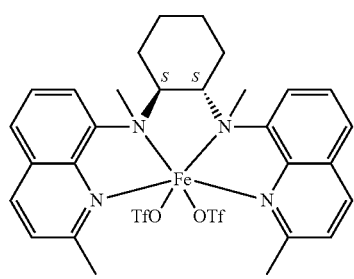
Fe<sup>II</sup>(L4)(OTf)₂
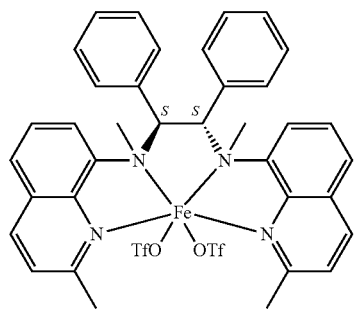
Fe<sup>II</sup>(L5)(OTf)₂
-continued
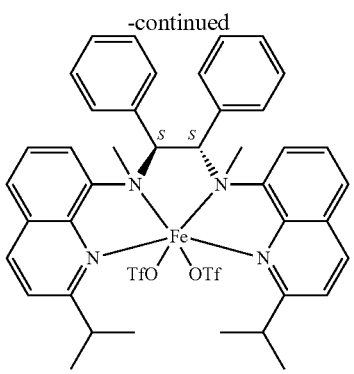
Fe<sup>II</sup>(L6)(OTf)₂
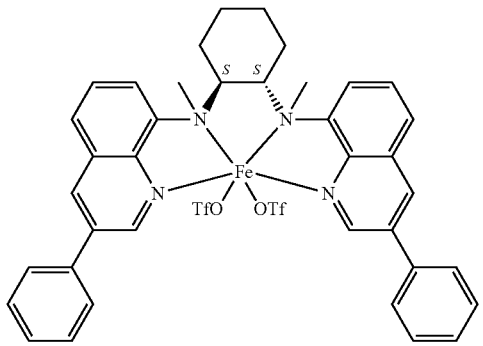
Fe<sup>II</sup>(L7)(OTf)₂
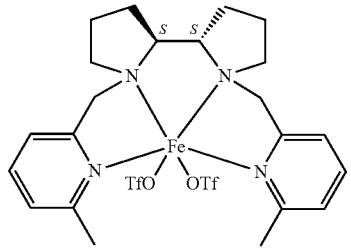
Fe<sup>II</sup>(L8)(OTf)₂
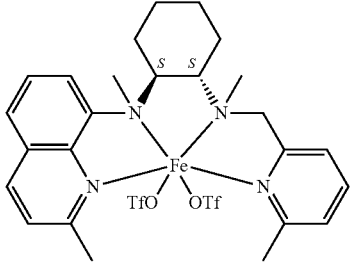
Fe<sup>II</sup>(L9)(OTf)₂
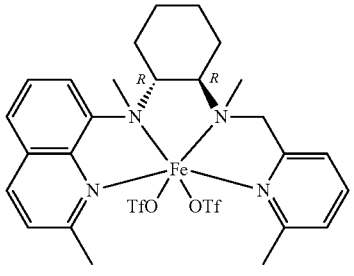
Fe<sup>II</sup>(L9-R)(OTf)₂

In some forms, the Fe(II) complex or each Fe(II) complex of the two or more catalysts in the reaction mixture is not the following:

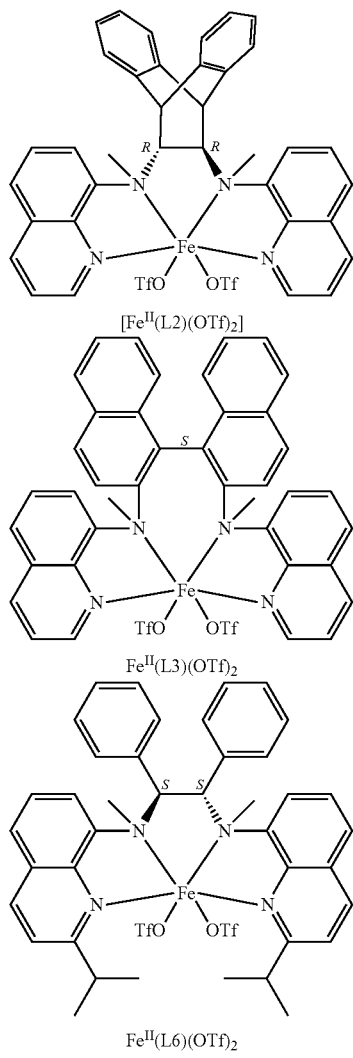

[Fe$^{II}$(L2)(OTf)$_2$]

Fe$^{II}$(L3)(OTf)$_2$

Fe$^{II}$(L6)(OTf)$_2$

Generally, the total amount of the one or more iron-based catalyst(s) in the reaction mixture is up to 10 mol %. The total amount of the one or more catalyst(s) in the reaction mixture can be calculated using the formula: mol % of the iron-based catalyst(s)=[(the sum of the nos. of moles of the one or more iron-based catalyst(s))/(the sum of the nos. of moles of the quinone(s)]×100%.

In some forms, the total amount of the one or more iron-based catalyst(s) in the reaction mixture is up to 10 mol %, up to 5 mol %, up to 3 mol %, at least 0.1 mol %, at least 0.5 mol %, in a range from about 0.1 mol % to about 10 mol %, from about 0.1 mol % to about 5 mol %, from about 0.1 mol % to about 3 mol %, from about 0.5 mol % to about 10 mol %, from about 0.5 mol % to about 5 mol %, from about 0.5 mol % to about 3 mol %, from about 1 mol % to about 10 mol %, from about 1 mol % to about 5 mol %, or from about 0.5 mol % to about 2 mol %, such as about 5 mol %, about 3 mol %, about 2 mol %, about 1 mol %, or about 0.5 mol %.

The quinone(s) and iron-based catalyst(s) may contain one or more chiral centers or may otherwise be capable of existing as multiple stereoisomers. These may be pure (single) stereoisomers or mixtures of stereoisomers, such as enantiomers, diastereomers, and enantiomerically or diastereomerically enriched mixtures. The quinone(s) may be capable of existing as geometric isomers. Accordingly, it is to be understood that the quinone(s) can be pure geometric isomers or mixtures of geometric isomers.

The iron-based catalysts and the ligands forming the iron-based catalysts described herein can be synthesized using methods known in the art of organic chemical synthesis. For example, the target Fe(II) complexes can be synthesized by reacting a corresponding ligand, optionally more than one corresponding ligand, with an iron precursor in a suitable solvent. Exemplary solvents include organic solvents, such as acetonitrile. The corresponding ligand(s) can be prepared using methods known in the art, such as those described in the Examples. The reaction solution containing the one or more corresponding ligands and the iron precursor can be stirred at a suitable temperature, such as room temperature and optionally under an inert gas atmosphere, such as nitrogen atmosphere, for a suitable time to form a product containing the target iron-based catalysts. The product containing the target iron-based catalysts can be purified and optionally recrystallized to isolate the target iron-based catalysts. More specific reagents, reaction conditions, and Fe(II) complexes formed are described in the Examples.

3. Products

Following step (i), a product containing one or more cis-diols converted from the quinones in the reaction mixture, is formed. In some forms, the product can also contain unreacted substrates, i.e. one or more unreacted quinones, and/or the iron-based catalysts.

In some forms, the product contains one or more cis-diols converted from one or more quinones of any of Formulae I-IV described above, the cis-diols can have the structure of Formula V or V' or a combination thereof, or Formula VI or VI' or a combination thereof:

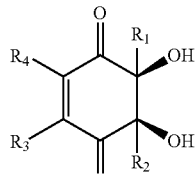

Formula V

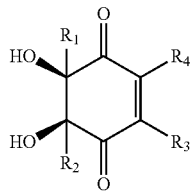

Formula V'

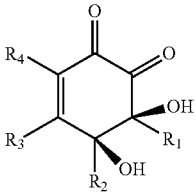

Formula VI

Formula VI'

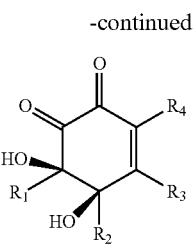

where: (a) $R_1$-$R_4$ can be independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (b) the substituents can be independently a substituted or unsubstituted alkyl (such as haloalkyl, e.g., —$CF_3$), a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

In some forms of Formulae V, V', VI, and VI', at least one of $R_1$-$R_4$, at least two of $R_1$-$R_4$, or at least three of $R_1$-$R_4$ can be an or are electron-donating group(s). In some forms of Formulae V, V', VI, and VI', at least one of $R_1$-$R_4$ can be hydrogen. In some forms of Formulae V, V', VI, and VI', at least one of $R_1$-$R_4$ can be an electron-donating group and at least one of $R_1$-$R_4$ can be hydrogen. In some forms of Formulae V, V', VI, and VI', $R_2$ can be hydrogen and $R_1$, $R_3$, and $R_4$ can be any of the groups as defined for Formulae I and II above. In some forms of Formulae V, V', VI, and VI', $R_3$ can be hydrogen and $R_1$, $R_2$, and $R_4$ can be any of the groups as defined for Formulae V, V', VI, and VI' above. In some forms of Formulae V, V', VI, and VI', $R_1$ and $R_2$ can be hydrogen and $R_3$ and $R_4$ can be any of the groups as defined for Formulae V, V', VI, and VI' above. In some forms of Formulae V, V', VI, and VI', $R_3$ and $R_4$ can be hydrogen and $R_1$ and $R_2$ can be any of the groups as defined for Formulae V, V', VI, and VI' above. In some forms of Formulae V, V', VI, and VI', at least $R_3$ is not hydrogen. In some forms of Formulae V and V', at least $R_3$ is not an electron-withdrawing group, such as halide, carbonyl, nitro, ammonium, trihalomethylsulfonyl, sulfonic acid, sulfonyl, cyano, trihalomethyl, haloformyl, aminocarbonyl, or nitroso.

In some forms of Formulae V, V', VI, and VI', $R_1$-$R_4$ can be independently a hydrogen, a substituted or unsubstituted alkyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic group, a substituted or unsubstituted aralkyl, an alkoxyl, or a carbonyl, or two neighboring R groups together with the carbon atoms to which they are attached can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group. In some forms of Formulae V, V', VI, and VI', $R_3$ and $R_4$ together with the carbon atoms to which they are attached can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

In some forms of Formulae V, V', VI, and VI', $R_1$-$R_4$ can be independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

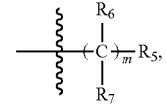

$R_5$ can be a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ can be independently a hydrogen or a substituted or unsubstituted alkyl, and m can be an integer from 1 to 10, from 1 to 8, from 1 to 6, from 1 to 3, or 1 or 2, or two neighboring R groups together with the carbon atoms to which they are attached can form a substituted or unsubstituted aryl or a substituted or unsubstituted polyaryl.

In some forms of Formulae V, V', VI, and VI', $R_1$-$R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

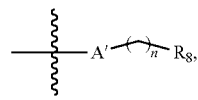

A' can be a single bond or an oxygen, $R_8$ is a substituted or unsubstituted phenyl, a substituted or unsubstituted cycloalkyl, or a substituted or unsubstituted heterocycloalkyl, and n can be an integer from 1 to 8, from 1 to 6, from 1 to 3, or 1 or 2, or two neighboring R groups together with the carbon atoms to which they are attached can form a substituted or unsubstituted aryl or a substituted or unsubstituted polyaryl.

In some forms, the cis-diol(s) contained in the product has the structure of Formula V or V' or a combination thereof as defined above. In some forms, the cis-diol contained in the product is not a cis-diol of 1,2-quinone. In some forms, the cis-diol contained in the product is not a cis-diol of 1,4-quinone.

In some forms, the cis-diol contained in the product can have the structure of Formula VII or VII' or a combination thereof:

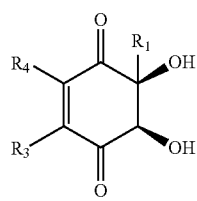

Formula VII

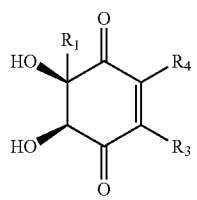

Formula VII' where $R_1$, $R_3$, and $R_4$ can be independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

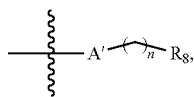

A' can be a single bond or an oxygen, $R_8$ can be a substituted or unsubstituted phenyl, a substituted or unsubstituted cycloalkyl, or a substituted or unsubstituted heterocycloalkyl, and n can be an integer from 1 to 8, from 1 to 6, from 1 to 3, or 1 or 2, or $R_3$ and $R_4$ together can form a substituted or unsubstituted aryl or a substituted or unsubstituted polyaryl, and the substituents can be as defined above for Formulae V and V'.

In some forms, the cis-diol contained in the product can have the structure of Formula VIII or VIII' or a combination thereof:

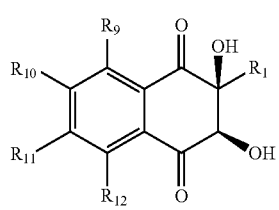

Formula VIII

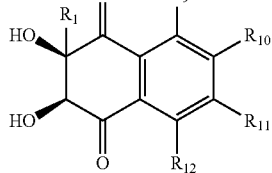

Formula VIII' where: (a) $R_1$ can be a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

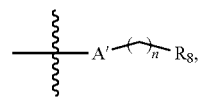

A' can be a single bond or an oxygen, $R_8$ can be a substituted or unsubstituted phenyl, a substituted or unsubstituted cycloalkyl, or a substituted or unsubstituted heterocycloalkyl, and n is an integer from 1 to 8, from 1 to 6, from 1 to 3, or 1 or 2; (b) $R_9$-$R_{12}$ can be independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached can form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (c) the substituents can be as defined above for Formulae V and V'.

In some forms of Formulae VIII and VIII', $R_9$-$R_{12}$ can be independently a hydrogen, a halide, a hydroxyl, an aroxy, an alkoxyl, or $R_{11}$ and $R_{12}$ together can form a substituted or unsubstituted cycloalkenyl, a substituted or unsubstituted polycycloalkenyl, a substituted or unsubstituted aryl or a substituted or unsubstituted polyaryl.

Exemplary cis-diols of the quinones formed from the AD reactions described herein are presented below.

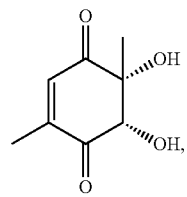

2a

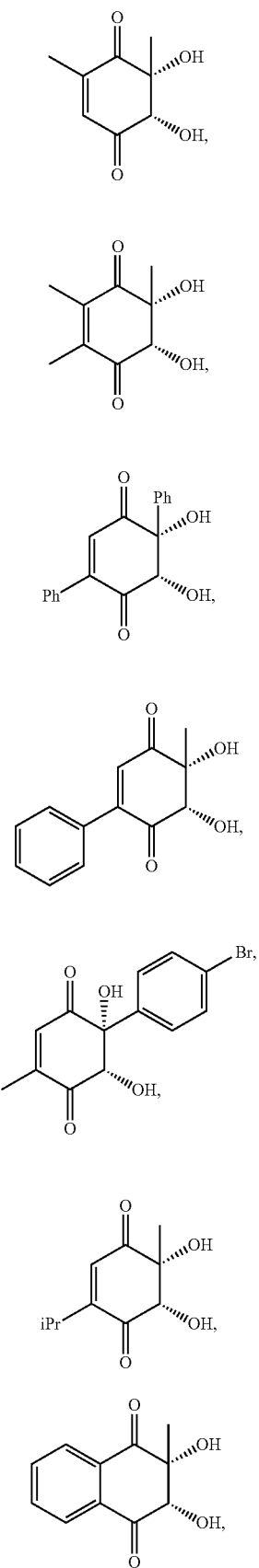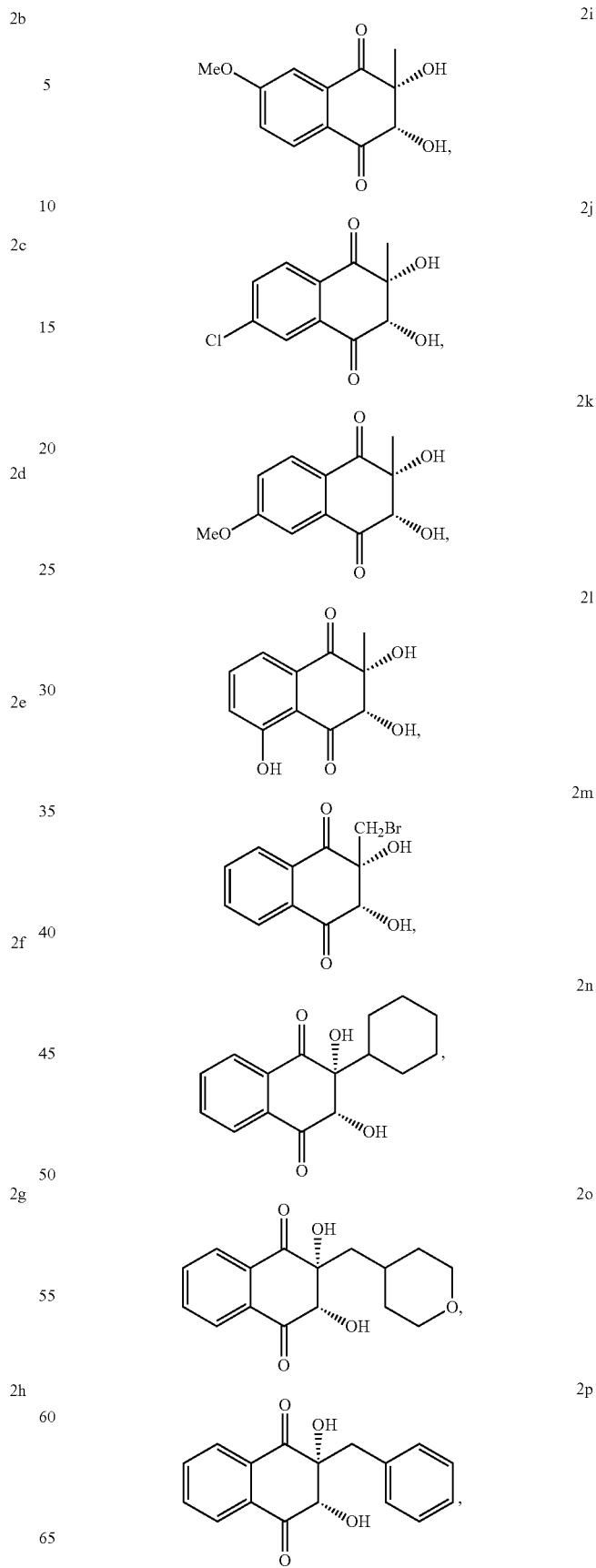

-continued

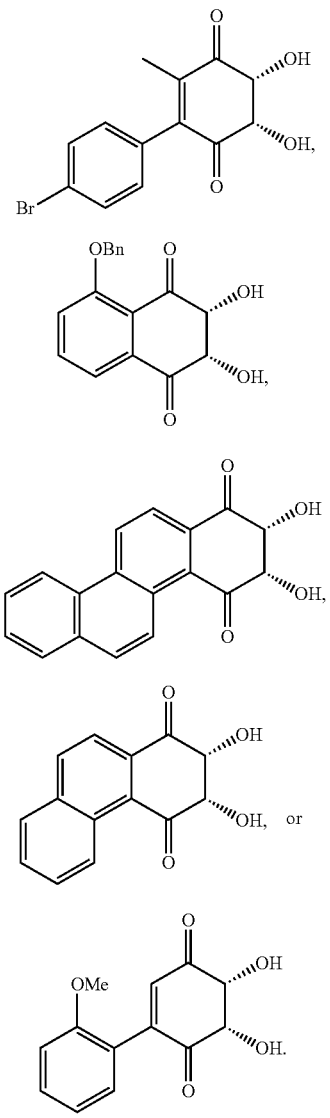

For any one of Formulae I-XI, V', VII', and VIII', the substituents can be independently a substituted or unsubstituted alkyl, a substituted or unsubstituted alkenyl, a substituted or unsubstituted alkynyl, a substituted or unsubstituted heterocyclyl, a substituted or unsubstituted aryl, a substituted or unsubstituted heteroaryl, a substituted or unsubstituted polyaryl, a substituted or unsubstituted polyheteroaryl, a substituted or unsubstituted aralkyl (e.g. benzyl), a carbonyl, an alkoxy (e.g. methoxy, ethoxy, aryloxy, benzoether, etc.), a halide, a hydroxyl, or a haloalkyl (e.g. —$CH_2Br$, —$CF_3$, etc.), or a combination thereof.

For any one of Formulae I-XI, V', VII', and VIII', the substituents can be independently an unsubstituted alkyl, an unsubstituted alkenyl, an unsubstituted alkynyl, an unsubstituted heterocyclyl, an unsubstituted aryl, a substituted aryl, an unsubstituted heteroaryl, an unsubstituted polyaryl, an unsubstituted polyheteroaryl, a substituted or unsubstituted aralkyl (e.g. benzyl), an alkoxy (e.g. methoxy, ethoxy, aryloxy, benzoether, etc.), a halide, a hydroxyl, or a haloalkyl (e.g. —$CH_2Br$, —$CF_3$, etc.), or a combination thereof.

For any one of Formulae I-XI, V', VII', and VIII', the substituents can be an unsubstituted alkyl (e.g. methyl, ethyl, propyl, butyl, pentyl, hexyl, etc.), an unsubstituted alkenyl (methylene, ethylene, propylene, butylene, pentylene, hexylene, etc.), an unsubstituted heterocyclyl, a substituted or unsubstituted phenyl, an unsubstituted polyaryl, a substituted or unsubstituted aralkyl (e.g. benzyl), an alkoxy (e.g. methoxy, ethoxy, aryloxy, benzoether, etc.), a halide, a hydroxyl, or a haloalkyl (e.g. —$CH_2Br$, —$CF_3$, etc.), or a combination thereof.

For any one of Formulae I-XI, V', VII', and VIII', the alkyl can be a linear alkyl, a branched alkyl, or a cyclic alkyl (either monocyclic or polycyclic). The terms "cyclic alkyl" and "cycloalkyl" are used interchangeably herein. Exemplary alkyl include a linear $C_1$-$C_{30}$ alkyl, a branched $C_4$-$C_{30}$ alkyl, a cyclic $C_3$-$C_{30}$ alkyl, a linear $C_1$-$C_{20}$ alkyl, a branched $C_4$-$C_{29}$ alkyl, a cyclic $C_3$-$C_{29}$ alkyl, a linear $C_1$-$C_{10}$ alkyl, a branched $C_4$-$C_{10}$ alkyl, a cyclic $C_3$-$C_{10}$ alkyl, a linear $C_1$-$C_6$ alkyl, a branched $C_4$-$C_6$ alkyl, a cyclic $C_3$-$C_6$ alkyl, a linear $C_1$-$C_4$ alkyl, cyclic $C_3$-$C_4$ alkyl, such as a linear $C_1$-$C_{10}$, $C_1$-$C_9$, $C_1$-$C_6$, $C_1$-05, $C_1$-$C_3$, or $C_1$-$C_2$ alkyl group, a branched $C_3$-$C_9$, $C_3$-$C_9$, $C_3$-$C_8$, $C_3$-$C_7$, $C_3$-$C_6$, $C_3$-05, or $C_3$-$C_4$ alkyl group, or a cyclic $C_3$-$C_9$, $C_3$-$C_9$, $C_3$-$C_8$, $C_3$-$C_7$, $C_3$-$C_6$, $C_3$-05, or $C_3$-$C_4$ alkyl group. The cyclic alkyl can be a monocyclic or polycyclic alkyl, such as a $C_4$-$C_{30}$, $C_4$-$C_{25}$, $C_4$-$C_{20}$, $C_4$-$C_{18}$, $C_4$-$C_{16}$, $C_4$-$C_{15}$, $C_4$-$C_{14}$, $C_4$-$C_{13}$, $C_4$-$C_{12}$, $C_4$-$C_{10}$, $C_4$-$C_9$, $C_4$-$C_8$, $C_4$-$C_7$, $C_4$-$C_6$, or $C_4$-$C_5$ monocyclic or polycyclic alkyl group.

For any one of Formulae I-XI, V', VII', and VIII', the alkenyl can be a linear alkenyl, a branched alkenyl, or a cyclic alkenyl (either monocyclic or polycyclic). The terms "cyclic alkenyl" and "cycloalkenyl" are used interchangeably herein. Exemplary alkenyl include a linear $C_2$-$C_{30}$ alkenyl, a branched $C_4$-$C_{30}$ alkenyl, a cyclic $C_3$-$C_{30}$ alkenyl, a linear $C_2$-$C_{20}$ alkenyl, a branched $C_4$-$C_{20}$ alkenyl, a cyclic $C_3$-$C_{20}$ alkenyl, a linear $C_2$-$C_{10}$ alkenyl, a branched $C_4$-$C_{10}$ alkenyl, a cyclic $C_3$-$C_{10}$ alkenyl, a linear $C_2$-$C_6$ alkenyl, a branched $C_4$-$C_6$ alkenyl, a cyclic $C_3$-$C_6$ alkenyl, a linear $C_2$-$C_4$ alkenyl, cyclic $C_3$-$C_4$ alkenyl, such as a linear $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$ alkenyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ alkenyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkenyl group. The cyclic alkenyl can be a monocyclic or polycyclic alkenyl, such as a $C_4$-$C_{30}$, $C_4$-$C_{25}$, $C_4$-$C_{20}$, $C_4$-$C_{18}$, $C_4$-$C_{16}$, $C_4$-Cis, $C_4$-$C_{14}$, $C_4$-$C_{13}$, $C_4$-$C_{12}$, $C_4$-$C_{10}$, $C_4$-$C_9$, $C_4$-$C_8$, $C_4$-$C_7$, $C_4$-$C_6$, or $C_4$-$C_5$ monocyclic or polycyclic alkenyl group.

For any one of Formulae I-XI, V', VII', and VIII', the alkynyl can be a linear alkynyl, a branched alkynyl, or a cyclic alkynyl (either monocyclic or polycyclic). The terms "cyclic alkynyl" and "cycloalkynyl" are used interchangeably herein. Exemplary alkynyl include a linear $C_2$-$C_{30}$ alkynyl, a branched $C_4$-$C_{30}$ alkynyl, a cyclic $C_3$-$C_{30}$ alkynyl, a linear $C_2$-$C_{20}$ alkynyl, a branched $C_4$-$C_{20}$ alkynyl, a cyclic $C_3$-$C_{20}$ alkynyl, a linear $C_2$-$C_{10}$ alkynyl, a branched $C_4$-$C_{10}$ alkynyl, a cyclic $C_3$-$C_{10}$ alkynyl, a linear $C_2$-$C_6$ alkynyl, a branched $C_4$-$C_6$ alkynyl, a cyclic $C_3$-$C_6$ alkynyl, a linear $C_1$-$C_4$ alkynyl, cyclic $C_3$-$C_4$ alkynyl, such as a linear $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$ alkynyl group, a branched $C_3$-$C_9$, $C_3$-$C_8$, $C_3$-$C_7$, $C_3$-$C_6$, $C_3$-$C_5$, $C_3$-$C_4$ alkynyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ alkynyl group. The cyclic alkynyl can be a monocyclic or polycyclic alkynyl, such as a $C_4$-$C_{30}$, $C_4$-$C_{25}$, $C_4$-$C_{20}$, $C_4$-Cis, $C_4$-$C_{16}$, $C_4$-$C_{15}$, $C_4$-$C_{14}$, $C_4$-$C_{13}$, $C_4$-$C_{12}$, $C_4$-$C_{10}$, $C_4$-$C_9$, $C_4$-$C_8$, $C_4$-$C_7$, $C_4$-$C_6$, or $C_4$-$C_5$ monocyclic or polycyclic alkynyl group.

It is understood that any of the exemplary alkyl, alkenyl, and alkynyl groups can be heteroalkyl, heteroalkenyl, and heteroalkynyl, respectively. For example, the alkyl can be a linear $C_2$-$C_{30}$ heteroalkyl, a branched $C_4$-$C_{30}$ heteroalkyl, a cyclic $C_3$-$C_{30}$ heteroalkyl (i.e. a monocycloheteroalkyl or polycycloheteroalkyl), a linear $C_1$-$C_{20}$ heteroalkyl, a branched $C_4$-$C_{20}$ heteroalkyl, a cyclic $C_3$-$C_{20}$ heteroalkyl, a linear $C_1$-$C_{10}$ heteroalkyl, a branched $C_4$-$C_{10}$ heteroalkyl, a cyclic $C_3$-$C_{10}$ heteroalkyl, a linear $C_1$-$C_6$ heteroalkyl, a branched $C_4$-$C_6$ heteroalkyl, a cyclic $C_3$-$C_6$ heteroalkyl, a linear $C_1$-$C_4$ heteroalkyl, cyclic $C_3$-$C_4$ heteroalkyl, such as a linear $C_1$-$C_{10}$, $C_1$-$C_9$, $C_1$-$C_8$, $C_1$-$C_6$, $C_1$-$C_5$, $C_1$-$C_4$, $C_1$-$C_3$, $C_1$-$C_2$ heteroalkyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkyl group. The cyclic heteroalkyl can be monocyclic or polycyclic, such as a $C_4$-$C_{30}$, $C_4$-$C_{25}$, $C_4$-$C_{20}$, $C_4$-$C_{18}$, $C_4$-$C_{16}$, $C_4$-$C_{15}$, $C_4$-$C_{14}$, $C_4$-$C_{13}$, $C_4$-$C_{12}$, $C_4$-$C_{10}$, $C_4$-$C_9$, $C_4$-$C_8$, $C_4$-$C_7$, $C_4$-$C_6$, or $C_4$-$C_5$ monocyclic or polycyclic heteroalkyl group.

For any one of Formulae I-XI, V', VII', and VIII', the alkenyl can be a linear $C_2$-$C_{30}$ heteroalkenyl, a branched $C_4$-$C_{30}$ heteroalkenyl, a cyclic $C_3$-$C_{30}$ heteroalkenyl (i.e. a monocycloheteroalkenyl or polycycloheteroalkenyl), a linear $C_1$-$C_{20}$ heteroalkenyl, a branched $C_4$-$C_{20}$ heteroalkenyl, a cyclic $C_3$-$C_{20}$ heteroalkenyl, a linear $C_1$-$C_{10}$ heteroalkenyl, a branched $C_4$-$C_{10}$ heteroalkenyl, a cyclic $C_3$-$C_{10}$ heteroalkenyl, a linear $C_2$-$C_6$ heteroalkenyl, a branched $C_4$-$C_6$ heteroalkenyl, a cyclic $C_3$-$C_6$ heteroalkenyl, a linear $C_2$-$C_4$ heteroalkenyl, cyclic $C_3$-$C_4$ heteroalkenyl, such as a linear $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$ heteroalkenyl group, a branched $C_3$-$C_9$, $C_3$-$C_9$, $C_3$-$C_8$, $C_3$-$C_7$, $C_3$-$C_6$, $C_3$-$C_5$, $C_3$-$C_4$ heteroalkenyl group, or a cyclic $C_3$-$C_9$, $C_3$-$C_9$, $C_3$-$C_8$, $C_3$-$C_7$, $C_3$-$C_6$, $C_3$-$C_5$, $C_3$-$C_4$ heteroalkenyl group. The cyclic heteroalkenyl can be monocyclic or polycyclic, such as a $C_4$-$C_{30}$, $C_4$-$C_{25}$, $C_4$-$C_{20}$, $C_4$-$C_{18}$, $C_4$-$C_{16}$, $C_4$-$C_{15}$, $C_4$-$C_{14}$, $C_4$-$C_{13}$, $C_4$-$C_{12}$, $C_4$-$C_{10}$, $C_4$-$C_9$, $C_4$-$C_8$, $C_4$-$C_7$, $C_4$-$C_6$, or $C_4$-$C_5$ monocyclic or polycyclic heteroalkenyl group.

For any one of Formulae I-XI, V', VII', and VIII', the alkynyl can be a linear $C_2$-$C_{30}$ heteroalkynyl, a branched $C_4$-$C_{30}$ heteroalkynyl, a cyclic $C_3$-$C_{30}$ heteroalkynyl (i.e. a monocycloheteroalkynyl or polycycloheteroalkynyl), a linear $C_2$-$C_{20}$ heteroalkynyl, a branched $C_4$-$C_{20}$ heteroalkynyl, a cyclic $C_3$-$C_{20}$ heteroalkynyl, a linear $C_2$-$C_{10}$ heteroalkynyl, a branched $C_4$-$C_{10}$ heteroalkynyl, a cyclic $C_3$-$C_{10}$ heteroalkynyl, a linear $C_2$-$C_6$ heteroalkynyl, a branched $C_4$-$C_6$ heteroalkynyl, a cyclic $C_3$-$C_6$ heteroalkynyl, a linear $C_2$-$C_4$ heteroalkynyl, cyclic $C_3$-$C_4$ heteroalkynyl, such as a linear $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$ heteroalkynyl group, a branched $C_3$-$C_9$, $C_3$-$C_8$, $C_3$-$C_7$, $C_3$-$C_6$, $C_3$-05, $C_3$-$C_4$ heteroalkynyl group, or a cyclic $C_3$-$C_9$, $C_3$-$C_9$, $C_3$-$C_8$, $C_3$-$C_7$, $C_3$-$C_6$, $C_3$-05, $C_3$-$C_4$ heteroalkynyl group. The cyclic heteroalkynyl can be monocyclic or polycyclic, such as a $C_4$-$C_{30}$, $C_4$-$C_{25}$, $C_4$-$C_{20}$, $C_4$-$C_{18}$, $C_4$-$C_{16}$, $C_4$-$C_{15}$, $C_4$-$C_{14}$, $C_4$-$C_{13}$, $C_4$-$C_{12}$, $C_4$-$C_{10}$, $C_4$-$C_9$, $C_4$-$C_8$, $C_4$-$C_7$, $C_4$-$C_6$, or $C_4$-$C_5$ monocyclic or polycyclic heteroalkynyl group.

For any one of Formulae I-XI, V', VII', and VIII', the aryl group can be a $C_5$-$C_{30}$ aryl, a $C_5$-$C_{20}$ aryl, a $C_5$-$C_{12}$ aryl, a $C_5$-$C_{11}$ aryl, a $C_5$-$C_9$ aryl, a $C_6$-$C_{20}$ aryl, a $C_6$-$C_{12}$ aryl, a $C_6$-$C_{11}$ aryl, or a $C_6$-$C_9$ aryl. It is understood that the aryl can be a heteroaryl, such as a $C_5$-$C_{30}$ heteroaryl, a $C_5$-$C_{20}$ heteroaryl, a $C_5$-$C_{12}$ heteroaryl, a $C_5$-$C_{11}$ heteroaryl, a $C_5$-$C_9$ heteroaryl, a $C_6$-$C_{30}$ heteroaryl, a $C_6$-$C_{20}$ heteroaryl, a $C_6$-$C_{12}$ heteroaryl, a $C_6$-$C_{11}$ heteroaryl, or a $C_6$-$C_9$ heteroaryl. For any of Formulae I-IV, the polyaryl group can be a $C_{10}$-$C_{30}$ polyaryl, a $C_{10}$-$C_{20}$ polyaryl, a $C_{10}$-$C_{12}$ polyaryl, a $C_{10}$-$C_{11}$ polyaryl, or a $C_{12}$-$C_{20}$ polyaryl. It is understood that the aryl can be a polyheteroaryl, such as a $C_{10}$-$C_{30}$ polyheteroaryl, a $C_{10}$-$C_{20}$ polyheteroaryl, a $C_{10}$-$C_{12}$ polyheteroaryl, a $C_{10}$-$C_{11}$ polyheteroaryl, or a $C_{12}$-$C_{20}$ polyheteroaryl.

4. Characterization of AD Reactions

The disclosed methods for asymmetric cis-dihydroxylation of quinone(s) can be characterized by substrate conversion, cis-diol yield, and enantiomeric excess ("ee") of cis-diol in the product.

a. Substrate Conversion

Generally, following AD reaction using the disclosed methods, the substrates (i.e. the quinone(s)) can have a total conversion of at least 20%, at least 40%, at least 50%, at least 65%, at least 70%, at least 80%, at least 90%, in a range from about 20% to 100%, from about 40% to 100%, from about 50% to 100%, from about 65% to 100%, from about 70% to 100%, from about 80% to 100%, or from about 90% to 100%. The total conversion of the substrate(s) can be calculated by the formula: conversion (%)={1−(the sum of the no. of moles of the substrate(s) in the reaction mixture after the designated reaction time)/(the sum of the no. of moles of the substrate(s) added in the reaction mixture)}× 100%. Methods for measuring the no. of moles of the substrate(s) in the reaction mixture and/or product are known, such as $^1$H NMR, Mass Spectrometry, Gas Chromatography, etc. For example, the no. of moles of the substrate(s) in the reaction mixture and/or the unreacted substrate(s) in the product is measured using $^1$H NMR.

In some forms, following AD reaction catalyzed by one or more iron-based catalysts of Formulae IX-XI using the disclosed methods, the one or more quinones of any of Formulae I-IV or any of Formulae I, III, and IV, has a total conversion of at least 20%, at least 40%, at least 50%, at least 65%, at least 70%, at least 80%, at least 90%, in a range from about 20% to 100%, from about 40% to 100%, from about 50% to 100%, from about 65% to 100%, from about 70% to 100%, from about 80% to 100%, or from about 90% to 100%.

In some forms, following AD reaction catalyzed by one or more iron-based catalysts of Formula X or XII using the disclosed methods, the one or more quinones of any of Formulae I-IV or any of Formulae I, III, and IV has a total conversion of at least 20%, at least 40%, at least 50%, at least 65%, at least 70%, at least 80%, at least 90%, in a range from about 20% to 100%, from about 40% to 100%, from about 50% to 100%, from about 65% to 100%, from about 70% to 100%, from about 80% to 100%, or from about 90% to 100%.

In some forms, following AD reaction catalyzed by one or more iron-based catalysts of Formula XIII, XIV, and/or XV using the disclosed methods, the one or more quinones of any of Formulae I-IV or any of Formulae I, III, and IV has a total conversion of at least 20%, at least 40%, at least 50%, at least 65%, at least 70%, at least 80%, at least 90%, in a range from about 20% to 100%, from about 40% to 100%, from about 50% to 100%, from about 65% to 100%, from about 70% to 100%, from about 80% to 100%, or from about 90% to 100%.

In some forms, following AD reaction catalyzed by $Fe^{II}$(L1)(OTf)$_2$, $Fe^{II}$(L4)(OTf)$_2$, and/or $Fe^{II}$(L5)(OTf)$_2$ using the disclosed methods, the one or more quinones of any of Formulae I-IV or any of Formulae I, III, and IV has a total conversion of at least 50%, in a range from about 50% to 100%, such as 100%. For example, following AD reaction catalyzed by $Fe^{II}$(L4)(OTf)$_2$ and/or $Fe^{II}$(L5)(OTf)$_2$ using the disclosed methods, the one or more quinones of any of Formulae I-IV or any of Formulae I, III, and IV has a total conversion rate of at least 60%, at least 70%, at least 80%, at least 90%, in a range from about 60% to 100%, from about 70% to 100%, from about 80% to 100%, or from about 90% to 100%.

In some forms, following AD reaction catalyzed by catalyst $Fe^{II}(L_9)(OTf)_2$ shown above using the disclosed methods, the one or more quinones of any of Formulae I-IV or any of Formulae I, III, and IV has a total conversion of at least 80%, in a range from about 80% to 100%, such as 100%. For example, following AD reaction catalyzed by catalyst $Fe^{II}(L_9)(OTf)_2$ using the disclosed methods, the one or more quinones of any of Formulae I-IV or any of Formulae I, III, and IV has a total conversion rate of at least 80%, at least 90%, in a range from about 80% to 100% or from about 90% to 100%.

b. Cis-Diol Yield

Generally, the cis-diol(s) in the product formed from the AD reactions using the disclosed methods can have a total yield of at least 30%, at least 40%, at least 50%, in a range from about 30% to about 99%, from about 40% to about 99%, from about 50% to about 99%, from about 60% to about 99%, from about 70% to about 99%, or from about 80% to about 99%. The yield of cis-diol(s) in the product can be calculated using the formula: cis-diol yield=(experimentally obtained total no. of mole of cis-diol(s))/(theoretical total no. of mole of cis-diol(s))×100%. The experimentally obtained total no. of mole of the cis-diol(s) can be determined using known methods, such as using NMR (e.g. $^1H$ NMR, $^{19}F$ NMR, and/or $^{31}P$ NMR) spectroscopy with an internal standard of known quantity, such as using a known quantity of PhTMS as the internal standard.

In some forms, the cis-diol(s) of any of Formulae V-VIII, V', VII', and VIII' in the product formed from the AD reactions catalyzed by one or more iron-based catalysts of Formulae IX-XI using the disclosed methods can have a total yield of at least 30%, at least 40%, at least 50%, in a range from about 30% to about 99%, from about 40% to about 99%, from about 50% to about 99%, from about 60% to about 99%, from about 70% to about 99%, or from about 80% to about 99%.

In some forms, the cis-diol(s) of any of Formulae V, V', VII, VII', VIII, and VIII' in the product formed from the AD reactions catalyzed by one or more iron-based catalysts of Formulae IX-XI using the disclosed methods can have a total yield of at least 30%, at least 40%, at least 50%, in a range from about 30% to about 99%, from about 40% to about 99%, from about 50% to about 99%, from about 60% to about 99%, from about 70% to about 99%, or from about 80% to about 99%.

In some forms, the cis-diol(s) of any of Formulae V, V', VII, VII', VIII, and VIII' in the product formed from the AD reactions catalyzed by one or more iron-based catalysts of Formula X or XII using the disclosed methods can have a total yield of at least 30%, at least 40%, at least 50%, in a range from about 30% to about 99%, from about 40% to about 99%, from about 50% to about 99%, from about 60% to about 99%, from about 70% to about 99%, or from about 80% to about 99%.

In some forms, the cis-diol(s) of any of Formulae V, V', VII, VII', VIII, and VIII' in the product formed from the AD reactions catalyzed by one or more iron-based catalysts of Formula XIII, XIV, and/or XV using the disclosed methods can have a total yield of at least 70%, at least 75%, at least 80%, in a range from about 70% to about 99%, from about 75% to about 99%, from about 80% to about 99%, or from about 85% to about 99%.

In some forms, the cis-diol(s) of Formula VII and/or Formula VII' in the product formed from the AD reactions catalyzed by one or more iron-based catalysts of Formula X or XII using the disclosed methods can have a total yield of at least 50%, in a range from about 50% to about 99%, from about 60% to about 99%, from about 70% to about 99%, or from about 80% to about 99%. In some forms, the cis-diol(s) of Formula VIII and/or Formula VIII' in the product formed from the AD reactions catalyzed by one or more iron-based catalysts of Formula X or XII using the disclosed methods can have a total yield of at least 50%, in a range from about 30% to about 99%, from about 40% to about 99%, from about 50% to about 99%, from about 60% to about 99%, from about 70% to about 99%, or from about 80% to about 99%.

In some forms, the cis-diol(s) of Formula VII and/or Formula VII' in the product formed from the AD reactions catalyzed by one or more iron-based catalysts of Formula XIII, XIV, and/or XV using the disclosed methods can have a total yield of at least 75% or in a range from about 75% to about 99%. In some forms, the cis-diol(s) of Formula VIII and/or Formula VIII' in the product formed from the AD reactions catalyzed by one or more iron-based catalysts of Formula XIII, XIV, and/or XV using the disclosed methods can have a total yield of at least 70%, in a range from about 70% to about 99%, from about 80% to about 99%, or from about 90% to about 99%.

In some forms, the cis-diol(s) of Formula VII and/or Formula VII' in the product formed from the AD reactions catalyzed by $Fe^{II}(L4)(OTf)_2$ using the disclosed methods can have a total yield of at least 50%, in a range from about 50% to about 99%, from about 60% to about 99%, from about 70% to about 99%, or from about 80% to about 99%. In some forms, the cis-diol(s) of Formula VIII and/or Formula VIII' in the product formed from the AD reactions catalyzed by $Fe^{II}(L4)(OTf)_2$ using the disclosed methods can have a total yield of at least 50%, in a range from about 30% to about 99%, from about 40% to about 99%, from about 50% to about 99%, from about 60% to about 99%, from about 70% to about 99%, or from about 80% to about 99%.

In some forms, the cis-diol(s) of Formula VII and/or Formula VII' in the product formed from the AD reactions catalyzed by catalyst $Fe^{II}(L9)(OTf)_2$ using the disclosed methods can have a total yield of at least 75% or in a range from about 75% to about 99%.

In some forms, the cis-diol(s) of Formula VIII and/or Formula VIII' in the product formed from the AD reactions catalyzed by catalyst $Fe^{II}(L9)(OTf)_2$ using the disclosed methods can have a total yield of at least 70%, in a range from about 70% to about 99%, from about 80% to about 99%, or from about 90% to about 99%.

In some forms, the cis-diol(s) in the product formed from the AD reactions using the disclosed methods can have a total yield of at least 4-time, at least 4.5-time, at least 5-time, or at least 5.5-time higher than the yield of the same cis-diol(s) formed from the same reaction, using the same amount or a higher amount of $OsO_4$ or AD-mix-α/β compared to the total amount of the iron-based catalyst. The amount of $OsO_4$ or AD-mix-α/β in the reaction mixture for catalyzing AD reaction of quinone(s) can be calculated by the formula: mol % of the $OsO_4$ or AD-mix-α/β=[(no. of mole of $OsO_4$ or AD-mix-α/(3)/(the sum of the nos. of moles of the one or more quinone(s))]×100%.

For example, the cis-diol(s) of any of Formulae V, V', VII, VII', VIII, and VIII' in the product formed from the AD reactions using the disclosed methods can have a total yield that is at least 4-time, at least 4.5-time, at least 5-time, or at least 5.5-time higher than the yield of the same cis-diol(s)

formed from the same reaction, using the same amount or a higher amount of $OsO_4$ or AD-mix-α/β compared to the total amount of the iron-based catalyst.

In some forms, AD reactions of quinones using $OsO_4$ and/or AD-mix-α/β cannot produce any cis-diol, even at a higher temperature, a longer period of times, and/or a higher amount of $OsO_4$ and/or AD-mix-α/β compared to the disclosed methods.

Specific exemplary cis-diol(s) and their corresponding yields, and the yield of the same cis-diol(s) formed from the AD reaction using known catalysts, such as $OsO_4$ or AD-mix-α/β, are described in Example 3 below.

c. Enantiomeric Excess

Generally, the cis-diol or each cis-diol of two or more cis-diols in the product formed from the AD reactions using the disclosed methods can have an enantiomeric excess ("ee") of at least 30%, at least 40%, at least 50%, at least 60%, up to 100%, in a range from about 35% to 100%, from about 60% to 100%, from about 70% to 100%, from about 80% to 100%, from about 90% to 100%, or from about 95% to 100%. The ee of cis-diol(s) in the product can be calculated using the formula: ee=[(moles of enantiomer−moles of another enantiomer)/total moles of both enantiomers]×100%. The ee of each cis-diol can be determined using known methods, such as using chiral HPLC or a polarimeter. In some forms, the ee of each cis-diol can be determined using chiral HPLC.

In some forms, each cis-diol of any of Formulae V-VIII, V', VII', and VIII' in the product formed from the AD reactions catalyzed by one or more iron-based catalysts of Formulae IX-XI using the disclosed methods can have an ee of at least 30%, at least 40%, at least 50%, at least 60%, up to 100%, in a range from about 35% to 100%, from about 60% to 100%, from about 70% to 100%, from about 80% to 100%, from about 90% to 100%, or from about 95% to 100%.

In some forms, each cis-diol of any of Formulae V, V', VII, VII', VIII, and VIII' in the product formed from the AD reactions catalyzed by one or more iron-based catalysts of Formulae IX-XI using the disclosed methods can have an ee of at least 30%, at least 40%, at least 50%, at least 60%, up to 100%, in a range from about 35% to 100%, from about 60% to 100%, from about 70% to 100%, from about 80% to 100%, from about 90% to 100%, or from about 95% to 100%.

In some forms, each cis-diol of any of Formulae V, V', VII, VII', VIII, and VIII' in the product formed from the AD reactions catalyzed by one or more iron-based catalysts of Formula X or XII using the disclosed methods can have an ee of at least 30%, at least 40%, at least 50%, at least 60%, up to 100%, in a range from about 35% to 100%, from about 60% to 100%, from about 70% to 100%, from about 80% to 100%, from about 90% to 100%, or from about 95% to 100%.

In some forms, each cis-diol of any of Formulae V, V', VII, VII', VIII, and VIII' in the product formed from the AD reactions catalyzed by one or more iron-based catalysts of Formula XIII, XIV, and/or XV using the disclosed methods can have an ee of at least 80%, at least 85%, at least 90%, in a range from about 80% to 100%, from about 80% to 96%, from about 85% to 100%, from about 90% to 100%, or from about 95% to 100%.

In some forms, each cis-diol of Formula VII and/or Formula VII' in the product formed from the AD reactions catalyzed by one or more iron-based catalysts of Formula X or XII using the disclosed methods can have an ee of at least 80%, in a range from about 80% to 100%, from about 85% to 100%, from about 90% to 100%, or from about 95% to 100%. In some forms, each cis-diol of Formula VIII and/or Formula VIII' in the product formed from the AD reactions catalyzed by one or more iron-based catalysts of Formula X or XII using the disclosed methods can have an ee of at least 60%, in a range from about 60% to about 98%, from about 65% to about 98%, from about 75% to about 98%, from about 85% to about 98%, or from about 90% to about 98%.

In some forms, each cis-diol of Formula VII and/or Formula VII' in the product formed from the AD reactions catalyzed by one or more iron-based catalysts of Formula XIII, XIV, and/or XV using the disclosed methods can have an ee of at least 80%, in a range from about 80% to 98% or from about 90% to 98%. In some forms, each cis-diol of Formula VIII and/or Formula VIII' in the product formed from the AD reactions catalyzed by one or more iron-based catalysts of Formula XIII, XIV, and/or XV using the disclosed methods can have an ee of at least 85%, at least 90%, in a range from about 85% to about 100%, from about 85% to about 98%, from about 90% to about 100%, from about 90% to about 98%, or from about 90% to about 96%.

In some forms, each cis-diol of Formula VII and/or Formula VII' in the product formed from the AD reactions catalyzed by $Fe^{II}(L4)(OTf)_2$ using the disclosed methods can have an ee of at least 80%, in a range from about 80% to 100%, from about 85% to 100%, from about 90% to 100%, or from about 95% to 100%. In some forms, each cis-diol of Formula VIII and/or Formula VIII' in the product formed from the AD reactions catalyzed by $Fe^{II}(L4)(OTf)_2$ using the disclosed methods can have an ee of at least 60%, in a range from about 60% to about 98%, from about 65% to about 98%, from about 75% to about 98%, from about 85% to about 98%, or from about 90% to about 98%.

In some forms, each cis-diol of Formula VII and/or Formula VII' in the product formed from the AD reactions catalyzed by catalyst $Fe^{II}(L9)(OTf)_2$ using the disclosed methods can have an ee of at least 80%, in a range from about 80% to 98% or from about 90% to 98%. In some forms, each cis-diol of Formula VIII and/or Formula VIII' in the product formed from the AD reactions catalyzed by catalyst $Fe^{II}(L9)(OTf)_2$ using the disclosed methods can have an ee of at least 85%, at least 90%, in a range from about 85% to about 100%, from about 85% to about 98%, from about 90% to about 100%, from about 90% to about 98%, or from about 90% to about 96%.

In some forms, the cis-diol or each cis-diol of two or more cis-diols in the product formed from the AD reactions using the disclosed methods can have an ee that is at least 3-time, at least 3.5-time, at least 4-time, at least 5-time, or at least 5.5-time higher than the ee of the same cis-diol formed from the same reaction, using the same amount or a higher amount of $OsO_4$ or AD-mix-α/β compared to the total amount of the iron-based catalyst.

For example, the cis-diol or each cis-diol of two or more cis-diols of any of Formulae V, V', VII, VII', VIII, and VIII' in the product formed from the AD reactions using the disclosed methods can have an ee that is at least 3-time, at least 3.5-time, at least 4-time, at least 5-time, or at least 5.5-time higher than the ee of the same cis-diol formed from the same reaction, using the same amount or a higher amount of $OsO_4$ or AD-mix-α/β compared to the total amount of the iron-based catalyst.

Specific exemplary cis-diol(s) and their corresponding ee, and the ee of the same cis-diol(s) formed from the AD reaction using known catalysts, such as $OsO_4$ or AD-mix-α/β, are described in Example 3 below.

B. Optional Steps

The disclosed methods can include one or more optional steps, such as adding an oxidant (e.g. a hydrogen peroxide solution) into the reaction mixture prior to and/or during step (i); stirring the reaction mixture prior to and/or during step (i); and/or purifying the product, optionally by column chromatography, subsequent to step (i).

1. Adding an Oxidant

Optionally, the disclosed method includes a step of adding an oxidant into the reaction mixture prior to and/or during step (i), maintaining the reaction mixture at a temperature for a period of time sufficient to form a product containing cis-diol(s). Without being bound to any theory, it is believed that the oxidant participates in the oxidation of the C=C and thereby improves the yield of the cis-diol(s) compared with reactions without the oxidant. For example, the addition of the oxidant in the reaction mixture increases the cis-diol yield in the product by at least 2%, at least 5%, at least 10%, or at least 20% compared to the same reaction without the oxidant.

An exemplary oxidant suitable for use in the disclosed methods is hydrogen peroxide solution. When the oxidant is in the form of a solution, the solvent for forming the solution of oxidant can be the same or different from the solvent forming the reaction mixture. For example, the hydrogen peroxide solution is formed by mixing hydrogen peroxide with a solvent that is the same as the solvent forming the reaction mixture, such as an alcohol (e.g. methanol, ethanol, propanol, etc.) or acetonitrile, or a combination thereof.

The oxidant, such as a hydrogen peroxide solution, can be added into the reaction mixture by depressing a syringe filled with the oxidant in a solution form in a swift action. Alternatively, the oxidant, such as a hydrogen peroxide solution, can be added into the reaction mixture by a syringe pump at a suitable flow rate over a period of time. For example, the oxidant, such as a hydrogen peroxide solution, is injected into the reaction mixture by a syringe in a swift action or added into the reaction mixture by a syringe pump over 30 mins.

Generally, following the addition step, the total mole amount of the oxidant, such as a hydrogen peroxide solution, in the reaction mixture can be in a range from about 1-time to about 10-time, from about 1.5-time to about 6-time, or from about 2-time to about 5-time of the total mole amount of the one or more quinone(s). For example, following addition of a hydrogen peroxide solution into the reaction mixture (either by a swift injection or addition over a period of time), the total no. of moles of the oxidant in the reaction mixture is in a range from about 1-time to about 10-time, from about 1.5-time to about 6-time, or from about 2-time to about 5-time, such as about 3-time, of the total mole amount of the one or more quinone(s) in the reaction mixture.

2. Stirring the Reaction Mixture

Optionally, the reaction mixture is under stirring prior to and/or during step (i), maintaining the reaction mixture at a temperature for a period of time sufficient to form a product containing cis-diol(s). For example, the reaction mixture is stirred at the reaction temperature during the entire reaction period to form the product containing cis-diol(s). Techniques for stirring the reaction mixture during reaction are known, such as by using a mechanical stirring bar, magnetic stirring beads, etc.

3. Purifying the Product

Optionally, the disclosed method includes a step of purifying the product to remove impurities, such as unreacted substrates and/or the catalysts, in the product, and thereby obtain isolated cis-diol(s), subsequent to the AD reaction (i.e. step (i)). The product can be purified by known methods, such as using column chromatography on silica gel or recrystallization in a dichloromethane/hexane mixture.

The disclosed substrates, iron-based catalysts, products, and methods can be further understood through the following enumerated paragraphs.

1. A method for asymmetric cis-dihydroxylation of a quinone comprising:
   (i) maintaining a reaction mixture at a temperature for a period of time sufficient to form a product,
   wherein the reaction mixture comprises the quinone, one or more iron-based catalyst(s), and a solvent, and
   wherein the product comprises a cis-diol.

2. The method of paragraph 1 further comprising adding an oxidant into the reaction mixture prior to and/or during step (i), optionally the oxidant is a hydrogen peroxide solution.

3. The method of paragraph 2, wherein the total mole amount of the oxidant in the reaction mixture is in a range from about 1-time to about 10-time, from about 1.5-time to about 6-time, or from about 2-time to about 5-time of the total mole amount of the quinone.

4. The method of paragraph 1, wherein the quinone has a structure of:

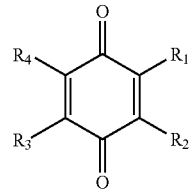

Formula I wherein:
(a) $R_1$-$R_4$ are independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (b) the substituents are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

5. The method of paragraph 4, wherein at least one of $R_1$-$R_4$, at least two of $R_1$-$R_4$, or at least three of $R_1$-$R_4$ is an or are electron-donating group(s).

6. The method of paragraph 4 or 5, wherein at least one of $R_1$-$R_4$ is hydrogen.

7. The method of any one of paragraphs 4-6, wherein $R_1$-$R_4$ are independently a hydrogen, a substituted or unsubstituted alkyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic group, a substituted or unsubstituted aralkyl, an alkoxyl, or a carbonyl, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

8. The method of any one of paragraphs 4-7, wherein $R_1$-$R_4$ are independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

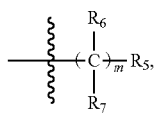

$R_5$ is a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ are independently a hydrogen or a substituted or unsubstituted alkyl, and m is an integer from 1 to 10, or two neighboring R groups together with the carbon atoms to which are attached form a substituted or unsubstituted aryl or a substituted or unsubstituted polyaryl.

9. The method of any one of paragraphs 4-8, wherein $R_1$-$R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

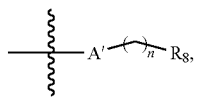

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or two neighboring R groups together with the carbon atoms to which they are attached form a substituted or unsubstituted aryl or a substituted or unsubstituted polyaryl.

10. The method of any one of paragraphs 4-9, wherein the quinone has a structure of:

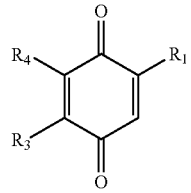

Formula III wherein $R_1$, $R_3$, and $R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

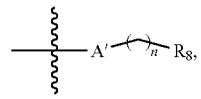

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or $R_3$ and $R_4$ together with the carbon atoms to which they are attached form a substituted or unsubstituted aryl or a substituted or unsubstituted polyaryl.

11. The method of any one of paragraphs 4-10, wherein the quinone has a structure of:

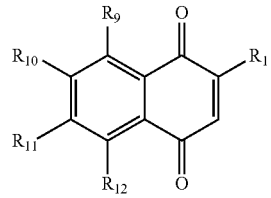

Formula IV wherein:
(a) $R_1$ is a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

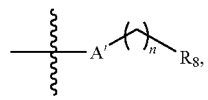

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8; and
(b) $R_9$-$R_{12}$ are independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

12. The method of paragraph 11, wherein $R_9$-$R_{12}$ are independently a hydrogen, a halide, a hydroxyl, an aroxy, an alkoxyl, or $R_{11}$ and $R_{12}$ together with the carbon atoms to which they are attached form a substituted or unsubstituted cycloalkenyl, a substituted or unsubstituted polycycloalkenyl, a substituted or unsubstituted aryl or a substituted or unsubstituted polyaryl.

13. The method of any one of paragraphs 4-12, wherein the quinone has a structure of:

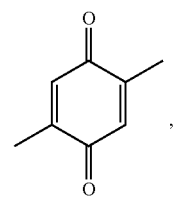
1a

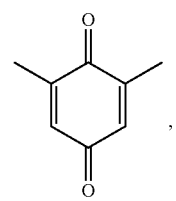
1b

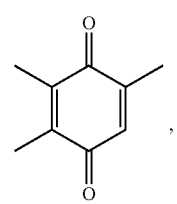
1c

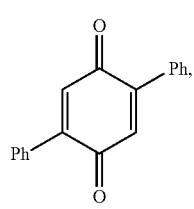
1d

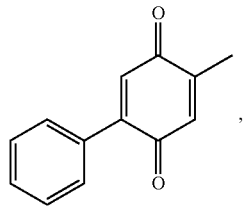
1e

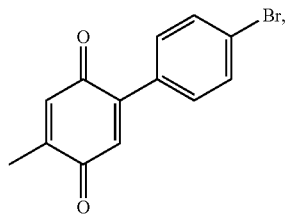
1f

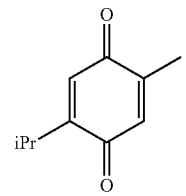
1g

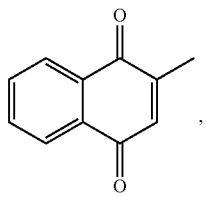
1h

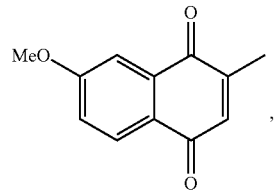
1i

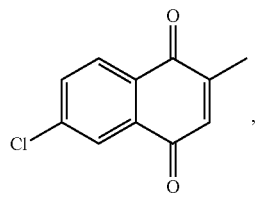
1j

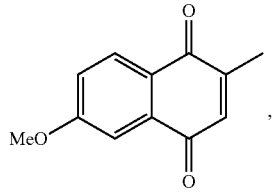
1k

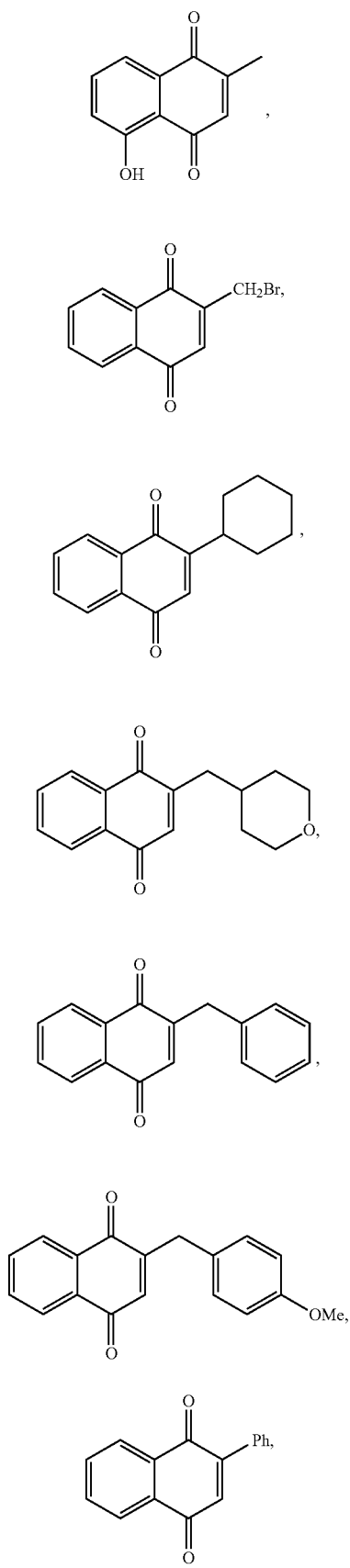
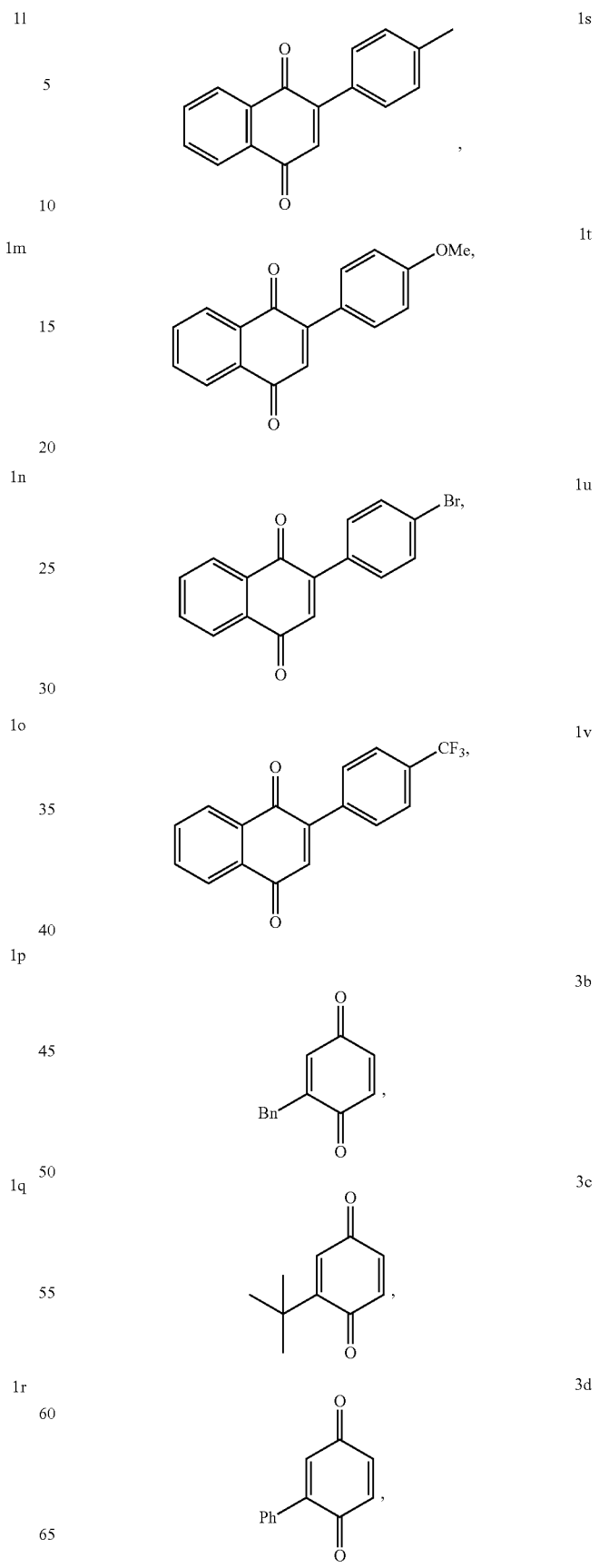

-continued

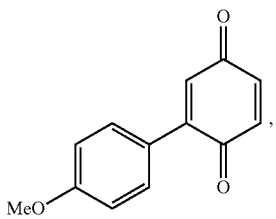
3e

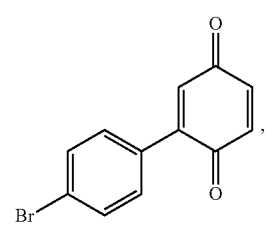
3f

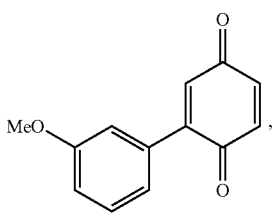
3g

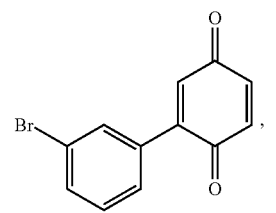
3h

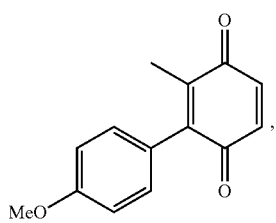
3i

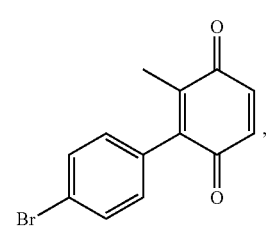
3j

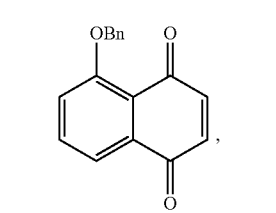
3k

-continued

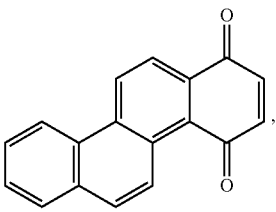
3l

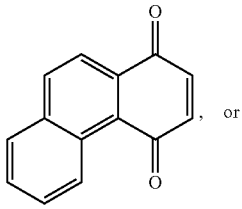
, or
3m

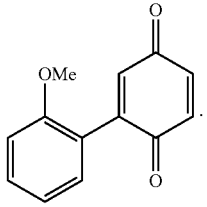
.
3n

14. The method of any one of paragraphs 1-4, wherein the cis-diol has a structure of:

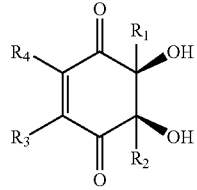
Formula V wherein:
(a) $R_1$-$R_4$ are independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and
(b) the substituents are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

15. The method of paragraph 14, wherein $R_1$-$R_4$ are independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

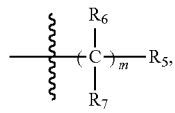

$R_5$ is a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ are independently a hydrogen or a substituted or unsubstituted alkyl, and m is an integer from 1 to 10, or two neighboring R groups together with the carbon atoms to which they are attached form a substituted or unsubstituted aryl or a substituted or unsubstituted polyaryl.

16. The method of paragraph 14 or 15, wherein $R_1$-$R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

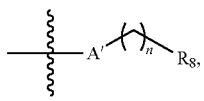

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or two neighboring R groups together with the carbon atoms to which they are attached form a substituted or unsubstituted aryl or a substituted or unsubstituted polyaryl.

17. The method of any one of paragraphs 14-16, wherein the cis-diol has a structure of:

Formula VII

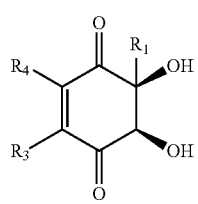

wherein $R_1$, $R_3$, and $R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

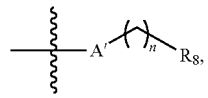

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or $R_3$ and $R_4$ together with the carbon atoms to which they are attached form a substituted or unsubstituted aryl or a substituted or unsubstituted polyaryl.

18. The method of any one of paragraphs 14-17, wherein the cis-diol has a structure of:

Formula VIII

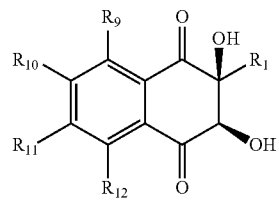

wherein:
(a) $R_1$ is a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

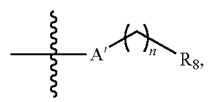

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8; and (b) $R_9$-$R_{12}$ are independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

19. The method of paragraph 18, wherein $R_9$-$R_{12}$ are independently a hydrogen, a halide, a hydroxyl, an aroxy, an alkoxyl, or $R_{11}$ and $R_{12}$ together with the carbon atoms to which they are attached form a substituted or unsubstituted cycloalkenyl, a substituted or unsubstituted polycycloalkenyl, a substituted or unsubstituted aryl or a substituted or unsubstituted polyaryl.

20. The method of any one of paragraphs 14-19, wherein the cis-diol has a structure of:

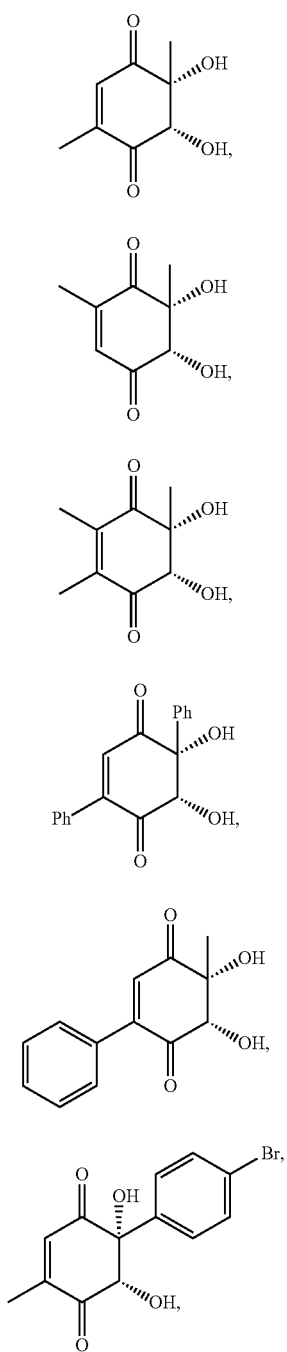

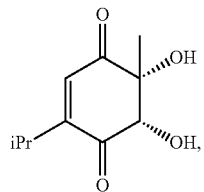

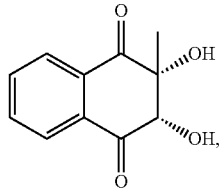

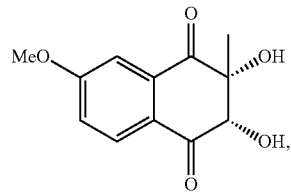

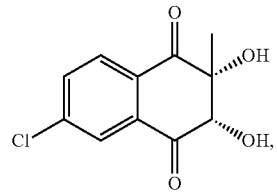

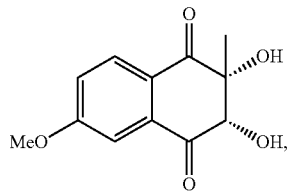

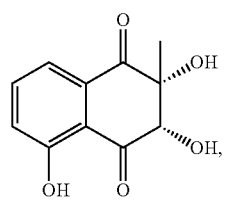

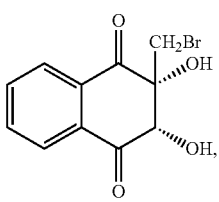

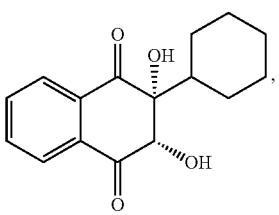

-continued
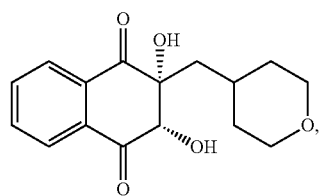
2o
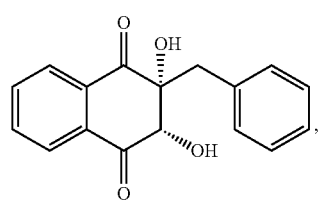
2p
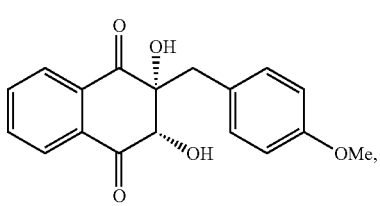
2q
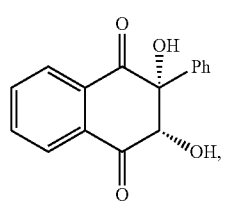
2r
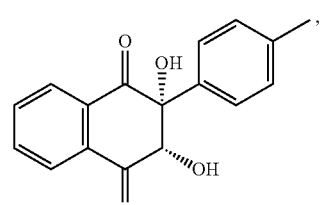
2s
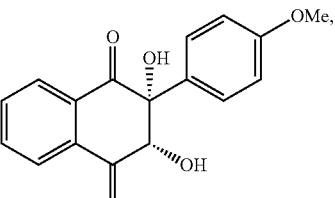
2t
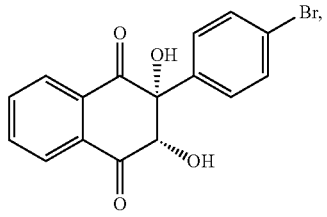
2u
-continued
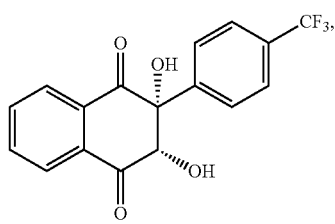
2v
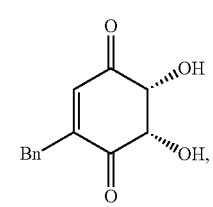
4b
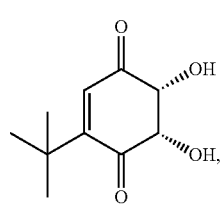
4c
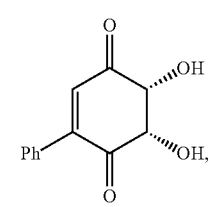
4d
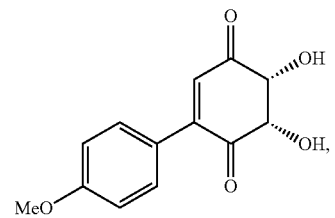
4e
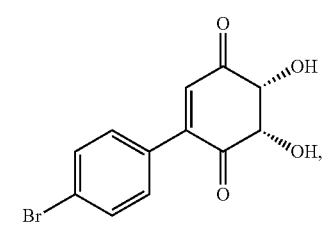
4f
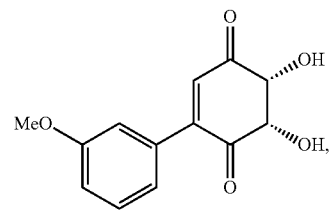
4g -continued

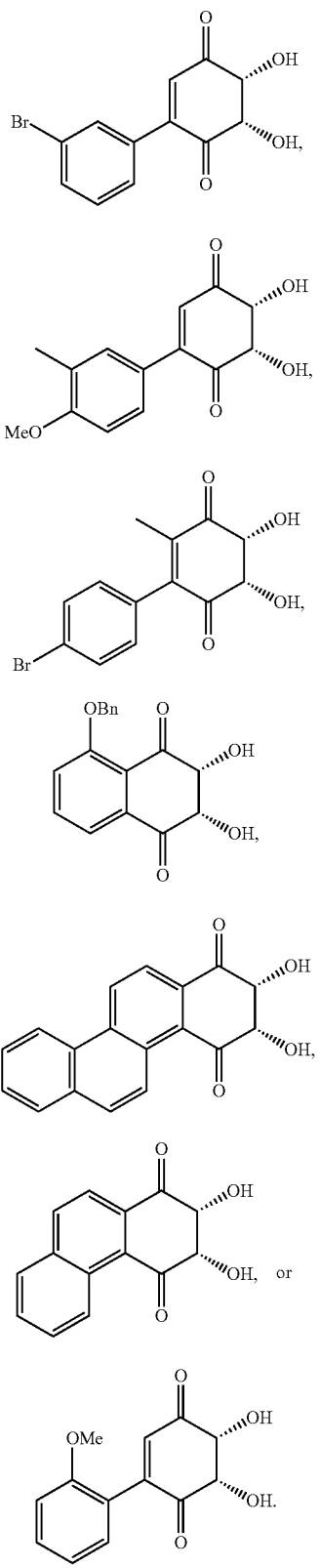

21. The method of any one of paragraphs 1-20, wherein each of the one or more iron-based catalyst(s) has a structure of:

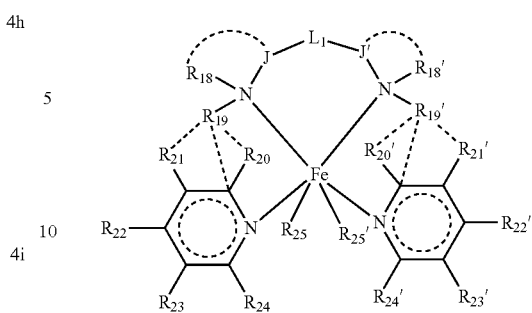

Formula IX wherein:
(a) J and J' are independently a bond (single, double, or triple), a substituted or unsubstituted alkyl, a substituted or unsubstituted alkenyl, a substituted or unsubstituted cyclic group, a substituted or unsubstituted aryl, or a substituted or unsubstituted polyaryl;
(b) $L_1$ is a bond or

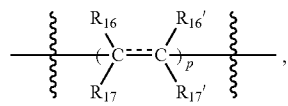

$R_{16}$, $R_{16}'$, $R_{17}$, and $R_{17}'$ are independently a hydrogen, a substituted or unsubstituted alkyl, a substituted or unsubstituted alkenyl, a substituted or unsubstituted aryl, a substituted or unsubstituted polyaryl, or a substituted or unsubstituted cyclic group, or $R_{16}$ and $R_{16}'$ together and/or $R_{17}$ and $R_{17}'$ together, with the carbon atoms to which they are attached, form a substituted or unsubstituted aryl, a substituted or unsubstituted polyaryl, or a substituted or unsubstituted cyclic group, and p is an integer from 1 to 10;
(c) $R_{18}$-$R_{24}$ and $R_{18}'$-$R_{24}'$ are independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl;
(d) $R_{25}$ and $R_{25}'$ are independently a leaving group;
(e) ----- is absent or a bond (single, double, or triple); and
(f) the substituents are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

22. The method of paragraph 21, wherein $R_{19}$, $R_{20}$, and $R_{21}$ together and/or $R_{19}'$, $R_{20}'$, and $R_{21}'$ together, with the carbon atoms to which they are attached, form a substituted or unsubstituted aryl, a substituted or unsubstituted polyaryl, or a substituted or unsubstituted cyclic group.

23. The method of paragraph 21 or 22, wherein each of the one or more iron-based catalyst(s) has a structure of:

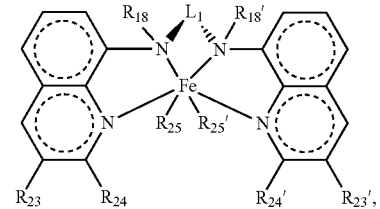

Formula X

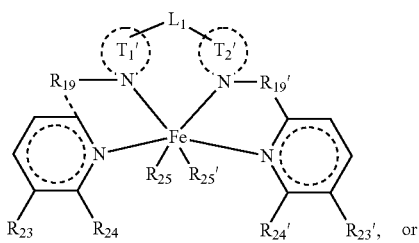

Formula XI

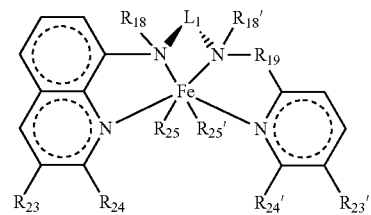

Formula XIII wherein:
(a) $L_1$ is a bond or

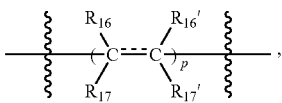

$R_{16}$, $R_{16}'$, $R_{17}$, and $R_{17}'$ are independently a hydrogen, a substituted or unsubstituted alkyl, a substituted or unsubstituted alkenyl, a substituted or unsubstituted aryl, a substituted or unsubstituted polyaryl, or a substituted or unsubstituted cyclic group, or $R_{16}$ and $R_{16}'$ together and/or $R_{17}$ and $R_{17}'$ together, with the carbon atoms to which they are attached, form a substituted or unsubstituted aryl, a substituted or unsubstituted polyaryl, or a substituted or unsubstituted cyclic group, and p is an integer from 1 to 10;
(b) $T_1'$ and $T_2'$ are independently a substituted or unsubstituted heteroaryl, a substituted or unsubstituted heteropolyaryl, or a substituted or unsubstituted heterocyclic group;
(c) $R_{18}$, $R_{19}$, $R_{23}$, $R_{24}$, $R_{18}'$, $R_{19}'$, $R_{23}'$, and $R_{24}'$ are independently a hydrogen, a substituted or unsubstituted alkyl, a substituted or unsubstituted alkenyl, or a substituted or unsubstituted aryl;
(d) $R_{25}$ and $R_{25}'$ are independently a leaving group; and
(e) the substituents are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

24. The method of any one of paragraphs 21-23, wherein $L_1$ is

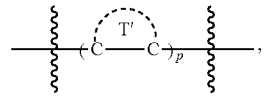

each occurrence of T' is a substituted or unsubstituted monocyclic group or a substituted or unsubstituted polycyclic group and p is an integer from 1 to 3.

25. The method of any one of paragraphs 21-24, wherein $R_{25}$ and $R_{25}'$ are independently a triflate, a tosylate, a mesylate, a halide, a nitrate, a phosphate, a thioether, an amino, a carboxylate, a phenoxide, an alkoxyl, or an amido.

26. The method of any one of paragraphs 21-25, wherein the catalyst has a structure of:

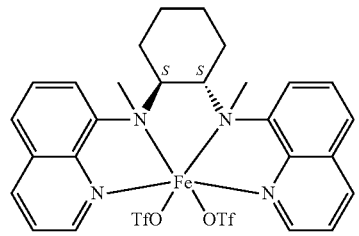

$Fe^{II}(L1)(OTf)_2$

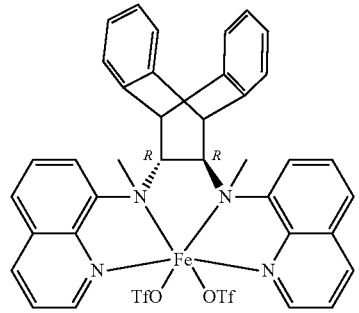

$[Fe^{II}(L2)(OTf)_2]$

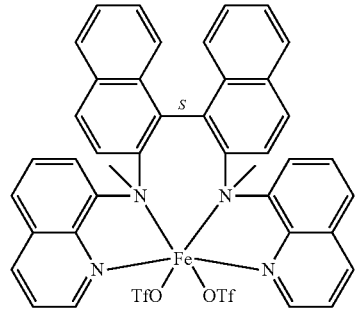

$Fe^{II}(L3)(OTf)_2$

-continued

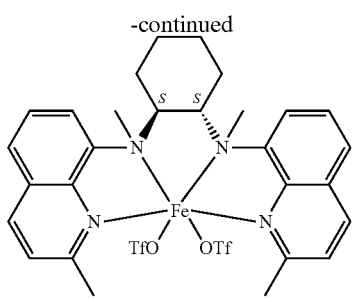

Fe<sup>II</sup>(L4)(OTf)<sub>2</sub>

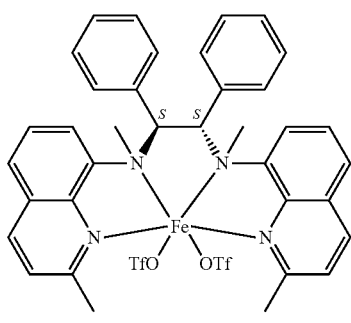

Fe<sup>II</sup>(L5)(OTf)<sub>2</sub>

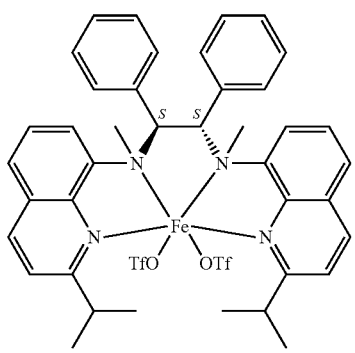

Fe<sup>II</sup>(L6)(OTf)<sub>2</sub>

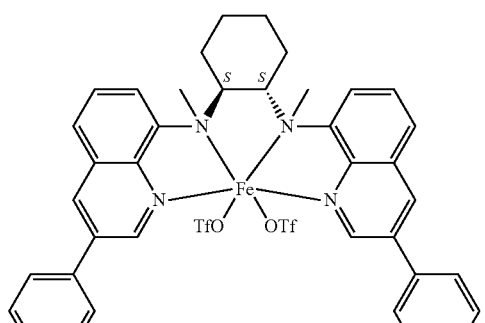

Fe<sup>II</sup>(L7)(OTf)<sub>2</sub>

-continued

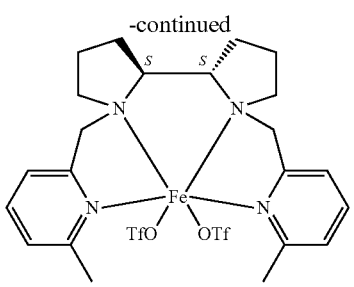

Fe<sup>II</sup>(L8)(OTf)<sub>2</sub>

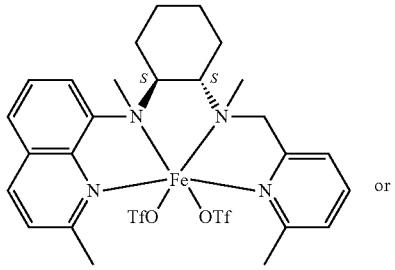

Fe<sup>II</sup>(L9)(OTf)<sub>2</sub> or

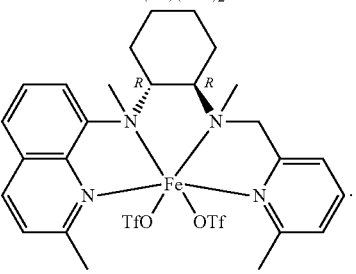

Fe<sup>II</sup>(L9-R)(OTf)<sub>2</sub>

27. The method of any one of paragraphs 1-26, wherein the total amount of the one or more iron-based catalyst(s) in the reaction mixture is up to 10 mol %, up to 5 mol %, up to 3 mol %, at least 0.1 mol %, at least 0.5 mol %, in a range from about 0.1 mol % to about 10 mol %, from about 0.1 mol % to about 5 mol %, from about 0.1 mol % to about 3 mol %, from about 0.5 mol % to about 10 mol %, from about 0.5 mol % to about 5 mol %, from about 0.5 mol % to about 3 mol %, from about 1 mol % to about 10 mol %, from about 1 mol % to about 5 mol %, or from about 0.5 mol % to about 2 mol %.

28. The method of any one of paragraphs 1-27, wherein the solvent is an alcohol, optionally a $C_1$-$C_6$ alcohol, or acetonitrile, or a combination thereof.

29. The method of any one of paragraphs 1-28, wherein the reaction mixture is maintained at room temperature for a period of time in a range from about 20 minutes to about 3 hours, from about 30 minutes to about 2 hours, or from about 30 minutes to 1 hour.

30. The method of any one of paragraphs 1-29 further comprising adding one or more additive(s) into the reaction mixture prior to and/or during step (i), stirring the reaction mixture prior to and/or during step (i), and/or purifying the product, optionally by column chromatography, subsequent to step (i).

31. The method of any one of paragraphs 1-30, wherein the cis-diol has a yield of at least 30%, at least 40%, at least 50%, in a range from about 30% to about 99%, from about 40% to about 99%, from about 50% to about 99%, from about 60% to about 99%, from about 70% to about 99%, or from about 80% to about 99%.

32. The method of any one of paragraphs 1-31, wherein the cis-diol has an enantiometric excess of at least 30%, at least 40%, at least 50%, at least 60%, up to 100%, in a range from about 35% to 100%, from about 60% to 100%, from about 70% to 100%, from about 80% to 100%, from about 90% to 100%, or from about 95% to 100%, as determined by chiral HPLC.

33. The method of any one of paragraphs 1-32, wherein the cis-diol has a yield that is at least 4-time, at least 4.5-time, at least 5-time, or at least 5.5-time higher than the yield of the same cis-diol(s) formed from the same reaction, using the same amount or a higher amount of $OsO_4$ or AD-mix-α/β compared to the total amount of the iron-based catalyst.

34. The method of any one of paragraphs 1-12, wherein the cis-diol has an enantiometric excess that is at least 3-time, at least 3.5-time, at least 4-time, at least 5-time, or at least 5.5-time higher than the enantiometric excess of the same cis-diol formed from the same reaction, using the same loading or a higher loading of $OsO_4$ or AD-mix-α/β compared to the total amount of the iron-based catalyst.

35. An iron(II) complex having the structure:

Formula XII

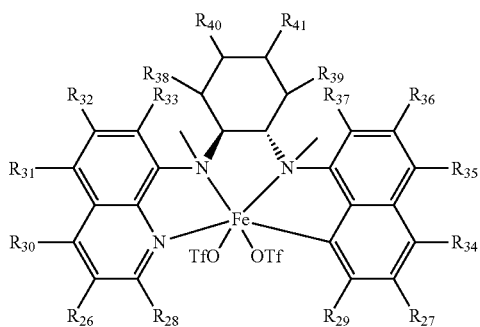

wherein:
(a) $R_{26}$ and $R_{27}$ are independently a substituted or unsubstituted cyclic group, a substituted or unsubstituted aryl, or a substituted or unsubstituted polyaryl;
(b) $R_{28}$-$R_{41}$ are independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl; and
(c) the substituents are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

36. The iron complex of paragraph 35, wherein (a) $R_{26}$ and $R_{27}$ are independently a substituted or unsubstituted aryl or a substituted or unsubstituted polyaryl; (b) $R_{28}$-$R_{41}$ are independently a hydrogen, a substituted or unsubstituted alkyl, or a substituted or unsubstituted alkenyl; and (c) the substituents are independently a substituted or unsubstituted alkyl, a substituted or unsubstituted alkenyl, or a substituted or unsubstituted alkynyl, or a combination thereof.

37. The iron complex of paragraph 35 or 36, wherein (a) $R_{26}$ and $R_{27}$ are independently a substituted or unsubstituted aryl; (b) $R_{28}$-$R_{41}$ are independently a hydrogen, an unsubstituted alkyl, or an unsubstituted alkenyl; and (c) the substituents are independently an unsubstituted alkyl, an unsubstituted alkenyl, an unsubstituted alkynyl, or a combination thereof.

38. The iron complex of any one of paragraphs 35-37 having the structure:

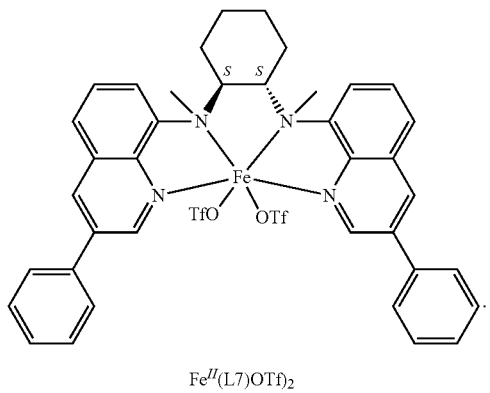

$Fe^{II}(L7)OTf_2$

39. An iron(II) complex having the structure:

Formula XIV

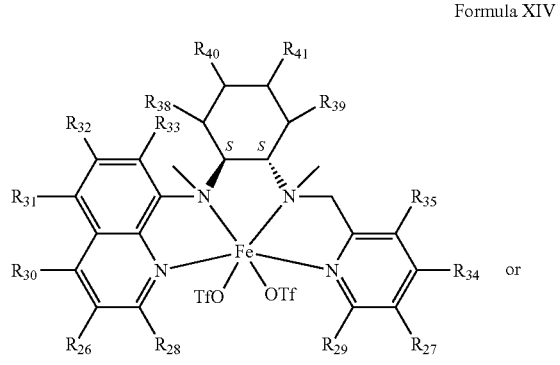

or

Formula XV

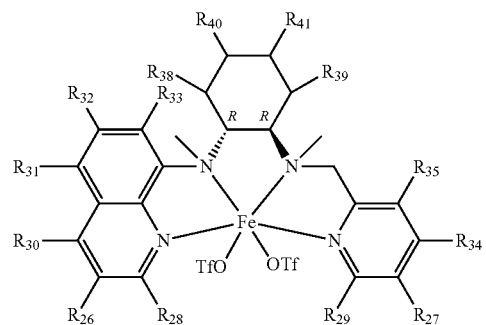

wherein:
(a) $R_{26}$ and $R_{27}$ are independently hydrogen, a substituted or unsubstituted cyclic group, a substituted or unsubstituted aryl, or a substituted or unsubstituted polyaryl;
(b) $R_{28}$-$R_{41}$ are independently a hydrogen, a substituted or unsubstituted alkyl, a substituted or unsubstituted alkenyl, a substituted or unsubstituted cyclic group, a substituted or unsubstituted aryl, or a substituted or unsubstituted polyaryl; and
(c) the substituents are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, an carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

40. The iron complex of paragraph 39, wherein (a) $R_{26}$ and $R_{27}$ are hydrogen; (b) $R_{28}$ and $R_{29}$ are independently a substituted or unsubstituted alkyl, a substituted or unsubstituted alkenyl, or a substituted or unsubstituted aryl; (c) $R_{30}$-$R_{35}$ and $R_{38}$-$R_{41}$ are independently a hydrogen, a substituted or unsubstituted alkyl, or a substituted or unsubstituted alkenyl; and (c) the substituents are independently a substituted or unsubstituted alkyl, a substituted or unsubstituted alkenyl, or a substituted or unsubstituted alkynyl, or a combination thereof.

41. The iron complex of paragraph 39 or 40, wherein (a) $R_{26}$, $R_{27}$, $R_{30}$-$R_{35}$, and $R_{38}$-$R_{41}$ are hydrogen; and (b) $R_{28}$ and $R_{29}$ are independently an unsubstituted alkyl.

42. The iron complex of any one of paragraphs 39-41 having the structure:

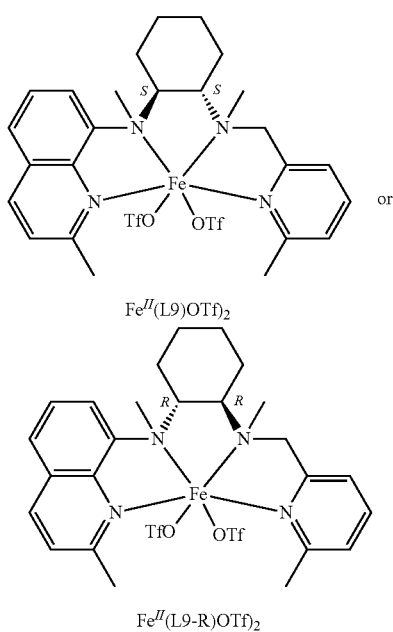

The present invention will be further understood by reference to the following non-limiting examples.

EXAMPLES

Example 1. Exemplary Fe(II) Complexes Catalyze Asymmetric Cis-Dihydroxylation of Quinone Materials and Methods Materials and Instruments Reagents were obtained commercially and used without further purification. Solvents were dried according to literature. Molecular sieves were dried at 450° C. for 12 h prior to use. Reactions were monitored by thin layer chromatography (TLC) visualizing with ultraviolet light (UV), $KMnO_4$, and phosphomolybdic acid (PMA) stain; column chromatography purifications were carried out using Merck silica gel 60. Proton nuclear magnetic resonance ($^1$H NMR) spectra were recorded on a 400 or 500 MHz spectrometer in $CDCl_3$, $CD_3OD$, and DMSO-$d_6$, and carbon nuclear magnetic resonance ($^{13}$C NMR) spectra were recorded on 125 MHz spectrometer in $CDCl_3$, $CD_3OD$, and DMSO-$d_6$. Chemical shifts (δ ppm) were determined with tetramethylsilane (TMS) as internal reference. High performance liquid chromatography was carried out using Agilent 1100 equipped with a variable wavelength detector on chiral stationary columns from DAICEL. Mass spectra were determined on a Finnigan MAT 95 mass spectrometer.

Synthesis of Iron Complexes

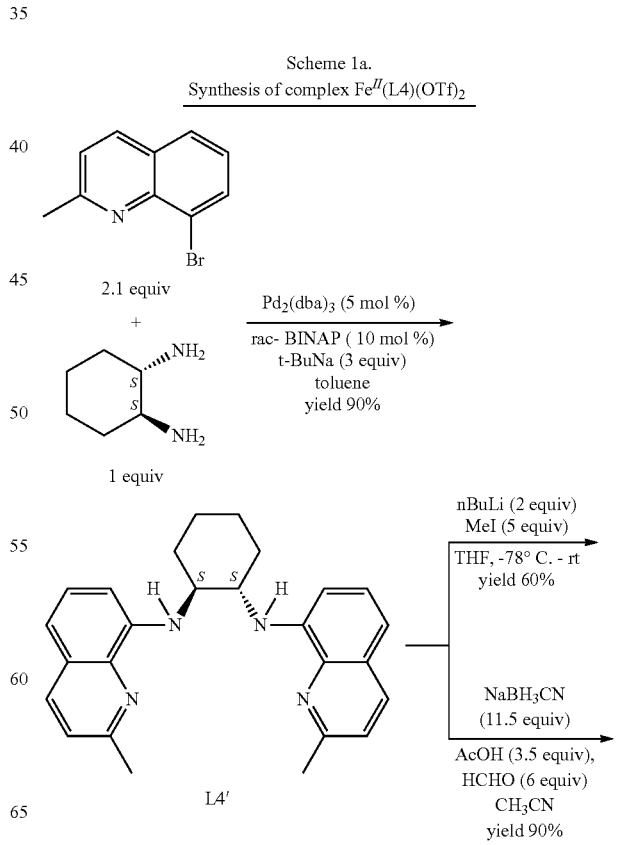

105
-continued
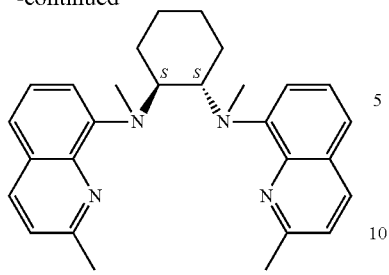
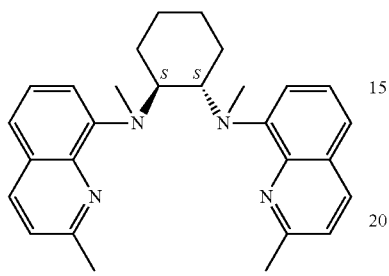
L4
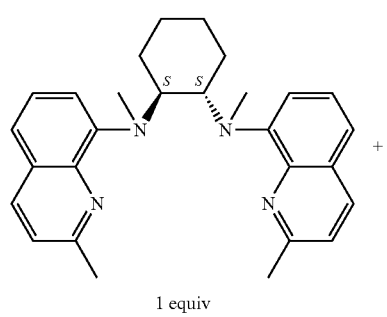
1 equiv
Fe(OTf)$_2$(CH$_3$CN)$_2$   THF
1 equiv              overnight
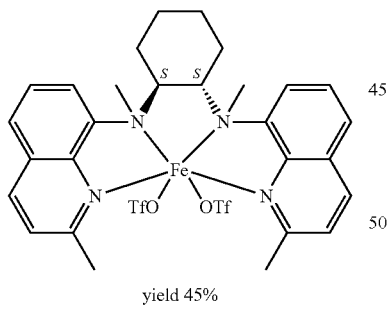
yield 45%
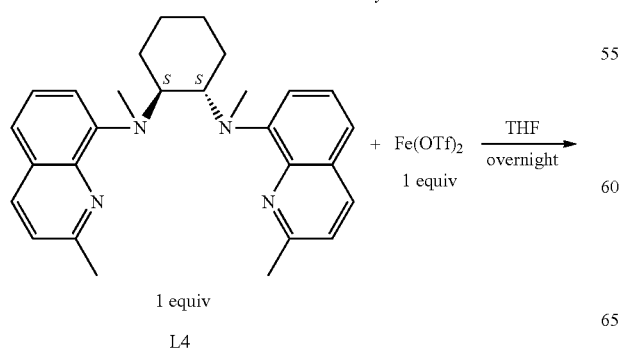
1 equiv
L4
106
-continued
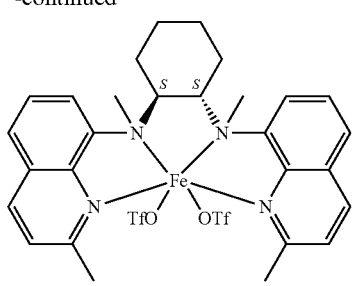
yield 85%
Fe$^{II}$(L4)(OTf)$_2$
Scheme 1b.
Synthesis of complex Fe$^{II}$(L7)(OTf)$_2$
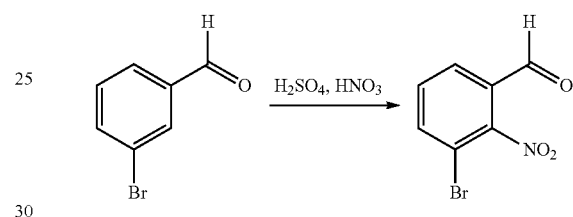
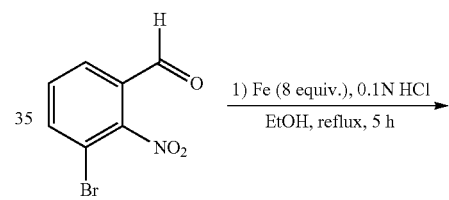
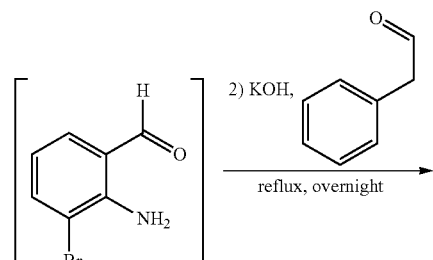
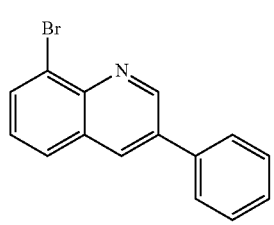
Quinoline A
Overall yield: 91%

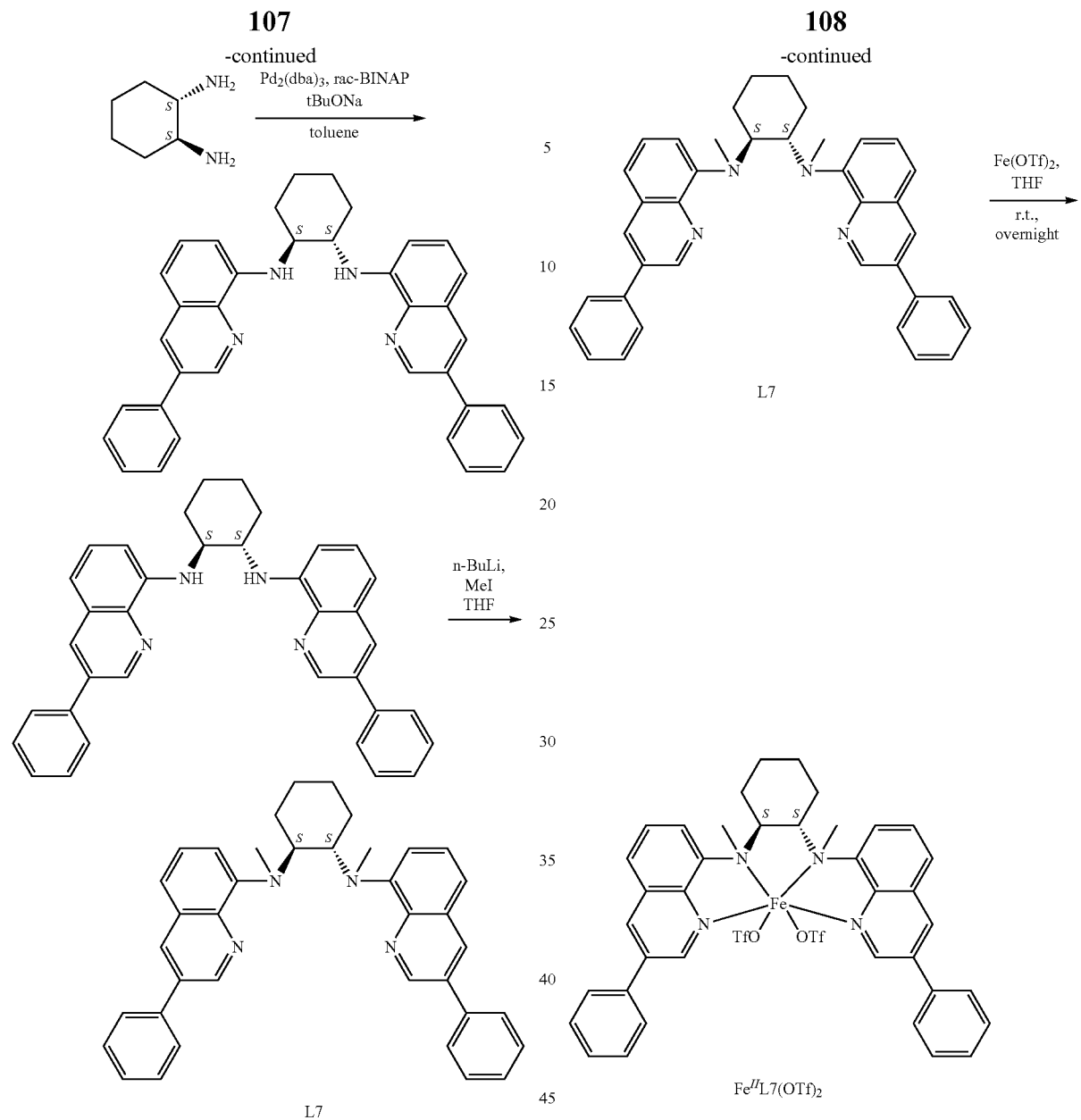
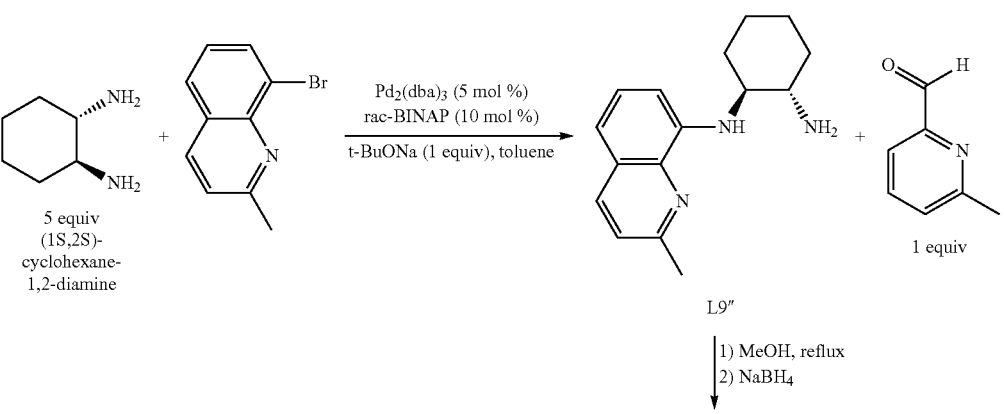
Scheme 1c. Synthesis of complex Fe$^{II}$(L9)(OTf)$_2$

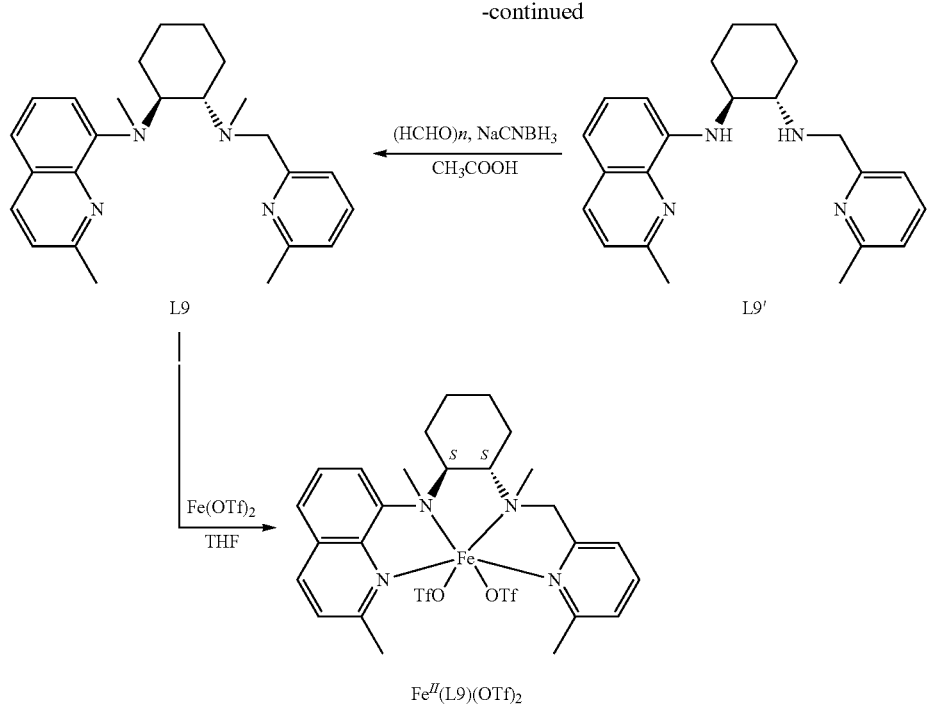

(S,S)—NN'-Bis(8-quinolyl)cyclohexane-1,2-diamine (L4') was synthesized according to reported procedure in Zang, et al., Angewandte Chemie International Edition 2016, 55, 10253-10257.

(S,S)—NN'-Dimethyl-N,N'-bis(8-quinolyl)cyclohexane-1,2-diamine (L4): CH$_3$COOH (0.5 mL) was slowly added to a solution of L4' (991 mg, 2.5 mmol), Na(CN)BH$_3$ (1.75 g, 28.0 mmol) and (HCHO)n (37-40 wt. % in H$_2$O, 4.3 mL) in MeCN (25 mL) at 0° C. The reaction mixture was stirred for 3 h at room temperature. Then the reaction was added with diethyl ether (80 mL), washed with 0.5 M NaOH (aq) (30 mL×3) and brine, dried with MgSO$_4$, filtered, and then concentrated under reduced pressure. The crude residue was purified by silica gel flash chromatography (DCM/MeOH=9:1) to afford the product L4 as a yellow solid.

(S,S)—NN'-Dimethyl-N,N'-bis(8-2'-methyl-quinolyl)cyclohexane-1,2-diamine iron(II) bis(triflate) ([Fe$^{II}$(L4)(OTf)$_2$]): 848 mg (2 mmol) of L4 and 708 mg (2 mmol) of Fe(OTf)$_2$ were dissolved in 50 mL of THF under argon, and the resulting mixture was stirred overnight. The precipitate that formed was collected by filtration under argon, washed subsequently with diethyl ether (30 mL×2), and dried under reduced pressure to give a voluminous orange powder (1.32 g, 85% yield).

Complexes Fe$^{II}$(L1)(OTf)$_2$, Fe$^{II}$(L2)(OTf)$_2$, Fe$^{II}$(L3)(OTf)$_2$, Fe$^{II}$(L5)(OTf)$_2$, Fe$^{II}$(L6)(OTf)$_2$, and Fe$^{II}$(L8)(OTf)$_2$ were synthesized according to reported procedures in Zang, et al., Angewandte Chemie International Edition 2016, 55, 10253-10257; Wei, et al., Angewandte Chemie International Edition 2020, 59, 16561-16571; Suzuki, et al., Angew Chem Int Ed 2008, 47, 1887-1889; and Wei, et al., Org. Lett., 23(17):6993-6997 (2021).

Complex Fe$^{II}$(L7)(OTf)$_2$ was prepared as follow:

A mixture of H$_2$SO$_4$ (8 mL) and HNO$_3$ (1.1 mL) was first prepared and the mixture was then cooled to below 10° C. 3-Bromobenzaldehyde (3.3 g, 17.83 mmol) was added dropwise for 40 min After addition, the reaction was stirred for extra 30 min at below 10° C. The mixture was then poured into ice-water bath and stirred for 1 h to give yellow precipitate, which was filtered and washed with water until neutral pH was reached. The crude product was purified by using flash column chromatography (silica gel) with 18-20% EA/Hex as eluent. Isolated yield was 11%.

A mixture of the 3-bromo-2-nitro-benzaldehyde (115 mg, 0.5 mmol), Fe powder (240 mg, 4 mmol), 0.1 N HCl (0.9 mL) was stirred in EtOH (1.5 mL) at 95° C. for 5 h under Ar. Then, phenylacetaldehyde (66 mg, 0.5 mmol) and KOH (80 mg, 1.5 mmol) were added to the reaction mixture. The reaction mixture was then refluxed for overnight. The mixture was diluted with CH$_2$Cl$_2$ (25 mL) and filtered through celite. The filtrate was then washed with water. The aqueous layer was back-extracted with CH$_2$Cl$_2$ (2×7 mL). The combined organic layer was dried over MgSO$_4$ and evaporated to give crude product which was purified by using flash column chromatography (silica gel) with 8-10% EA/Hex as eluent to give pure 8-bromo-3-phenylquinoline (Quinoline A). Isolated yield was 91%.

A mixture of 8-bromo-3-phenylquinoline (230 mg, 0.7 mmol), (1S,2S)-(+)-1,2-diaminocyclohexane (39 mg, 0.33 mmol), 5 mol % of Pd$_2$(dba)$_3$, rac-BINAP (25 mg, 0.034 mmol), NaOt-Bu (100 mg, 0.99 mmol) was stirred in toluene (6 mL) for 24 h at 85° C. under Ar atmosphere. After cooled to room temperature, the reaction mixture was diluted by using CH$_2$Cl$_2$ (20 mL). The mixture was filtered through celite and evaporated to dryness to give a crude product. The crude compound was purified by flash column chromatography on a silica gel column using 10% EA/Hex as eluent to give the desired diamine Isolated yield was 93%.

The diamine (97 mg, 0.192 mmol) obtained in the previous step was first dissolved in THF (7 mL). After cooled to −78° C., n-BuLi (~1.2M, 0.33 mL) was added dropwise. The mixture was stirred for 1 h and then 1 extra hour at room temperature until red-brown solution was observed. The reaction mixture was cooled to −78° C. again and MeI (0.13 mL) was added dropwise. After addition, the mixture was heated up to room temperature and then stirred for 12 h. The reaction was quenched by using saturated NaHCO$_3$ (10 mL) and diluted with EA. The aqueous layer was then extracted with CH$_2$Cl$_2$ and then dried over MgSO$_4$. The mixture was evaporated to dryness to give a crude product. The crude compound was purified by flash column chromatography on a silica gel column using 10-30% EA/Hex as eluent to give the desired product L7. Isolated yield was 94%.

A mixture of L7 (51 mg, 0.0911 mmol) and Fe(OTf)$_2$ (33 mg, 0.0911 mmol) was stirred in anhydrous THF (2 mL) for overnight at room temperature. The reaction was dried under vacuum. The solid was then washed with diethyl ether several times and dried under vacuum to give orange solid. Isolated yield was 79%. This iron complex was characterized by using ESI-MS. ESI-MS (MeCN): m/z 649.2242 ([Fe$^{II}$(L7)(HCOO)]$^+$). The source of formate (HCOO$^-$) was from sodium formate used in ESI-MS experiment.

Complex Fe$^{II}$(L9)(OTf)$_2$ was prepared as follow:

Under argon atmosphere, 8-bromo-2-methyl-quinoline (5 mmol), (1S,2S)-cyclohexane-1,2-diamine (25 mmol), Pd$_2$(dba)$_3$ (5 mol %), rac-BINAP (10 mol %) were dissolved in toluene, and then sodium t-butoxide (5 mmol) was added. The mixture was stirred at 85° C. for 24 h. After being cooled to room temperature, the reaction mixture was filtered through a plug of SiO$_2$ and concentrated under reduced pressure. The crude residue was purified by flash chromatography on silica gel (EtOAc/methanol=3:1 v/v) to afford L9" ((1S,2S)—N$^1$-(2-methylquinolin-8-yl)cyclohexane-1,2-diamine) as yellow solid. The isolated yield was 80%. $^1$H NMR (400 MHz, CDCl$_3$) δ 7.92 (d, J=6.3 Hz, 1H), 7.35-7.17 (m, 2H), 6.97 (d, J=8.0 Hz, 1H), 6.79 (d, J=7.6 Hz, 1H), 6.08 (d, J=9.3 Hz, 1H), 3.19 (qd, J=10.2, 3.7 Hz, 1H), 2.79 (dt, J=12.9, 6.4 Hz, 1H), 2.69 (s, 3H), 2.16 (d, J=12.8 Hz, 1H), 2.09-1.98 (m, 1H), 1.87-1.69 (m, 2H), 1.32 (dq, J=33.7, 12.1 Hz, 4H). $^{13}$C NMR (101 MHz, CDCl$_3$) δ 155.62, 144.43, 137.76, 136.29, 126.91, 126.81, 122.22, 113.58, 105.33, 59.86, 56.39, 35.08, 32.32, 25.62, 25.33, 25.20.

Under argon atmosphere, a mixture of 6-methylpicolinaldehyde (1 equiv) and L9" (1 equiv) in methanol (0.2 M) was refluxed overnight. After being cooled to 0° C., NaBH$_4$ (3 equiv) was added in portions. The reaction mixture was kept at 0° C. for 3 h. After that, the reaction was quenched with water. The aqueous layer was extracted with EtOAc. Finally, organic layers were concentrated and the crude product was purified by flash chromatography on silica gel (EtOAc) to afford L9' ((1S,2S)—N$^1$-(6-methylpyridin yl)methyl)-N$^2$-(2-methylquinolin-8-yl)cyclohexane-1,2-diamine) as yellow oil. The isolated yield was 80%. $^1$H NMR (400 MHz, CDCl$_3$) δ 7.96 (d, J=8.3 Hz, 1H), 7.51 (t, J=7.7 Hz, 1H), 7.32 (t, J=8.0 Hz, 1H), 7.26 (d, J=8.4 Hz, 1H), 7.19 (d, J=7.7 Hz, 1H), 7.00 (t, J=8.9 Hz, 2H), 6.85 (d, J=7.7 Hz, 1H), 6.19 (s, 1H), 4.06 (d, J=14.4 Hz, 1H), 3.92 (d, J=14.4 Hz, 1H), 3.55-3.41 (m, 1H), 2.80-2.66 (m, 4H), 2.49 (s, 3H), 2.35-2.19 (m, 2H), 1.80 (d, J=14.1 Hz, 2H), 1.53-1.26 (m, 4H). $^{13}$C NMR (101 MHz, CDCl$_3$) δ 159.39, 158.66, 155.49, 143.43, 137.97, 136.69, 136.24, 126.88, 125.65, 122.12, 120.51, 118.56, 111.54, 105.73, 60.83, 57.07, 52.56, 32.23, 31.51, 25.30, 24.65, 24.49.

Under air, 0.5 mL CH$_3$COOH was added dropwise to a solution of L9' (2.5 mmol), 4.3 mL formaldehyde (37% wt. % in H$_2$O), NaCNBH$_3$ (1.75 g) in CH$_3$CN (25 mL) at 0° C.

After the mixture was stirred at room temperature overnight, the reaction was diluted with Et$_2$O (50 mL) and washed with aqueous NaHCO$_3$. (30 mL×3). The organic fractions were combined and dried by NaSO$_4$, and concentrated under reduced pressure. The crude product was purified by flash chromatography on silica gel (hexane/Et$_3$N=100:1 v/v) to afford L9 (N$^1$, N$^2$-dimethyl-N$^1$-(6-methylpyridin-2-yl)methyl)-N$^2$-(2-methylquinolin-8-yl)cyclohexane-1,2-diamine) as yellow oil. The isolated yield was 76%. $^1$H NMR (500 MHz, CD$_2$C$_{12}$) δ 7.91 (d, J=8.4 Hz, 1H), 7.46 (t, J=7.7 Hz, 1H), 7.29 (t, J=7.8 Hz, 1H), 7.19 (dd, J=11.8, 8.0 Hz, 2H), 7.13 (d, J=7.9 Hz, 1H), 7.05 (d, J=7.7 Hz, 1H), 6.93 (d, J=7.6 Hz, 1H), 4.66 (td, J=11.1, 3.8 Hz, 1H), 3.75 (d, J=14.2 Hz, 1H), 3.58 (d, J=14.2 Hz, 1H), 2.99 (s, 3H), 2.82 (td, J=10.8, 3.5 Hz, 1H), 2.63 (s, 3H), 2.43 (s, 3H), 2.36-2.28 (m, 1H), 2.06-1.91 (m, 1H), 1.86-1.74 (m, 5H), 1.68 (qd, J=12.1, 3.6 Hz, 1H), 1.35-1.26 (m, 1H), 1.25-1.17 (m, 2H). HRMS (ESI): m/z ([M+H]$^+$) calcd. for C$_{25}$H$_{33}$N$_4$ 389.2700, found 389.2703.

Under argon atmosphere, a mixture of L9 (1 equiv) and Fe(OTf)$_2$ (1 equiv) in THF (0.1 M) was stirred overnight. After reaction was completed, THF was removed under reduced pressure carefully under argon. The crude residue was washed with dry Et$_2$O to give pure complex Fe$^{II}$(L9)(OTf)$_2$ as yellow solids. Isolated yield was 45%. This iron complex was characterized by using ESI-MS. ESI-MS (MeCN): m/z 222.0981 ([Fe$^{II}$(L9)]$^{2+}$). Elemental Analysis: calculated: C, 43.67; H, 4.34; N, 7.55; S, 8.64; found: C, 45.20; H, 4.89; N, 7.65; S, 8.02.

Asymmetric Dihydroxylation of Model Substrates

Scheme 2. Cis-dihydroxylation of 2,5-dimethylbenzoquinone (1a)

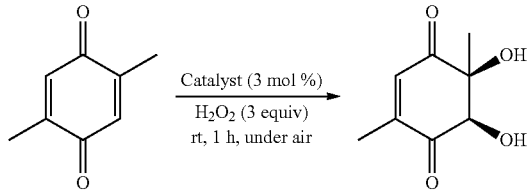

Scheme 3. Cis-dihydroxylation of [1,1'-biphenyl]-2,5-dione (3d)

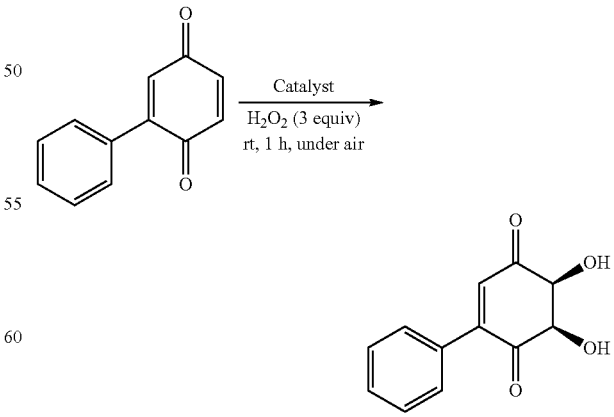

Results

The structures of exemplary Fe$^{II}$ complexes are shown below:

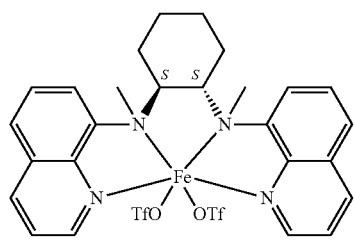

Fe$^{II}$(L1)(OTf)$_2$

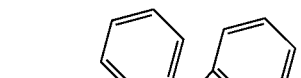

[Fe$^{II}$(L2)(OTf)$_2$]

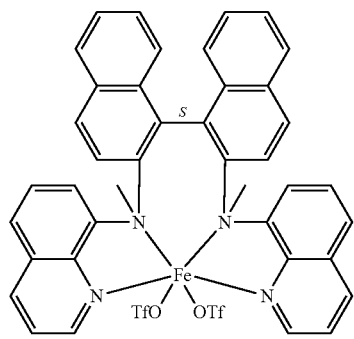

Fe$^{II}$(L3)(OTf)$_2$]

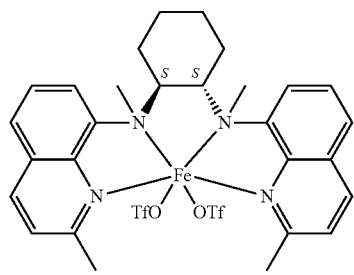

Fe$^{II}$(L4)(OTf)$_2$

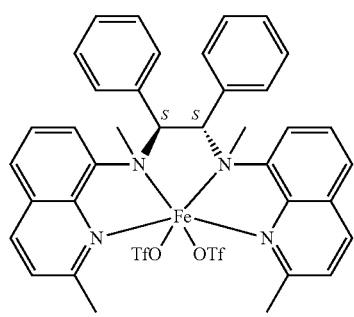

Fe$^{II}$(L5)(OTf)$_2$

-continued

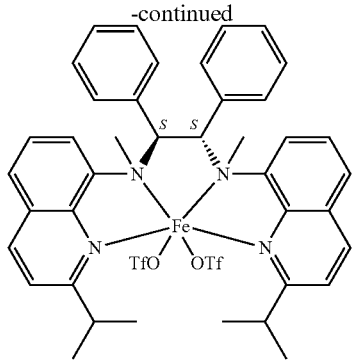

Fe$^{II}$(L6)(OTf)$_2$

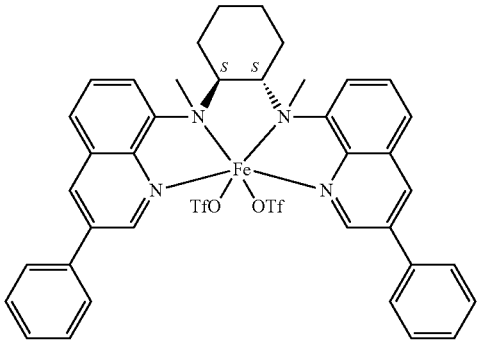

Fe$^{II}$(L7)(OTf)$_2$

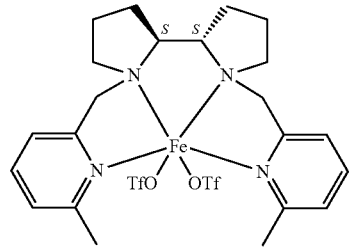

Fe$^{II}$(L8)(OTf)$_2$

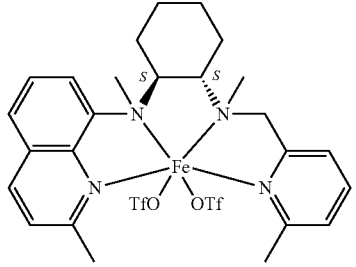

Fe$^{II}$(L9-R)(OTf)$_2$

Taking 2,5-dimethylbenzoquinone (1a) as the model substrate, different chiral Fe(II)—N$_4$ complexes were screened (Table 1). The highest yield and enantioselectivity were obtained (85% yield, 99.6% ee) by using 3 mol % of [Fe$^{II}$(L4)(OTf)$_2$]. Removing the 2-methyl groups on the quinolyl parts of the Fe catalyst led to decrease in catalytic performance. [Fe$^{II}$(L6)(OTf)$_2$] and [Fe$^{II}$(L7)(OTf)$_2$] catalysts bearing 2-isopropyl and 3-phenyl groups on the quinolyl parts instead of the 2-methyl groups gave low conversion. When H$_2$O$_2$ was added in one portion using a syringe pump, yield was slightly improved (Table 1, Entries 4 and 5). With lower catalyst loading of 0.5-2 mol %, the cis-diol products have high yield and enantioselectivity with slightly lower conversion (Table 1, Entries 14-16). Other reaction parameters such as solvent, oxidant, additives, temperature, concentration, and amount of $H_2O_2$ were also evaluated, and the results are shown in Tables 2 and 3. The results of asymmetric dihydroxylation of another substrate, [1,1'-biphenyl]-2,5-dione (3d), catalyzed by $Fe^{II}(L4)(OTf)_2$ or $Fe^{II}(L7)(OTf)_2$ under different conditions are shown in Table 4.

TABLE 1

Screening of cis-dihydroxylation of 1a.

| Entry[a] | Catalyst | Solvent | Conv. (%)[b] | Yield (%)[c] | ee (%)[d] |
|---|---|---|---|---|---|
| 1 | $Fe^{II}(L1)(OTf)_2$ | $CD_3OD$ | 50 | 45 | 47.6 |
| 2 | $Fe^{II}(L2)(OTf)_2$ | $CD_3OD$ | — | 0 | — |
| 3 | $Fe^{II}(L3)(OTf)_2$ | $CD_3OD$ | 8 | 0 | 0 |
| 4 | $Fe^{II}(L4)(OTf)_2$ | $CD_3OD$ | 100 | 85 | 99.6 |
| 5[e] | $Fe^{II}(L4)(OTf)_2$ | $CD_3OD$ | 100 | 74 | 99.6 |
| 6 | $Fe^{II}(L5)(OTf)_2$ | $CD_3OD$ | 100 | 72 | 99.4 |
| 7 | $Fe^{II}(L6)(OTf)_2$ | $CD_3OD$ | 0 | — | — |
| 8 | $Fe^{II}(L7)(OTf)_2$ | $CD_3OD$ | 20 | 10 | 37.3 |
| 9 | $Fe^{II}(L8)(OTf)_2$ | $CD_3OD$ | 41 | 68 | 61.8 |
| 10 | $Fe^{II}(L4)(OTf)_2$ | $CH_3OH$ | 100 | 83 | 99.9 |
| 11 | $Fe^{II}(L4)(OTf)_2$ | EtOH | 84 | 60 | 98.3 |
| 12 | $Fe^{II}(L4)(OTf)_2$ | $CD_3CN$ | 80 | 50 | 93.6 |
| 13 | $Fe^{II}(L4)(OTf)_2$ | $CD_2Cl_2$ | 4 | 0 | — |
| 14[f] | $Fe^{II}(L4)(OTf)_2$ | $CD_3OD$ | 100 | 81 | 99.1 |
| 15[g] | $Fe^{II}(L4)(OTf)_2$ | $CD_3OD$ | 72 | 92 | 99.9 |
| 16[h] | $Fe^{II}(L4)(OTf)_2$ | $CD_3OD$ | 55 | 98 | 99.9 |
| 17[i] | $Fe^{II}(L9)(OTf)_2$ | $CH_3OH$ | 100 | 81 | 96 |

[a]Reaction conditions: quinone 1a (0.2 mmol) and catalyst (3 mol %) in solvent (2 mL), $H_2O_2$ (3 equiv), in 1 mL of $CD_3OD$ for 1 h.
[b]Substrate conversion determined by crude $^1H$ NMR.
[c]Cis-diol yield based on substrate conversion determined by crude $^1H$ NMR, PhTMS as internal standard.
[d]Enantiomeric excess (ee) determined by chiral HPLC.
[e]$H_2O_2$ (3 equivalent, in 1 mL of $CD_3OD$) added by syringe pump for 30 minutes.
[f]2 mol % of catalyst loading.
[g]1 mol % of catalyst loading.
[h]0.5 mol % of catalyst loading.
[i]5 mol % of catalyst loading.

TABLE 2

Catalyst loadings, concentration, and amount of $H_2O_2$ examined for AD of 2,5-dimethyl-1,4-benzoquinone (1a) catalysed by $Fe^{II}(L4)(OTf)_2$.

| Entry[a] | Catalyst (%) | $H_2O_2$ (equiv) | Conv. (%)[b] | Yield (%)[c] | ee (%)[d] |
|---|---|---|---|---|---|
| 1 | 0.5 | 3 | 55 | 98 | 99.9 |
| 2 | 1 | 3 | 72 | 92 | 99.9 |
| 3 | 2 | 3 | 100 | 81 | 99.1 |
| 4 | 3 | 3 | 100 | 85 | 99.6 |
| 5 | 5 | 3 | 100 | 74 | 99.3 |
| 6 | 3 | 1 | 100 | 75 | 99.3 |
| 7 | 3 | 4 | 100 | 85 | 99.3 |
| 8[e] | 3 | 3 | 100 | 75 | 99.5 |
| 9[f] | 3 | 3 | 100 | 85 | 99.6 |
| 10[g] | 3 | 3 | 100 | 78 | 99.1 |

[a]Reaction conditions: $Fe^{II}(L4)(OTf)_2$ (3 mol %) and 2,5-dimethyl-1,4-benzoquinone (0.2 mmol) in 2 mL $CD_3OD$, $H_2O_2$ in 1 mL $CD_3OD$, and the reaction mixture was stirred for an 1 h.
[b]Determined by $^1H$ NMR with PhTMS as an internal standard.
[c]Determined by $^1H$ NMR and based on conversions.
[d]Determined by HPLC.
[e]Total amount of $CD_3OD$ added 1.5 mL.
[f]Total amount of $CD_3OD$ added 6 mL.
[g]Added with AcOH (1 equiv).

TABLE 3

Temperature, oxidant, and solvent examined for AD of 2,5-dimethyl-1,4-benzoquinone (1a) catalysed by $Fe^{II}(L4)(OTf)_2$.

| Entry[a] | T (° C.) | Oxidant | Solvent | Conv. (%)[b] | Yield (%)[c] | ee (%)[d] |
|---|---|---|---|---|---|---|
| 1 | rt | $O_2$ | $CD_3OD$ | 5 | 0 | — |
| 2 | rt | Oxone | $CD_3OD$ | 4 | 0 | — |
| 3 | rt | PhIO | $CD_3OD$ | 12 | 0 | — |
| 4 | rt | CAN[e] | $CD_3OD$ | 7 | 0 | — |
| 5 | 0 | $H_2O_2$ | $CD_3OD$ | 100 | 78 | 99.3 |
| 6 | 50 | $H_2O_2$ | $CD_3OD$ | 100 | 74 | 98.3 |
| 7 | rt | $H_2O_2$ | $CD_2Cl_2$ | 4 | 0 | — |
| 8 | rt | $H_2O_2$ | $CD_3CN$ | 80 | 50 | 93.6 |
| 9 | rt | $H_2O_2$ | EtOH | 84 | 60 | 98.3 |
| 10 | rt | $H_2O_2$ | $CH_3OH$ | 100 | 83 | 99.9 |

[a]Reaction conditions: $Fe^{II}(L4)(OTf)_2$ (3 mol %) and 2,5-dimethyl-1,4-benzoquinone (0.1 mmol) in 1.5 mL of solvent, oxidant (for $O_2$, the reaction was conducted under a balloon filled with $O_2$; for Oxone, PhIO and CAN, they were added directly into the reaction mixture; for $H_2O_2$, it was diluted with 0.5 mL $CD_3OD$ before injection into the reaction mixture), and the reaction mixture was stirred for 1 h.
[b]Determined by $^1H$ NMR with PhTMS as an internal standard.
[c]Determined by $^1H$ NMR and based on conversions.
[d]Determined by HPLC.
[e]Cerium (IV) ammonium nitrate.

TABLE 4

AD of 2-phenyl-1,4-benzoquinone (3d) catalyzed by $Fe^{II}(L4)(OTf)_2$ or $Fe^{II}(L7)(OTf)_2$ under different conditions.

| Entry[a] | Catalyst | $H_2O_2$ (equiv) | Additives | Conv. (%)[b] | Yield (%)[c] | ee (%)[d] |
|---|---|---|---|---|---|---|
| 1 | $Fe^{II}(L4)(OTf)_2$ | 1 | — | 100 | 38 | 91.2 |
| 2 | $Fe^{II}(L4)(OTf)_2$ | 3 | — | 100 | 50 | 90.5 |
| 3[e] | $Fe^{II}(L4)(OTf)_2$ | 3 | — | 100 | 41 | 92.1 |
| 4[f] | $Fe^{II}(L4)(OTf)_2$ | 3 | — | 100 | 38 | 90.0 |
| 5[g] | $Fe^{II}(L4)(OTf)_2$ | 3 | — | 100 | 18 | — |
| 6 | $Fe^{II}(L4)(OTf)_2$ | | HOAc | 100 | 32 | 88.9 |
| 7 | $Fe^{II}(L7)(OTf)_2$ | | — | 17 | 0 | — |

[a]Reaction conditions: $Fe^{II}(L4)(OTf)_2$ (3 mol %), 2-phenyl-1,4-benzoquinone (0.1 mmol) in 2.5 mL $CD_3OD$, and $H_2O_2$ (0.3 mmol, dissolved in 0.5 mL of $CD_3OD$), and the reaction mixture was stirred for 1 h.
[b]Determined by $^1H$ NMR with PhTMS as an internal standard.
[c]Determined by $^1H$ NMR and based on conversions.
[d]Determined by HPLC.
[e]0° C.
[f]2 mol % catalyst loading.
[g]5 mol % catalyst loading.

Example 2. The Exemplary Fe(II) Complex Catalyzes Substituted Benzoquinones and Naphthoquinones Materials and Methods Preparation of Substrates Scheme 4. Four methods for synthesizing the substrates Method A

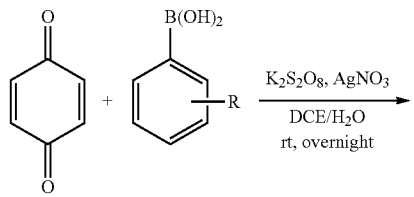

-continued

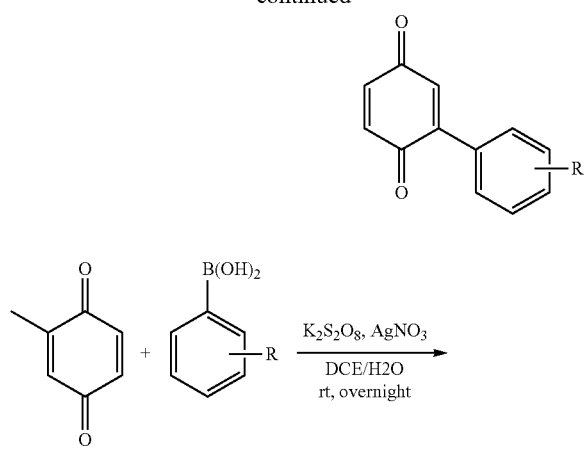

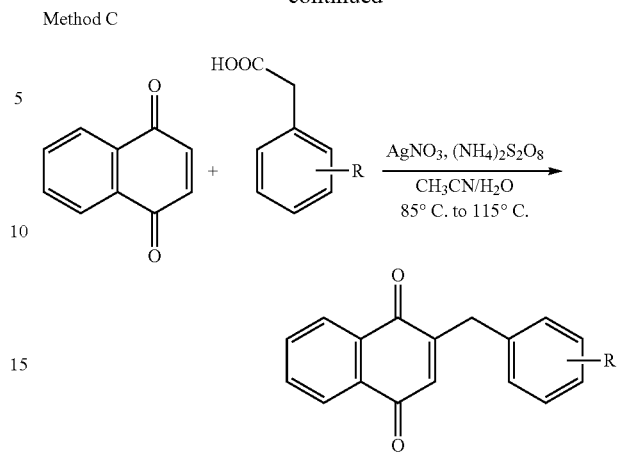

Method B

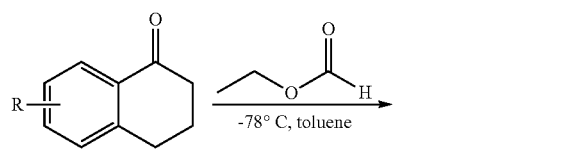

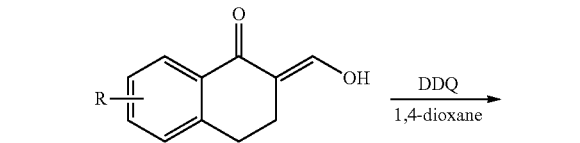

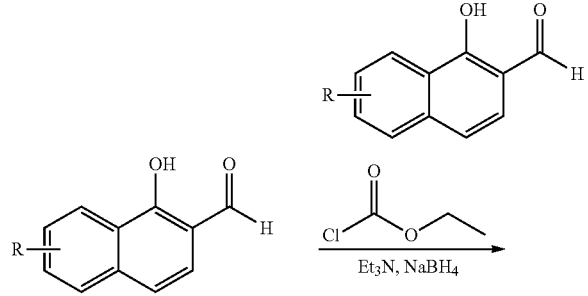

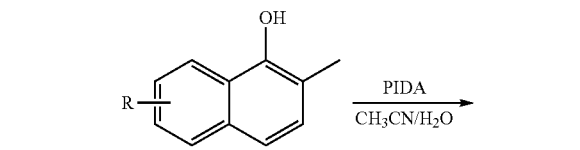

Substrates 1a, 1b, 1c, 1d, 1g, 1h, 1l, 3b, 3c, 3d, 3l are commercially available. Substrates 1e, 1f, 3f, 3h-3j were synthesized by method A according to reported procedure in Fujiwara, et al., JAGS 2011, 133, 3292-3295. Substrates 1i, 1j, 1k were synthesized by method B according to reported procedure in Rodo, et al., *European Journal of Organic Chemistry* 2016, 2016, 1982-1993. Substrates 1n-1q were synthesized by method C according to reported procedure in Feng, et al., *Organic & Biomolecular Chemistry* 2018, 16, 2647-2665. Substrate 1m was synthesized according to reported procedure. Substrates 1r-1u, 3e, 3g, 3n were synthesized by method D according to reported procedure in Viault, et al., *European Journal of Organic Chemistry* 2011, 2011, 1233-1241.

General Procedure of Asymmetric Cis-Dihydroxylation Reactions $H_2O_2$ (0.6 mmol, 3 equiv.; 30% aqueous solution dissolved in 1.0 mL of $CD_3OD$) was added to a solution of $Fe^{II}(L4)(OTf)_2$ (0.006 mmol, 3 mol %) and substrate (0.2 mmol) in $CD_3OD$ (2 mL) in one portion and the reaction mixture was stirred for 1 h. After completion of the reaction (TLC monitoring), internal standard PhTMS was added to the reaction. Conversion and yield were determined by crude $^1H$ NMR. The mixture was filtered through a short column of silica (5 cm), and the column was further eluted with ethyl acetate (50 mL) to obtain the crude product. The cis-diol product was purified by column chromatography on silica gel. The enantiomeric excess (i.e. ee) of purified cis-diol product was determined by chiral HPLC.

Gram-Scale Reactions

Scheme 5. Gram-scale AD reaction of vitamin K3.

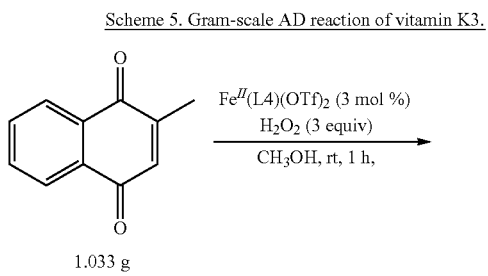

1.033 g

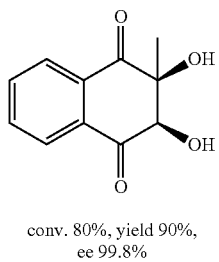

conv. 80%, yield 90%, ee 99.8%

To a mixture of Vitamin K₃ 1 h (1.0 g, 6 mmol) and Fe$^{II}$(L4)(OTf)₂ dissolved in HPLC grade methanol (60 mL), H₂O₂ (3 equiv., 30% aqueous solution diluted with 30 mL of methanol) was added in one portion at 27° C., and the reaction mixture was then stirred for 2 h. The reaction was filtered through a column of silica gel (20 cm), and the column was further eluted with ethyl acetate (200 mL) to obtain the crude product. Methanol was removed under reduced pressure using a rotary evaporator. The residue was purified by flash chromatography on silica gel (50% ethyl acetate/hexane) to give a white solid (1.1 g, 90% yield, 99.8% ee).

Further Reduction of the Cis-Diol Products

Scheme 6. Preparation of triols and tetraols.

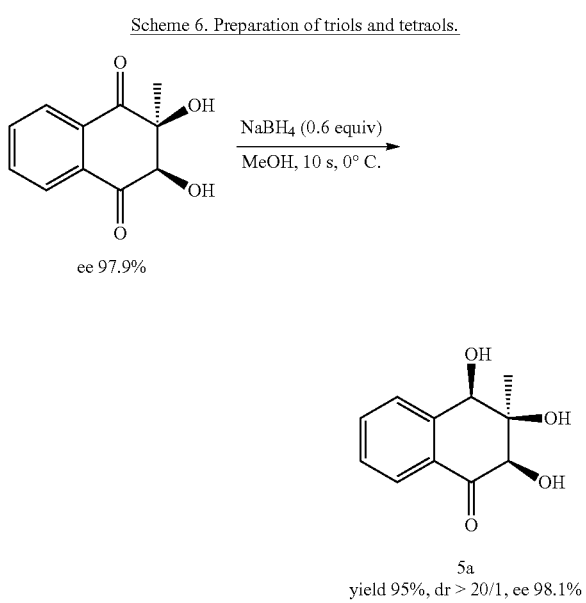

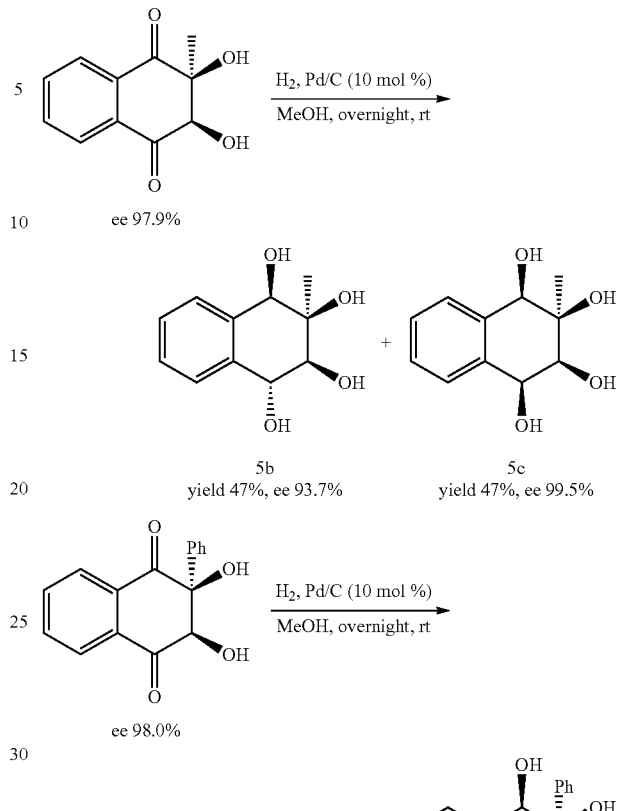

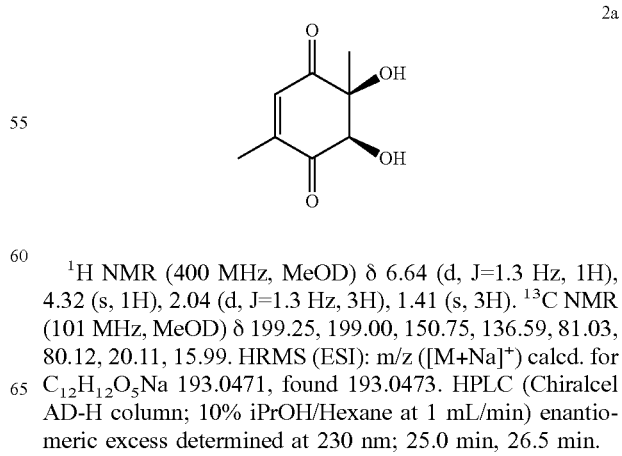

Results

Structure Characterization

The structures, NMR results, and HPLC analysis of the cis-diol products and one model tetraol product (following further reduction) are summarized below:

$^{1}$H NMR (400 MHz, MeOD) δ 6.64 (d, J=1.3 Hz, 1H), 4.32 (s, 1H), 2.04 (d, J=1.3 Hz, 3H), 1.41 (s, 3H). $^{13}$C NMR (101 MHz, MeOD) δ 199.25, 199.00, 150.75, 136.59, 81.03, 80.12, 20.11, 15.99. HRMS (ESI): m/z ([M+Na]$^{+}$) calcd. for C₁₂H₁₂O₅Na 193.0471, found 193.0473. HPLC (Chiralcel AD-H column; 10% iPrOH/Hexane at 1 mL/min) enantiomeric excess determined at 230 nm; 25.0 min, 26.5 min.

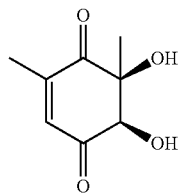

2b

¹H NMR (500 MHz, MeOD) δ 6.70 (d, J=1.5 Hz, 1H), 4.29 (s, 1H), 2.03 (d, J=1.5 Hz, 3H), 1.45 (s, 3H). ¹³C NMR (126 MHz, MeOD) δ 199.04, 198.72, 150.75, 136.32, 80.80, 80.08, 20.00, 16.41. HRMS (ESI): m/z ([M+Na]⁺) calcd. for $C_{12}H_{12}O_5Na$ 193.0471, found 193.0475. HPLC (Chiralcel AD-H column; 5% iPrOH/Hexane at 1 mL/min) enantiomeric excess determined at 250 nm; 53.3 min, 56.6 min.

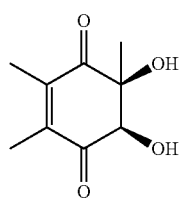

2c

¹H NMR (300 MHz, CDCl₃) δ 4.27 (s, 1H), 3.71 (s, 1H), 3.00 (s, 1H), 2.06 (d, J=3.5 Hz, 6H), 1.50 (s, 3H). ¹³C NMR (126 MHz, CDCl₃) δ 196.84, 196.72, 145.01, 143.98, 79.12, 78.65, 21.26, 13.39, 13.13. HRMS (ESI): m/z ([M+Na]⁺) calcd. for $C_9H_{12}O_4Na$ 207.0628, found 207.0628. HPLC (Chiralcel AD-H column; 10% iPrOH/Hexane at 1 mL/min) enantiomeric excess determined at 270 nm; 20.0 min, 28.1 min.

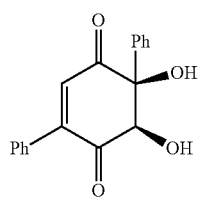

2d

¹H NMR (500 MHz, DMSO) δ 7.64-7.57 (m, 2H), 7.49 (t, J=6.5 Hz, 2H), 7.41 (d, J=7.5 Hz, 2H), 7.36 (t, J=7.3 Hz, 2H), 7.30 (t, J=7.1 Hz, 1H), 6.68 (d, J=9.4 Hz, 1H), 5.88 (d, J=6.3 Hz, 1H), 5.14 (d, J=6.3 Hz, 1H), 3.41 (s, 1H). ¹³C NMR (126 MHz, DMSO) δ 197.90, 196.85, 148.55, 139.38, 134.21, 132.83, 130.33, 129.01, 128.59, 127.62, 127.37, 127.18, 83.45, 80.70. HRMS (ESI): m/z ([M+Na]⁺) calcd. for $C_{18}H_{14}O_4Na$ 317.0784, found 317.0785. HPLC (Chiralcel OD-H column; 10% iPrOH/Hexane at 1 mL/min) enantiomeric excess determined at 220 nm; 49.9 min, 66.9 min.

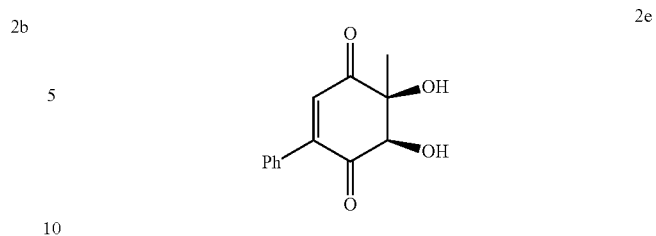

2e

¹H NMR (500 MHz, MeOD) δ 7.56 (d, J=7.3 Hz, 2H), 7.49-7.41 (m, 4H), 7.35 (q, J=7.9 Hz, 4H), 7.30 (t, J=6.4 Hz, 1H), 6.91 (s, 1.25H), 6.75 (s, 1H), 4.54 (s, 1.2H), 2.04 (s, 3H), 1.48 (s, 4.2H). ¹³C NMR (126 MHz, MeOD) δ 198.94, 198.85, 198.69, 198.51, 150.87, 150.60, 139.94, 137.29, 134.98, 134.36, 131.36, 130.04, 129.57, 129.13, 129.02, 128.09, 84.35, 82.26, 80.78, 80.09, 20.14, 16.00. HRMS (ESI): m/z ([M+Na]+) calcd. for $C_{13}H_{12}O_4Na$ 255.0628, found 255.0628. HRMS (ESI): m/z ([M+Na]⁺) calcd. for $C_{13}H_{12}O_4Na$ 255.0628, found 255.0628. HPLC (Chiralcel OD-3 column; 7% iPrOH/Hexane at 1 mL/min) enantiomeric excess determined at 230 nm; 51.0 min, 55.0 min.

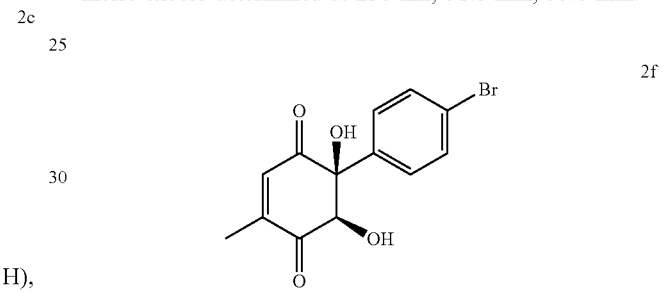

2f

¹H NMR (500 MHz, MeOD) δ 7.59 (d, J=8.3 Hz, 1H), 7.49 (t, J=7.6 Hz, 2H), 7.31 (d, J=8.2 Hz, 1H), 6.94 (s, 1H), 6.74 (s, 1H), 4.89 (s, 1H), 4.54 (s, 1H), 2.07 (s, 2H), 1.48 (s, 1H). ¹³C NMR (126 MHz, MeOD) δ 198.67, 198.63, 198.60, 197.56, 151.07, 149.28, 139.28, 137.04, 135.23, 133.30, 132.76, 132.43, 131.96, 131.82, 130.19, 125.73, 122.73, 93.94, 84.34, 82.11, 80.48, 80.14, 20.04, 16.07. HRMS (ESI): m/z ([M+Na]⁺) calcd. for $C_{13}H_{11}BrO_4Na$ 332.9733, found 332.9738. HPLC (Chiralcel AD-3 column; 10% iPrOH/Hexane at 1 mL/min) enantiomeric excess determined at 230 nm; 43.0 min, 57.4 min.

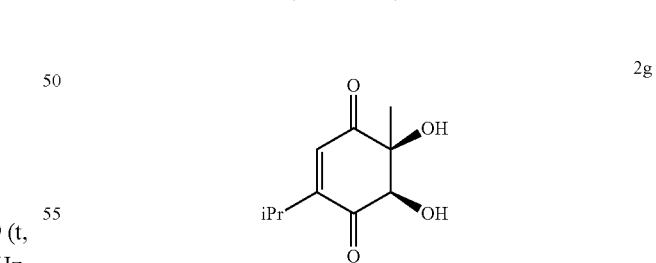

2g

¹H NMR (400 MHz, MeOD) δ 6.67 (s, 1H), 6.53 (s, 2H), 4.36 (s, 1H), 4.30 (s, 2H), 2.99 (dq, J=13.7, 6.8 Hz, 2H), 2.01 (s, 3H), 1.89 (dt, J=13.6, 6.8 Hz, 1H), 1.40 (s, 6H), 1.16 (d, J=6.8 Hz, 6H), 1.11 (d, J=6.9 Hz, 6H), 1.00 (d, J=6.8 Hz, 3H), 0.81 (d, J=6.8 Hz, 3H). ¹³C NMR (126 MHz, MeOD) δ 201.57, 199.42, 199.14, 199.02, 159.76, 150.39, 136.48, 133.36, 85.00, 81.68, 80.06, 80.03, 34.04, 28.80, 21.38, 21.09, 20.23, 17.46, 16.89, 15.78. HRMS (ESI): m/z ([M+Na]⁺) calcd. for $C_9H_{12}O_4Na$ 221.0784, found 221.0784.

HPLC (Chiralcel AD-H column; 10% iPrOH/Hexane at 1 mL/min) enantiomeric excess determined at 250 nm; 24.7 min, 25.6 min.

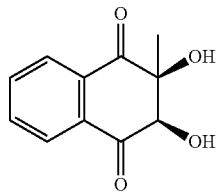
2h $^1$H NMR (400 MHz, MeOD) δ 8.11-8.01 (m, 2H), 7.85-7.79 (m, 2H), 4.52 (s, 1H), 1.52 (s, 3H). $^{13}$C NMR (126 MHz, MeOD) δ 197.45, 197.35, 135.49, 135.41, 135.16, 81.33, 80.57, 20.01. HRMS (ESI): m/z ([M+Na]$^+$) calcd. for C$_{11}$H$_{10}$O$_4$Na 229.0471, found 229.0473. HPLC (Chiralcel AD-H column; 10% iPrOH/Hexane at 1 mL/min) enantiomeric excess determined at 230 nm; 29.1 min, 34.9 min.

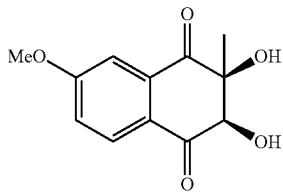
2i $^1$H NMR (400 MHz, MeOD) δ 8.03 (d, J=8.7 Hz, 1H), 7.46 (d, J=2.7 Hz, 1H), 7.32 (dd, J=8.7, 2.7 Hz, 1H), 4.50 (s, 1H), 3.95 (s, 3H), 1.50 (s, 3H). $^{13}$C NMR (101 MHz, MeOD) δ 197.44, 196.35, 165.95, 137.35, 130.93, 128.14, 121.93, 110.59, 81.43, 80.35, 56.51, 20.22. HRMS (ESI): m/z ([M+Na]$^+$) calcd. for C$_{12}$H$_{12}$O$_5$Na 259.0577, found 245.0579. HRMS (ESI): m/z ([M+H]$^+$) calcd. for C$_{12}$H$_{13}$O$_5$ 237.0759, found 237.0759. HPLC (Chiralcel AD-H column; 10% iPrOH/Hexane at 1 mL/min) enantiomeric excess determined at 250 nm; 38.9 min, 46 min.

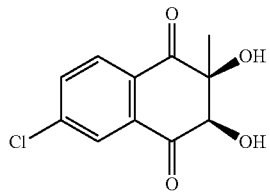
2j $^1$H NMR (500 MHz, MeOD) δ 8.02 (dd, J=8.7, 5.2 Hz, 2H), 7.82 (dd, J=8.3, 2.2 Hz, 1H), 4.54 (s, 1H), 1.52 (s, 3H). $^{13}$C NMR (101 MHz, MeOD) δ 196.46, 196.08, 141.83, 136.71, 135.31, 133.64, 129.48, 128.03, 81.15, 80.66, 19.75. HRMS (ESI): m/z ([M+Na]$^+$) calcd. for C$_{11}$H$_9$ClO$_4$Na 263.0082, found 263.0081. HPLC (Chiralcel AD-H column; 10% iPrOH/Hexane at 1 mL/min) enantiomeric excess determined at 280 nm; 25.0 min, 28.5 min.

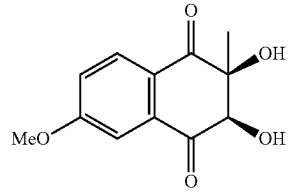
2k $^1$H NMR (500 MHz, CDCl$_3$) δ 7.80-7.69 (m, 2H), 7.33 (d, J=8.1 Hz, 1H), 4.43 (s, 1H), 4.00 (s, 3H), 1.60 (s, 3H). $^{13}$C NMR (101 MHz, CDCl$_3$) δ 195.10, 193.94, 159.39, 135.87, 135.43, 121.51, 120.21, 118.10, 80.32, 79.13, 56.70, 20.73. HRMS (ESI): m/z ([M+Na]$^+$) calcd. for C$_{12}$H$_{12}$O$_5$Na 259.0577, found 259.0575. HPLC (Chiralcel AD-H column; 10% iPrOH/Hexane at 1 mL/min) enantiomeric excess determined at 230 nm; 67.7 min, 95.3 min.

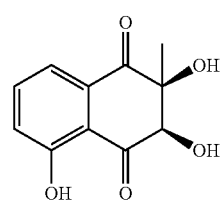
2l $^1$H NMR (300 MHz, CDCl$_3$) δ 7.76-7.60 (m, 2H), 7.33 (d, J=8.0 Hz, 1H), 4.45 (s, 1H), 3.46 (d, J=33.8 Hz, 2H), 1.55 (s, 3H). $^{13}$C NMR (101 MHz, CDCl$_3$) δ 199.97, 196.11, 161.77, 137.63, 133.18, 124.54, 119.64, 115.71, 79.34, 78.67, 21.44. HRMS (ESI): m/z ([M+Na]$^+$) calcd. for C$_{11}$H$_{10}$O$_5$Na 245.0420, found 245.0421. HPLC (Chiralcel AD-H column; 10% iPrOH/Hexane at 1 mL/min) enantiomeric excess determined at 250 nm; 59.0 min, 49.9 min.

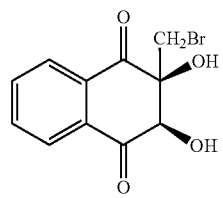
2m $^1$H NMR (500 MHz, CDCl$_3$) δ 8.20 (dd, J=5.6, 3.3 Hz, 1H), 8.13-8.06 (m, 1H), 7.88-7.80 (m, 2H), 5.16 (s, 1H), 4.04 (t, J=7.0 Hz, 2H), 3.65 (d, J=10.0 Hz, 1H). $^{13}$C NMR (126 MHz, CDCl$_3$) δ 195.83, 190.41, 135.50, 135.33, 133.37, 132.88, 128.49, 127.01, 79.49, 75.63, 30.25. HRMS (ESI): m/z ([M+Na]$^+$) calcd. for C$_{11}$H$_9$BrO$_4$Na 306.9576, found 306.9576. HPLC (Chiralcel AD-H column; 10% iPrOH/Hexane at 1 mL/min) enantiomeric excess determined at 250 nm; 30.8 min, 39.3 min.

2n

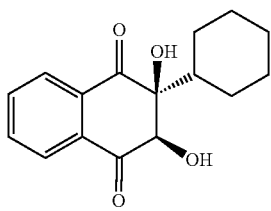

¹H NMR (400 MHz, MeOD) δ 8.07-8.00 (m, 2H), 7.87-7.81 (m, 2H), 4.54 (s, 1H), 1.79 (s, 1H), 1.68-1.54 (m, 2H), 1.53-1.42 (m, 2H), 1.41-1.27 (m, 2H), 1.20-1.07 (m, 3H), 0.98 (tt, J=12.9, 3.5 Hz, 1H). ¹³C NMR (101 MHz, MeOD) δ 200.48, 196.76, 135.74, 135.63, 135.32, 135.12, 127.92, 127.86, 85.53, 80.41, 43.88, 27.69, 27.36, 27.32, 27.17, 27.07. HRMS (ESI): m/z ([M+Na]⁺) calcd. for $C_{16}H_{18}O_4Na$ 297.1097, found 297.1097. HPLC (Chiralcel AD-H column; 15% iPrOH/Hexane at 1 mL/min) enantiomeric excess determined at 250 nm; 23.5 min, 26.6 min.

2o

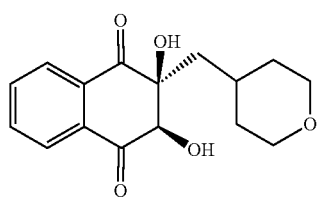

¹H NMR (500 MHz, MeOD) δ 8.10-8.02 (m, 2H), 7.87-7.82 (m, 2H), 4.46 (s, 1H), 3.82 (ddd, J=24.2, 11.4, 2.2 Hz, 2H), 3.35 (ddd, J=11.9, 8.5, 2.1 Hz, 2H), 1.84 (dd, J=13.9, 5.6 Hz, 1H), 1.81-1.72 (m, 1H), 1.67 (d, J=13.4 Hz, 1H), 1.63-1.51 (m, 2H), 1.30 (ddd, J=25.0, 12.2, 4.4 Hz, 1H), 1.20-1.08 (m, 1H). ¹³C NMR (101 MHz, MeOD) δ 198.87, 197.18, 135.73, 135.66, 135.20, 134.97, 128.26, 127.81, 82.82, 81.27, 68.96, 68.80, 42.27, 35.42, 35.05, 32.01. HRMS (ESI): m/z ([M+Na]⁺) calcd. for $C_{16}H_{18}O_5Na$ 313.1046, found 313.1046. HPLC (Chiralcel AD-H column; 10% iPrOH/Hexane at 1 mL/min) enantiomeric excess determined at 230 nm; 52.8 min, 65.9 min.

2p

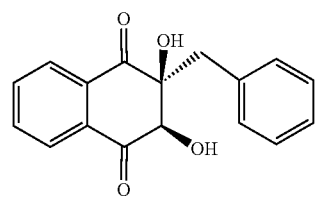

¹H NMR (400 MHz, MeOD) δ 8.07-7.97 (m, 2H), 7.84-7.77 (m, 2H), 4.37 (s, 1H), 3.35 (d, J=13.3 Hz, 1H), 3.03 (d, J=13.3 Hz, 1H). ¹³C NMR (101 MHz, MeOD) δ 197.69, 196.85, 136.91, 135.74, 135.68, 135.01, 134.85, 132.06, 129.04, 128.38, 127.72, 127.61, 83.29, 79.03, 40.92. HRMS (ESI): m/z ([M+Na]⁺) calcd. for $C_{17}H_{14}O_4Na$ 305.0784, found 305.0783. HPLC (Chiralcel AD-H column; 10% iPrOH/Hexane at 1 mL/min) enantiomeric excess determined at 250 nm; 40.0 min, 45.3 min.

2q

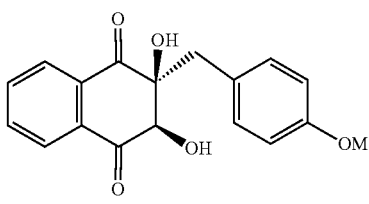

¹H NMR (400 MHz, DMSO) δ 7.96 (d, J=14.5 Hz, 1H), 7.87 (s, 1H), 7.17 (d, J=7.8 Hz, 2H), 6.78 (d, J=7.8 Hz, 2H), 6.27-6.04 (m, 2H), 4.31 (d, J=4.7 Hz, 1H), 3.68 (s, 3H), 3.15 (d, J=13.3 Hz, 1H), 2.90 (d, J=13.3 Hz, 1H). ¹³C NMR (101 MHz, DMSO) δ 196.55, 195.73, 157.84, 134.74, 134.61, 133.56, 133.14, 131.81, 127.64, 126.95, 126.32, 113.29, 82.09, 77.55, 54.93. HRMS (ESI): m/z ([M+Na]⁺) calcd. for $C_{18}H_{16}O_5Na$ 335.0890, found 335.0889. HPLC (Chiralcel AD-H column; 10% iPrOH/Hexane at 1 mL/min) enantiomeric excess determined at 250 nm; 59.1 min, 67.1 min.

2r

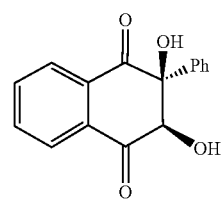

¹H NMR (500 MHz, MeOD) δ 8.12 (d, J=7.2 Hz, 1H), 8.02 (d, J=7.5 Hz, 1H), 7.82 (pd, J=7.3, 1.7 Hz, 2H), 7.37 (d, J=7.3 Hz, 2H), 7.30 (dt, J=20.1, 6.9 Hz, 3H), 5.05 (s, 1H). ¹³C NMR (126 MHz, MeOD) δ 187.85, 187.16, 130.15, 126.41, 126.20, 126.13, 125.66, 119.81, 119.74, 118.83, 118.79, 118.30, 75.33, 71.78. HRMS (ESI): m/z ([M+Na]⁺) calcd. for $C_{16}H_{12}O_4Na$ 291.0628, found 245.0625. HPLC (Chiralcel AD-H column; 10% iPrOH/Hexane at 1 mL/min) enantiomeric excess determined at 250 nm; 60.9 min, 84.6 min.

2s

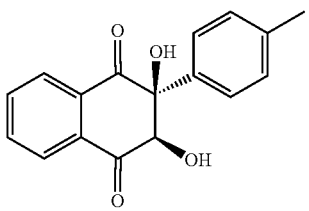

¹H NMR (400 MHz, MeOD) δ 8.15-8.05 (m, 1H), 8.03-7.95 (m, 1H), 7.86-7.75 (m, 2H), 7.21 (d, J=8.3 Hz, 2H), 7.11 (d, J=8.1 Hz, 2H), 4.99 (s, 1H), 2.28 (s, 3H). ¹³C NMR (101 MHz, MeOD) δ 197.74, 196.51, 139.37, 136.51, 135.96, 135.67, 135.56, 135.07, 130.03, 128.18, 127.83, 84.52, 81.36, 21.06. HRMS (ESI): m/z ([M+Na]⁺) calcd. for $C_{16}H_{18}O_4Na$ 305.0784, found 305.0781. HPLC (Chiralcel AD-H column; 10% iPrOH/Hexane at 1 mL/min) enantiomeric excess determined at 230 nm; 65.4 min, 86.2 min.

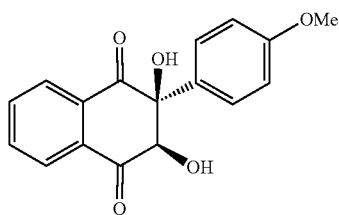

2t

¹H NMR (400 MHz, MeOD) δ 8.14-8.05 (m, 1H), 7.97 (dd, J=7.2, 1.3 Hz, 1H), 7.84-7.72 (m, 2H), 7.24 (d, J=8.8 Hz, 2H), 6.83 (d, J=8.8 Hz, 2H), 4.99 (s, 1H), 3.71 (s, 3H). ¹³C NMR (101 MHz, MeOD) δ 197.88, 196.47, 161.02, 135.89, 135.67, 135.55, 134.96, 131.30, 129.54, 128.13, 127.83, 114.81, 84.24, 81.38, 55.68. HRMS (ESI): m/z ([M+Na]⁺) calcd. for $C_{17}H_{14}O_5Na$ 321.0733, found 321.0733. HPLC (Chiralcel AD-H column; 10% iPrOH/Hexane at 1 mL/min) enantiomeric excess determined at 250 nm; 71.0 min, 80.5 min.

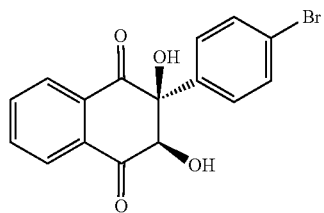

2u

¹H NMR (500 MHz, MeOD) δ 8.15-8.10 (m, 1H), 8.08-8.04 (m, 1H), 7.88-7.82 (m, 2H), 7.38 (dd, J=25.8, 8.7 Hz, 4H), 5.09 (s, 1H). ¹³C NMR (126 MHz, CDCl₃) δ 194.46, 194.23, 135.91, 135.38, 135.34, 135.05, 133.79, 133.27, 129.05, 128.26, 128.14, 127.51, 82.52, 78.87. HRMS (ESI): m/z ([M+Na]⁺) calcd. for $C_{16}H_{11}BrO_4Na$ 368.9738, found 368.9735. HPLC (Chiralcel AD-H column; 10% iPrOH/Hexane at 1 mL/min) enantiomeric excess determined at 250 nm; 52.3 min, 65.0 min.

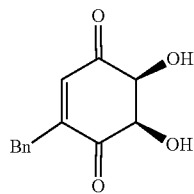

4b

¹H NMR (400 MHz, MeOD) δ 7.36-7.27 (m, 2H), 7.25-7.18 (m, 3H), 6.37 (s, 1H), 4.50 (dd, J=17.7, 3.0 Hz, 2H), 3.74 (s, 2H). ¹³C NMR (101 MHz, MeOD) δ 198.19, 198.01, 154.21, 138.21, 136.89, 130.37, 129.76, 127.89, 78.21, 77.86, 36.33. HRMS (ESI): m/z ([M+Na]⁺) calcd. for $C_{13}H_{12}O_4Na$ 255.0628, found 255.0626. HPLC (Chiralcel ASH column; 10% iPrOH/Hexane at 1 mL/min) enantiomeric excess determined at 250 nm; 66.9 min, 74.2 min.

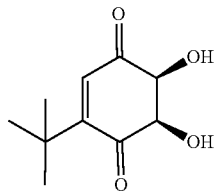

4c

¹H NMR (500 MHz, MeOD) δ 6.60 (s, 1H), 4.47 (dd, J=11.2, 3.3 Hz, 2H), 1.27 (s, 9H). ¹³C NMR (126 MHz, MeOD) δ 199.06, 198.66, 162.01, 134.52, 79.77, 77.46, 36.24, 29.08. HRMS (ESI): m/z ([M+Na]⁺) calcd. for $C_{10}H_{14}O_4Na$ 221.0784, found 221.0784. HPLC (Chiralcel AD-H column; 10% iPrOH/Hexane at 1 mL/min) enantiomeric excess determined at 250 nm; 16.3 min, 23.8 min.

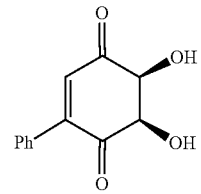

4d

¹H NMR (400 MHz, MeOD) δ 7.54 (dd, J=7.6, 1.7 Hz, 2H), 7.48-7.40 (m, 3H), 6.93 (s, 1H), 4.72 (d, J=3.2 Hz, 1H), 4.58 (d, J=3.0 Hz, 1H). ¹³C NMR (101 MHz, MeOD) δ 198.20, 198.02, 151.19, 135.58, 134.53, 131.33, 130.07, 129.54, 79.42, 77.83. HRMS (ESI): m/z ([M+H]⁺) calcd. for $C_{12}H_{11}O_4$ 219.0652, found 219.0653. HPLC (Chiralcel AD-H column; 10% iPrOH/Hexane at 1 mL/min) enantiomeric excess determined at 250 nm; 31.9 min, 37.4 min.

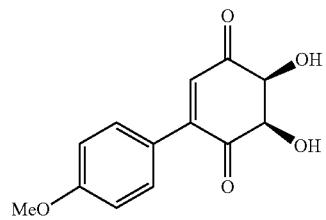

4e

¹H NMR (400 MHz, CDCl₃) δ 7.57-7.51 (m, 2H), 7.00-6.93 (m, 3H), 4.80 (d, J=3.4 Hz, 1H), 4.63 (d, J=3.1 Hz, 1H), 3.86 (s, 3H), 3.60 (s, 1H), 3.44 (s, 1H). ¹³C NMR (101 MHz, CDCl₃) δ 196.89, 195.05, 162.31, 149.52, 131.95, 130.88, 124.29, 114.56, 75.88, 55.61. HRMS (ESI): m/z ([M+H]⁺) calcd. for $C_{13}H_{13}O_5$ 249.0757, found 249.0755. HPLC (Chiralcel AD-H column; 10% iPrOH/Hexane at 1 mL/min) enantiomeric excess determined at 250 nm; 56.6 min, 72.0 min.

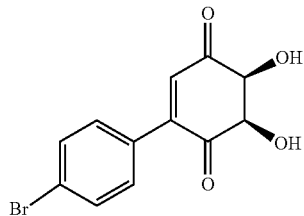

4f

¹H NMR (500 MHz, DMSO) δ 7.67 (d, J=8.3 Hz, 2H), 7.48 (d, J=8.4 Hz, 2H), 7.00 (s, 1H), 6.16 (dd, J=20.6, 5.2 Hz, 2H), 4.65 (s, 1H), 4.52 (s, 1H). ¹³C NMR (126 MHz, DMSO) δ 197.25, 197.14, 147.59, 134.75, 132.20, 131.49, 131.03, 123.80, 77.95, 76.54. HRMS (ESI): m/z ([M+H]⁺) calcd. for $C_{12}H_{10}BrO_4$ 296.9757, found 296.9757. HPLC (Chiralcel AD-H column; 10% iPrOH/Hexane at 1 mL/min) enantiomeric excess determined at 230 nm; 41.5 min, 52.8 min.

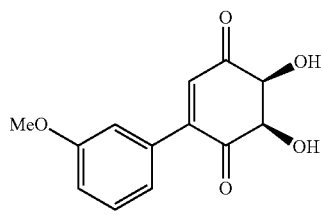

4g

¹H NMR (500 MHz, DMSO) δ 7.37 (t, J=7.8 Hz, 1H), 7.10-7.03 (m, 3H), 6.98 (s, 1H), 4.65 (d, J=3.1 Hz, 1H), 4.50 (d, J=3.0 Hz, 1H), 3.79 (s, 3H). ¹³C NMR (101 MHz, DMSO) δ 197.53, 197.19, 159.08, 148.67, 134.52, 134.36, 129.55, 115.87, 114.13, 78.12, 76.52, 55.23. HRMS (ESI): m/z ([M+Na]⁺) calcd. for $C_{13}H_{12}O_5Na$ 271.0577, found 271.0577. HPLC (Chiralcel AD-H column; 10% iPrOH/Hexane at 1 mL/min) enantiomeric excess determined at 210 nm; 44.0 min, 60.9 min.

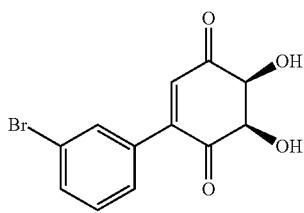

4h

¹H NMR (500 MHz, DMSO) δ 7.72-7.65 (m, 2H), 7.53 (d, J=7.9 Hz, 1H), 7.43 (t, J=7.9 Hz, 1H), 7.03 (s, 1H), 4.65 (d, J=3.1 Hz, 1H), 4.52 (d, J=3.1 Hz, 1H). ¹³C NMR (101 MHz, DMSO) δ 197.17, 197.10, 147.18, 135.34, 135.32, 132.66, 131.51, 130.63, 127.98, 121.54, 77.93, 76.56. HRMS (ESI): m/z ([M+Na]⁺) calcd. for $C_{12}H_9BrO_4Na$ 318.9576, found 318.9576. HPLC (Chiralcel AD-H column; 10% iPrOH/Hexane at 1 mL/min) enantiomeric excess determined at 280 nm; 39.2 min, 41.8 min.

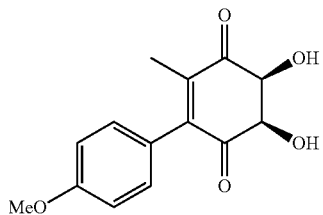

4i

¹H NMR (500 MHz, CDCl₃) δ 7.15 (d, J=8.6 Hz, 2H), 6.97 (d, J=8.6 Hz, 2H), 4.72 (dd, J=13.3, 3.1 Hz, 2H), 3.85 (s, 3H), 3.46 (d, J=38.1 Hz, 2H), 2.06 (s, 3H). ¹³C NMR (126 MHz, CDCl₃) δ 196.40, 195.83, 160.44, 147.14, 144.87, 131.15, 124.69, 113.99, 76.57, 75.91, 55.48, 14.95. HRMS (ESI): m/z ([M+H]⁺) calcd. for $C_{14}H_{15}O_5$ 263.0914, found 263.0912. HPLC (Chiralcel AD-H column; 10% iPrOH/Hexane at 1 mL/min) enantiomeric excess determined at 250 nm; 48.3 min, 56.6 min.

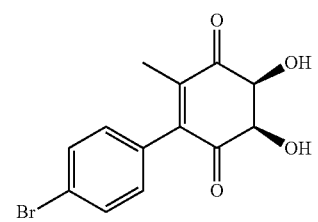

4j

¹H NMR (500 MHz, MeOD) δ 7.60 (d, J=8.1 Hz, 2H), 7.13 (d, J=8.1 Hz, 2H), 4.65 (d, J=4.0 Hz, 2H), 1.92 (s, 3H). ¹³C NMR (126 MHz, MeOD) δ 198.50, 197.26, 147.02, 146.65, 134.01, 132.39, 132.32, 123.73, 78.46, 77.80, 14.59. HRMS (ESI): m/z ([M+Na]⁺) calcd. for $C_{13}H_{11}BrO_4Na$ 332.9733, found 332.9730. HPLC (Chiralcel AD-H column; 10% iPrOH/Hexane at 1 mL/min) enantiomeric excess determined at 230 nm; 32.5 min, 36.0 min.

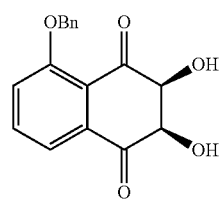

4k

¹H NMR (400 MHz, MeOD) δ 7.74-7.63 (m, 2H), 7.55 (d, J=7.5 Hz, 2H), 7.50 (d, J=7.8 Hz, 1H), 7.37 (t, J=7.5 Hz, 2H), 7.29 (t, J=7.3 Hz, 1H), 5.27 (s, 2H), 4.67 (dd, J=17.5, 2.7 Hz, 2H). ¹³C NMR (126 MHz, MeOD) δ 159.82, 137.91, 137.16, 136.21, 129.50, 128.86, 128.11, 124.17, 121.04, 120.21, 80.28, 78.33, 71.85.

4l

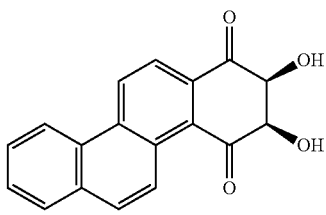

¹H NMR (400 MHz, DMSO) δ 9.33 (d, J=8.7 Hz, 1H), 8.96 (dd, J=9.5, 6.0 Hz, 2H), 8.24 (d, J=8.7 Hz, 1H), 8.13 (d, J=9.4 Hz, 1H), 8.09 (dd, J=6.2, 3.1 Hz, 1H), 7.84-7.77 (m, 2H), 6.27 (s, 2H), 4.84 (d, J=3.2 Hz, 2H). ¹³C NMR (101 MHz, DMSO) δ 198.83, 195.85, 134.02, 133.57, 131.95, 131.24, 130.33, 129.04, 129.00, 128.83, 128.68, 128.50, 127.79, 123.88, 123.43, 123.25, 79.87, 77.13. HRMS (ESI): m/z ([M+H]$^+$) calcd. for $C_{18}H_{13}O_4$ 293.0808, found 293.0803. HPLC (Chiralcel AD-H column; 10% iPrOH/Hexane at 1 mL/min) enantiomeric excess determined at 250 nm; 68.7 min, 88.6 min.

4m

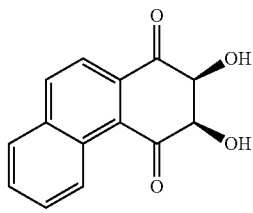

¹H NMR (500 MHz, CDCl$_3$) δ 9.16 (d, J=8.5 Hz, 1H), 8.15 (t, J=20.7 Hz, 2H), 7.93 (d, J=8.0 Hz, 1H), 7.72 (dt, J=14.8, 7.1 Hz, 2H), 4.92 (dd, J=19.6, 2.7 Hz, 2H). ¹³C NMR (126 MHz, CDCl$_3$) δ 197.18, 194.85, 136.91, 135.85, 133.72, 130.98, 130.08, 129.70, 129.66, 128.82, 127.59, 122.39, 78.38, 76.87. HRMS (ESI): m/z ([M+Na]$^+$) calcd. for $C_{14}H_{10}O_4Na$ 265.0471, found 265.0473. HPLC (Chiralcel AD-H column; 10% iPrOH/Hexane at 1 mL/min) enantiomeric excess determined at 210 nm; 39.1 min, 55.8 min.

4n

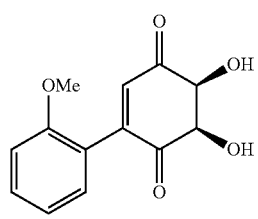

4l

¹H NMR (500 MHz, MeOD) δ 7.46-7.41 (m, 1H), 7.24 (dd, J=7.5, 1.5 Hz, 1H), 7.05 (d, J=8.4 Hz, 1H), 7.02 (t, J=7.5 Hz, 1H), 6.76 (s, 1H), 4.78 (d, J=3.4 Hz, 1H), 4.52 (d, J=3.3 Hz, 1H), 3.77 (s, 3H). ¹³C NMR (101 MHz, MeOD) δ 197.87, 197.73, 158.52, 152.33, 136.42, 132.75, 131.33, 124.86, 121.90, 112.56, 78.73, 78.04, 56.23. HRMS (ESI): m/z ([M+Na]$^+$) calcd. for $C_{13}H_{12}O_5Na$ 271.0577, found 271.0578. HPLC (Chiralcel AD-H column; 10% iPrOH/Hexane at 1 mL/min) enantiomeric excess determined at 230 nm; 32.5 min, 36.0 min.

5d

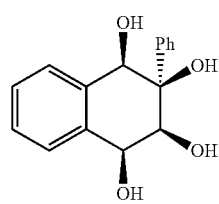

¹H NMR (600 MHz, DMSO) δ 7.52 (t, J=7.1 Hz, 2H), 7.39 (d, J=7.5 Hz, 1H), 7.37-7.29 (m, 4H), 7.21 (t, J=7.3 Hz, 1H), 5.37 (d, J=7.3 Hz, 1H), 5.24 (s, 1H), 4.98 (d, J=9.5 Hz, 1H), 4.77 (d, J=9.5 Hz, 1H), 4.69 (d, J=7.6 Hz, 1H), 4.59 (dd, J=7.2, 4.2 Hz, 1H), 4.13 (dd, J=7.6, 4.2 Hz, 1H). ¹³C NMR (126 MHz, DMSO) δ 144.60, 138.34, 136.38, 129.19, 127.81, 127.54, 127.35, 127.08, 126.38, 126.00, 79.36, 73.91, 71.62, 70.67. HRMS (ESI): m/z ([M+Na]$^+$) calcd. for $C_{16}H_{16}O_4Na$ 295.0941, found 295.0938. HPLC (Chiralcel AD-H column; 15% iPrOH/Hexane at 1 mL/min) enantiomeric excess determined at 250 nm; 16.2 min, 34.6 min.

AD Reaction of Substituted Benzoquinones and Naphthoquinones

Figure 1B:
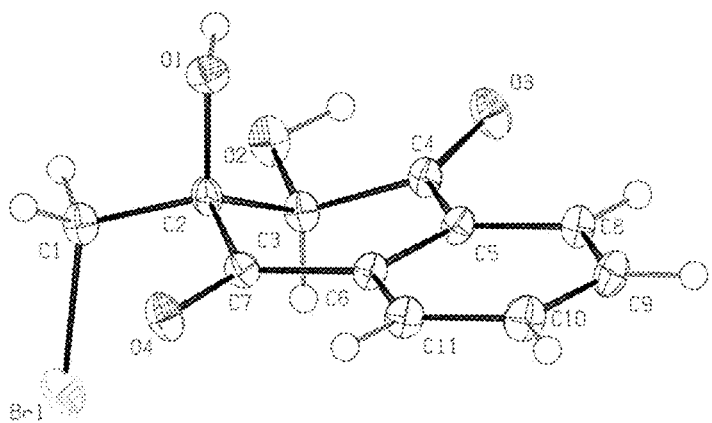
Figure 1C:
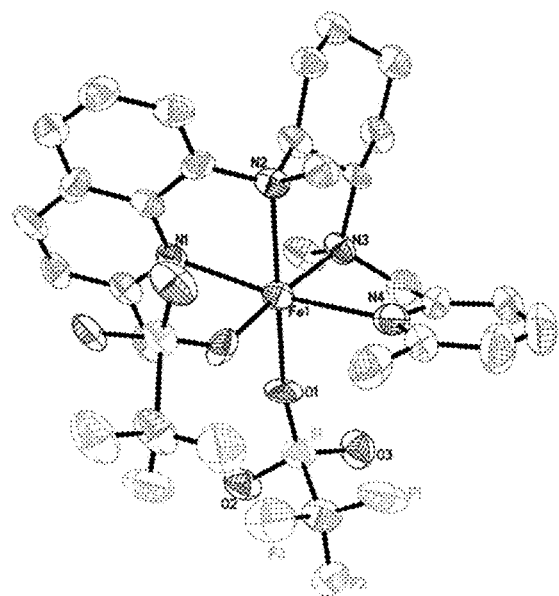

Under the reaction conditions determined in Example 1, the AD reactions of substituted p-benzo- and p-naphthoquinones (1b-1v) were explored using two exemplary catalysts Fe$^{II}$(L4)(OTf)$_2$ and Fe$^{II}$(L9)(OTf)$_2$, and the results are shown in Table 5 and Table 6. The absolute configurations of products 2u and 2m and catalyst Fe$^{II}$(L9)(OTf)$_2$ were determined by X-ray crystallography (FIGS. 1A-1C, respectively). For unsymmetrically substituted quinones, AD reaction generally occurs at the less sterically hindered C=C double bond (1c, 1e, 1g-1v), except for if where the cis-dihydroxylation occurred on the C=C double bond with electron-deficient group, which is consistent with our previous results. For 2-methyl substituted naphthoquinones, cis-diols(1i-1k) were obtained in good to high yields and ees (82-99% yield, 80-98.1% ee). Hydroxyl group is compatible with the AD reaction (11). An array of cis-diols of 2-benzyl- and 2-aryl-substituted naphthoquinones were obtained in 72-99% yield and 96.9-99.5% ee (1p-1v).

TABLE 5

AD reactions of substituted 1,4-benzoquinones and 1,4-naphthaquinones using Fe$^{II}$(L4)(OTf)$_2$.

| Entry[a] | Substrate | cis-diol | Conv. (%)[b] | Yield (%)[c] | ee (%)[d] |
|---|---|---|---|---|---|
| 1 | 1a | 2a | 100 | 85 | 99.6 |

TABLE 5-continued

AD reactions of substituted 1,4-benzoquinones and 1,4-naphthaquinones using Fe[II](L4)(OTf)$_2$.

| Entry[a] | Substrate | cis-diol | Conv. (%)[b] | Yield (%)[c] | ee (%)[d] |
|---|---|---|---|---|---|
| 2 | 1b | 2b | 93 | 66 | 83.5 |
| 3 | 1c | 2c | 71 | 84 | 97.5 |
| 4[e] | 1d | 2d | 100 | 70 | 98.5 |
| 5 | 1e | 2e | 100 | 85 | >99.9 |
| 6 | 1f | 2f | 100 | 90 | >99.9 |
| 7 | 1g | 2g | 100 | 53 | >99.9 |

TABLE 5-continued
AD reactions of substituted 1,4-benzoquinones and 1,4-naphthaquinones using Fe$^{II}$(L4)(OTf)$_2$.
| Entry[a] | Substrate | cis-diol | Conv. (%)[b] | Yield (%)[c] | ee (%)[d] |
|---|---|---|---|---|---|
| 8 | 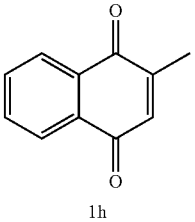 1h | 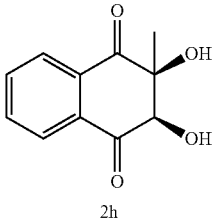 2h | 100 | 90 | 97.9 |
| 9 | 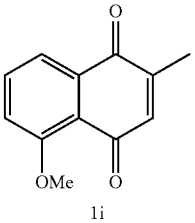 1i | 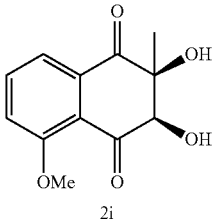 [SMILES: COc1cccc2c1C(=O)[C@H](O)[C@](C)(O)C2=O] 2i | 100 | 84 | 80 |
| 10 | 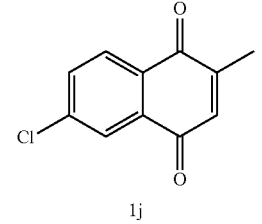 1j | 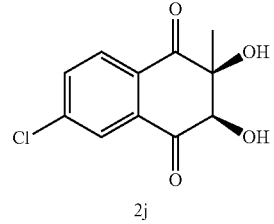 [SMILES: C[C@@]1(O)C(=O)c2ccc(Cl)cc2C(=O)[C@@H]1O] 2j | 100 | 93.4 | 97 |
| 11 | 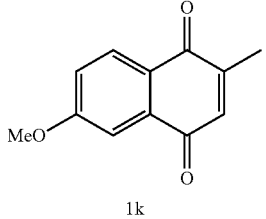 1k | 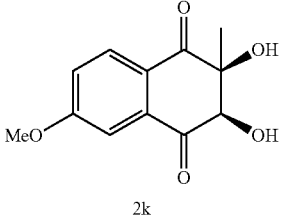 [SMILES: COc1ccc2c(c1)C(=O)[C@H](O)[C@](C)(O)C2=O] 2k | 88 | 99 | 98.1 |
| 12 | 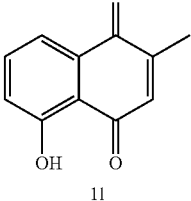 1l | 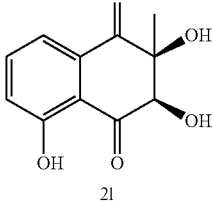 2l | 100 | 80 | 97.3 |
| 13 | 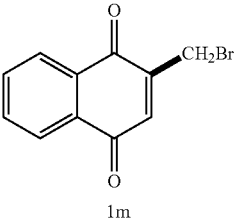 1m | 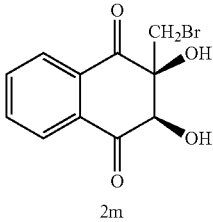 2m | 100 | 90 | 99.1 |

TABLE 5-continued

AD reactions of substituted 1,4-benzoquinones and 1,4-naphthaquinones using Fe[II](L4)(OTf)$_2$.

| Entry[a] | Substrate | cis-diol | Conv. (%)[b] | Yield (%)[c] | ee (%)[d] |
|---|---|---|---|---|---|
| 14 | 1n | 2n | 65 | 96 | 98.3 |
| 15 | 1o | 2o | 100 | 99 | 93.3 |
| 16 | 1p | 2p | 87 | 92 | 97.5 |
| 17 | 1q | 2q | 100 | 93 | 97.1 |
| 18[e] | 1r | 2r | 100 | 99 | 98 |
| 19[e] | 1s | 2s | 100 | 93 | 96.9 |

TABLE 5-continued

AD reactions of substituted 1,4-benzoquinones and 1,4-naphthaquinones using Fe$^{II}$(L4)(OTf)$_2$.

| Entry[a] | Substrate | cis-diol | Conv. (%)[b] | Yield (%)[c] | ee (%)[d] |
|---|---|---|---|---|---|
| 20[e] | 1t | 2t | 100 | 93 | 99.5 |
| 21[e] | 1u | 2u | 99 | 96 | 98.5 |

[a]Reaction conditions: quinones (0.2 mmol), Fe$^{II}$(L4)(OTf)$_2$ (3 mol %), H$_2$O$_2$ (30% aq, 3 equiv, dissolved in 1 mL CD$_3$OD) and CD$_3$OD (2 mL) under air at room temperature.
[b]Substrate conversion determined by crude $^1$H NMR.
[c]Cis-diol yield based on substrate conversion determined by crude $^1$H NMR, PhTMS as internal standard.
[d]Enantiomeric excess (ee) determined by chiral HPLC.
[e]CD$_3$OD (8 mL).

TABLE 6

AD reactions of substituted 1,4-benzoquinones and 1,4-naphthaquinones using catalyst Fe$^{II}$(L9)(OTf)$_2$.

| Entry[a] | Substrate | cis-diol | Conv. (%)[b] | Yield (%)[c] | ee (%)[d] |
|---|---|---|---|---|---|
| 1 | 1a | 2a | 100 | 81 | 96 |
| 2 | 1b | 2b | 83 | 75 | 82 |

TABLE 6-continued

AD reactions of substituted 1,4-benzoquinones and 1,4-naphthaquinones using catalyst Fe$^{II}$(L9)(OTf)$_2$.

| Entry[a] | Substrate | cis-diol | Conv. (%)[b] | Yield (%)[c] | ee (%)[d] |
|---|---|---|---|---|---|
| 3 | 1c | 2c | 85 | 78 | 92 |
| 4 | 1h | 2h | 88 | 81 | 92 |
| 5 | 1j | 2j | 85 | 88 | 94 |
| 6 | 1k | 2k | 60 | 82 | 93 |
| 7 | 1l | 2l | 90 | 87 | 95.3 |
| 8 | 1m | 2m | 95 | 85 | 85 |

TABLE 6-continued
AD reactions of substituted 1,4-benzoquinones and 1,4-naphthaquinones using catalyst Fe[II](L9)(OTf)$_2$.
| Entry[a] | Substrate | cis-diol | Conv. (%)[b] | Yield (%)[c] | ee (%)[d] |
|---|---|---|---|---|---|
| 9 | 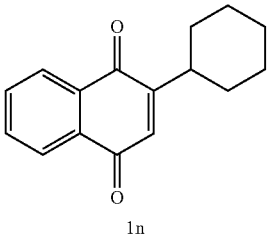 [SMILES: O=C1C=C(C2CCCCC2)C(=O)c2ccccc21] 1n | 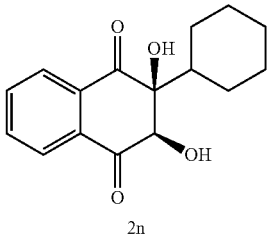 [SMILES: O=C1c2ccccc2C(=O)[C@](O)(C2CCCCC2)[C@H]1O] 2n | 76 | 72 | 96 |
| 10 | 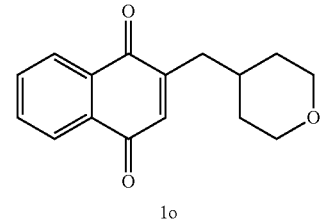 [SMILES: O=C1C=C(CC2CCOCC2)C(=O)c2ccccc21] 1o | 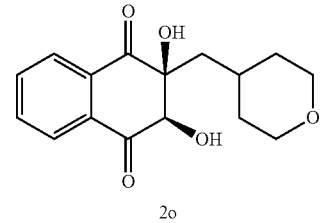 [SMILES: O=C1c2ccccc2C(=O)[C@](O)(CC2CCOCC2)[C@H]1O] 2o | 87 | 80 | 90 |
| 11 | 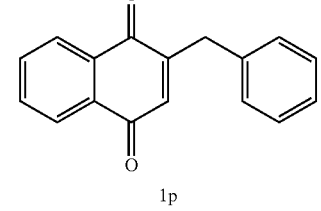 1p | 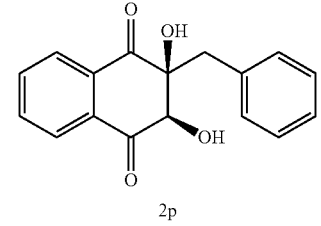 [SMILES: O=C1c2ccccc2C(=O)[C@](O)(Cc2ccccc2)[C@H]1O] 2p | 76 | 72 | 96 |
| 12 | 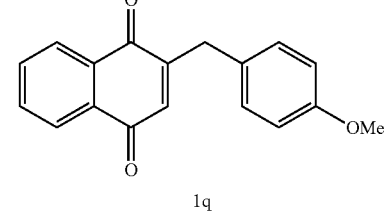 1q | 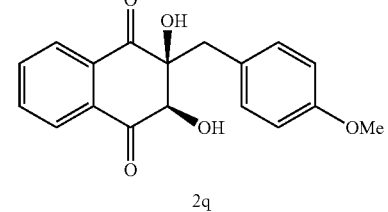 2q | 90 | 85 | 94 |
| 13 | 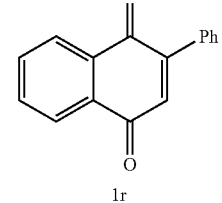 1r | 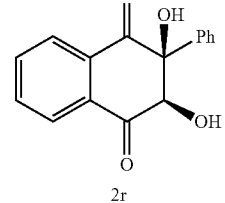 2r | 88 | 86 | 90 |
| 14 | 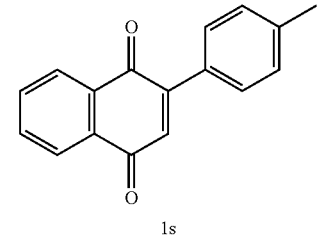 [SMILES: Cc1ccc(C2=CC(=O)c3ccccc3C2=O)cc1] 1s | 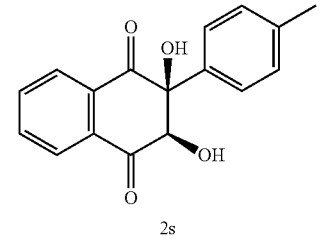 [SMILES: Cc1ccc([C@@]2(O)C(=O)c3ccccc3C(=O)[C@@H]2O)cc1] 2s | 95 | 91 | 91 |

TABLE 6-continued

AD reactions of substituted 1,4-benzoquinones and 1,4-naphthaquinones using catalyst Fe$^{II}$(L9)(OTf)$_2$.

| Entry[a] | Substrate | cis-diol | Conv. (%)[b] | Yield (%)[c] | ee (%)[d] |
|---|---|---|---|---|---|
| 15 | 1t | 2t | 91 | 88 | 91 |
| 16 | 1u | 2u | 96 | 92 | 90 |
| 17 | 1v | 2v | 96 | 92 | 92 |

[a]Reaction conditions: quinones (0.2 mmol), Fe$^{II}$(L9)(OTf)$_2$ (5 mol %), H$_2$O$_2$ (30% aq, 3 equiv, dissolved in 1 mL CH$_3$OH) and CH$_3$OH (2 mL) under air at room temperature.
[b]Substratec onversion determined by crude $^1$H NMR.
[c]Cis-diol yield based on substrate conversion determined by crude $^1$H NMR, PhTMS as internal standard.
[d]Enantiomeric excess (ee) determined by chiral HPLC.

The results in Table 7 show that substituent(s) on the distal C═C double bond may have an enantiomeric control over dihydroxylation on the non-substituted C═C bond in several mono- and disubstituted p-quinones, with the ee being positively correlated with the size of the remote substituent(s). The electronic effect of substrates was investigated. Monosubstituted p-benzoquinones with Br and methoxy on different positions of benzene ring (3e-3j) proceeded well (45%-66% yield, 86.5%-96.9% ee). For disubstituted p-benzoquinones (3i-j), relatively lower ee values were obtained when compared to 3d, likely due to the smaller difference between the two substituents on the distal C═C bond (methyl and aryl). Such a remote effect is generally weaker when it comes to p-naphthoquinone substrates, where the corresponding cis-diol products 4k-4m were obtained in 35-69% ee. The lower ee of 3k is due to its planar structure than benzoquinone and the low steric hindrance (it has only two substituents on the double bond comparable to trisubstituted naphthoquinone), leading to a lower recognition by Fe(L4)(OTf)$_2$.

TABLE 7

AD reactions of quinones bearing remote substituents

| Entry[a] | Substrate | cis-diol | Conv. (%)[b] | Yield (%)[c] | ee (%)[d] |
|---|---|---|---|---|---|
| 2 | 3b | 4b | 80 | 50 | 60.0 |

TABLE 7-continued
AD reactions of quinones bearing remote substituents
| Entry[a] | Substrate | cis-diol | Conv. (%)[b] | Yield (%)[c] | ee (%)[d] |
|---|---|---|---|---|---|
| 3 | 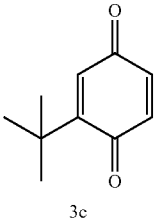 3c | 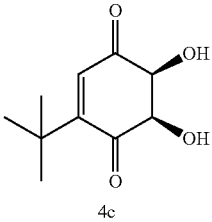 4c | 100<br>99* | 61<br>96* | 95.9<br>90* |
| 4[e] | 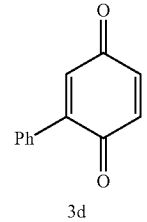 3d | 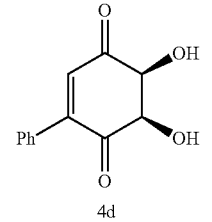 4d | 100 | 50 | 90.5 |
| 5 | 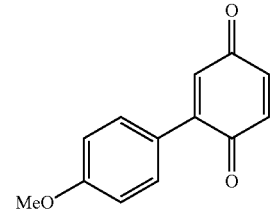 3e | 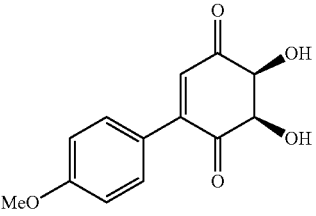 4e | 100 | 50 | 86.5 |
| 6 | 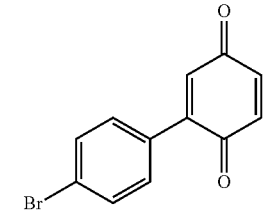 3f | 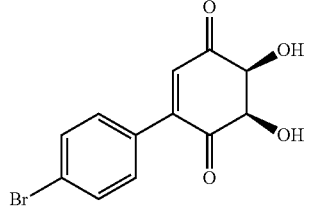 4f | 100 | 50 | 96.7 |
| 7 | 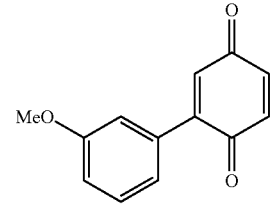 3g | 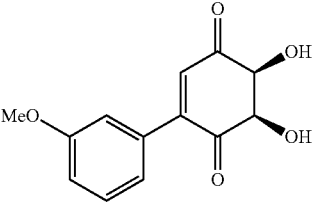 4g | 100 | 45 | 94.6 |
| 8 | 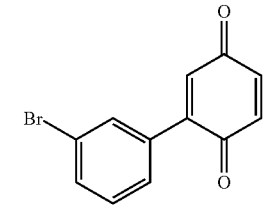 3h | 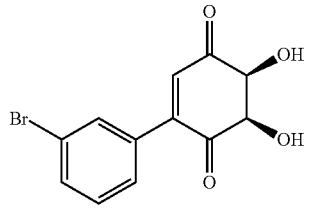 4h | 100 | 44 | 95.9 |

TABLE 7-continued

AD reactions of quinones bearing remote substituents

| Entry[a] | Substrate | cis-diol | Conv. (%)[b] | Yield (%)[c] | ee (%)[d] |
|---|---|---|---|---|---|
| 9 | 3i | 4i | 100 | 61 | 77 |
| 10 | 3j | 4j | 100 | 66 | 80 |
| 11 | 3k | 4k | 100 | 85 | 35 |
| 12[e] | 3l | 4l | 60 | 98 | 69 |
| 13[e] | 3m | 4m | 100 | 82 | 66.5 |

TABLE 7-continued

AD reactions of quinones bearing remote substituents

| Entry[a] | Substrate | cis-diol | Conv. (%)[b] | Yield (%)[c] | ee (%)[d] |
|---|---|---|---|---|---|
| 14 | 3n (quinone with OMe-phenyl substituent) | 4n (cis-diol product) | 100 | 55 | 93.5 |

[a]Reaction conditions: quinones (0.2 mmol), Fe$^{II}$(L4)(OTf)$_2$ (3 mol %), HO$_2$ (30% aq, 3 equiv, dissolved in 1 mL CD$_3$OD), and CD$_3$OD (2 mL) under air at room temperature.
*Reaction conditions: quinones (0.2 mmol), Fe$^{II}$(L9)(OTf)$_2$ (5 mol %), H$_2$O$_2$ (30% aq, 3 equiv, dissolved in1 mL CH$_3$OH), and CH$_3$OH (2 mL) under air at room temperature for 1 h.
[b]Substrate conversion determined by crude $^1$H NMR.
[c]Cis-diol yield based on substrate conversion determined by crude $^1$H NMR, PhTMS as internal standard.
[d]Enantiomeric excess (ee) determined by chiral HPLC.
[e]CD$_3$OD (8 mL).

This quinone AD reaction can be readily scaled up to gram scale with vitamin K3 as the substrate. As shown in Scheme 5, a one-pot AD reaction with 1 g of vitamin K3 produces the corresponding cis-diol product in 90% yield with 99.8% ee.

Triols and tetraols are important units in natural products. Reduction of the chiral cis-diol products can lead to valuable polyols with specific stereochemistry. Using different reductants, 1,2,3-triol and 1,2,3,4-tetraol were obtained (Scheme 6). When using NaBH$_4$, highly enantioselective triol (5a) was readily obtained (95% yield, 98.1% ee, >20:1 dr). With H$_2$ and Pd/C catalyst, tetraols (5b-c) were obtained in 94% yield, with low distereoselectivity. For cis-diols of 2-phenyl-substituted p-naphthoquinone, the dr value increased to 12.5:1 with 98.5% ee.

Examples 3. Comparison Between the Exemplary Fe(II) Complex and Os Catalytic Systems for Asymmetric Cis-Dihydroxylation of Quinones

Materials and Methods

AD reactions of quinone (1c, 1h, 3c) catalyzed by the Fe$^{II}$(L4)(OTf)$_2$ or Fe$^{II}$(L9)(OTf)$_2$ are compared with the same reaction catalyzed by known osmium catalyst. For AD-mix-beta, the procedure in Sharples, et al., *J. Org. Chem.*, 1992, 57, 2768-2771 was followed at a reduced scale (reduced by 50%, amounts of reactants shown in Tables 8 and 9). For OsO$_4$, the procedure for Spirocyclic lactone 15 in the supporting information of Honda, et al., *Organic Letters*, 2001, 3, 18, 2899-2902 was followed at a reduced scale (amounts of reactants shown in Table 8).

Results

This is the first report of asymmetric cis-dihydroxylation of quinones. Comparison with Osmium-catalyzed AD reaction of quinones (1c, 1h, 3c) has been performed. Cis-diols of quinones could not be obtained by commercially available AD-mix-beta. For 1c, 1h substrates, osmium tetroxide gave the cis-diols in low yield (15-20%) with low ee (17%-26.7%). Additionally, AD reaction using osmium tetroxide could not produce the cis-diols of 3c.

TABLE 8

Comparison between [Fe$^{II}$(L4)(OTf)$_2$]/H$_2$O$_2$ or [Fe$^{II}$(L9)(OTf)$_2$]/H$_2$O$_2$ and Os catalytic systems for quinone AD reactions[a]

| Substrate | Catalytic system | Yield (%)[b] | r.r.[c] | ee (%)[d] |
|---|---|---|---|---|
| trimethyl-p-benzoquinone | Fe$^{II}$(L4)(OTf)$_2$ | 84 | Single isomer | 97.5 |
|  | Fe$^{II}$(L9)(OTf)$_2$[e] | 66 | >20/1 | 92.0 |
|  | OsO$_4$ | 15 | 10/1 | 26.7 |
|  | AD-mix-beta | 0 | — | — |
| 2-methyl-1,4-naphthoquinone | Fe$^{II}$(L4)(OTf)$_2$ | 90 | — | 97.0 |
|  | Fe$^{II}$(L9)(OTf)$_2$[e] | 71 | — | 92.0 |
|  | OsO$_4$ | 20 | — | 17.0 |
|  | AD-mix-beta | 0 | — | — |
| 2-tert-butyl-p-benzoquinone | Fe$^{II}$(L4)(OTf)$_2$ | 61 | >20/1 | 95.9 |
|  | Fe$^{II}$(L9)(OTf)$_2$[e] | 95 | >20/1 | 90 |
|  | OsO4 | 0 | — | — |
|  | AD-mix-beta | 0 | — | — |

[a]Reaction conditions: (i) quinones (0.2 mmol), F$^{II}$(L4)(OTf)$_2$ (3 mol %) or Fe$^{II}$(L9)(OTf)$_2$ (5 mol %), H$_2$O$_2$ (3 equiv) in 1 mL CD$_3$OD, and CD$_3$OD (2 mL) under air at room temperature. (ii) For OsO$_4$ method, quinone (1 mmol), OsO$_4$ (3.25 mol %), (DHQ)2PHAL (30.25 mol %), NMO (1.3 equiv), in 20 mL of 1:1 acetone/water mixture under air at room temperature, (iii) for AD-mix method: standard conditions described in the literature: quinone (0.5 mmol), 0.7 g AD-mix-β (0.2 mol %), 2.5 mL tert-butyl alcohol, 2.5 mL water, from 0° C. to room temperature, under air.
[b]cis-diols yield based on conversion determined by crude $^1$H NMR.
[c]r.r. = regioselectivity
[d]Enantiomeric excess (ee) determined by chiral HPLC.
[e]Fe$^{II}$(L9)(OTf)$_2$ (5 mol %).

In summary, the first Fe-catalyzed asymmetric cis-dihydroxylation reaction of organic quinones was developed. This method provides a simple, practical, and sustainable access to chiral cis-diols of various mono-, di-, and trisubstituted p-quinones, with up to 99% yield and up to 99.9% ee. Further, the Fe catalyst was found to be superior in this quinone AD reaction to the commercial AD-mix catalysts or other $OsO_4$-based protocols, which further demonstrates the application of Fe-catalyzed AD reactions in practical organic synthesis.

REFERENCES

Kolb, et al., *Chemical Reviews* 1994, 94, 2483 2547.
Bataille and Donohoe, *Chem Soc Rev* 2011, 40, 114-128.
Bebbington, *Chemical Society Reviews* 2017, 46, 5059-5109.
Ottenbacher, et al., *Russian Chemical Reviews* 2019, 88, 1094-1103.
Noe, et al., *Organic Reactions* 2005, 109-625.
Adolfsson and Zaitsev, *Synthesis* 2006, 2006, 1725-1756.
Sugimoto, et al., *Journal of the American Chemical Society* 2012, 134, 19270-19280.
Bhunnoo, et al., *Angewandte Chemie International Edition* 2002, 41, 3479-3480.
Neisius and Plietker, *The Journal of Organic Chemistry* 2008, 73, 3218-3227.
Chow, et al., *Chemical Communications* 2011, 47, 11204-11206.
Fujita, et al., *Chemical Communications* 2011, 47, 3983-3985.
Toribatake and Nishiyama, *Angew Chem Int Ed* 2013, 52, 11011-11015.
Wang, et al., *Journal of the American Chemical Society* 2015, 137, 10677-10682.
Wang, et al., *J Am Chem Soc* 2015, 137, 10677-10682.
Boyd, et al., *Current Opinion in Biotechnology* 2001, 12, 564-573.
Wolfe and Lipscomb, *Journal of Biological Chemistry* 2003, 278, 829-835.
Bruijnincx, et al., *Chemical Society Reviews* 2008, 37, 2716-2744.
Barry and Challis, *ACS catalysis* 2013, 3, 2362-2370.
Gally, et al., *Angewandte Chemie International Edition* 2015, 54, 12952-12956.
Özgen and Schmidt, Biocatalysis, 2019, 57-82.
Oldenburg, et al., *Journal of the American Chemical Society* 2005, 127, 15672-15673.
Chow, et al., *Journal of the American Chemical Society* 2010, 132, 13229-13239.
Talsi and Bryliakov, *Coordination Chemistry Reviews* 2012, 256, 1418-1434.
Moelands, et al., *Inorganic Chemistry* 2013, 52, 7394-7410.
Prat, et al., *Inorganic Chemistry* 2013, 52, 9229-9244.
Prat, et al., *Advanced Synthesis & Catalysis* 2013, 355, 947-956.
Borrell and Costas, *J Am Chem Soc* 2017, 139, 12821-12829.
Olivo, et al., *Journal of Biological Inorganic Chemistry* 2017, 22, 425-452.
Borrell and Costas, *ACS Sustainable Chemistry & Engineering* 2018, 6, 8410-8416.
Costas, et al., *Journal of the American Chemical Society* 2001, 123, 6722-6723.
Suzuki, et al., *Angew Chem Int Ed* 2008, 47, 1887-1889.
Zang, et al., *Angewandte Chemie International Edition* 2016, 55, 10253-10257.
Wei, et al., *Angewandte Chemie International Edition* 2020, 59, 16561-16571.
Sharpless, et al., *The Journal of Organic Chemistry* 1992, 57, 2768-2771.
Veldkamp and Frenking, *JACS* 1994, 116, 4937-4946.
Hussein, et al., *The Journal of Organic Chemistry* 2019, 84, 15173-15183.
Jones, et al., Maloney, *Journal of Medicinal Chemistry* 1986, 29, 1504-1511.
Caldwell, et al., *Synlett* 2001, 2001, 1428-1430.
Cox and Danishefsky, *Organic Letters* 2001, 3, 2899-2902.
Siu, et al., *Angew Chem Int Ed* 2003, 42, 5629-5634.
Milic, et al., Solaja, *Steroids* 2005, 70, 922-932.
Henderson, et al., *The Journal of Organic Chemistry* 2006, 71, 2434-2444.
Watanabe, et al., *J Org Chem* 2010, 75, 5573-5579.
Adachi, et al., *Angew Chem Int Ed* 2013, 52, 2087-2091.
Novikov, et al., *Russian Chemical Bulletin* 2018, 67, 282-290.
Carless and Oak, *Chemical Communications* 1991, 61-62.
Patti, et al., *The Journal of Organic Chemistry* 1996, 61, 6458-6461.
Kadota, et al., *Organic Letters* 2001, 3, 1769-1772.
Hochalter, et al., *Chem Res Toxicol* 2011, 24, 262-268.
Adduci, et al., *Angew Chem Int Ed* 2014, 53, 1646-1649.
Wei, et al., *ACS Catalysis* 2015, 5, 4060-4065.
Southgate, et al., *Nat Chem* 2016, 8, 922-928.
Lowe, et al., *ACS Catalysis* 2018, 8, 8192-8198.
Sakai, et al., *J Nat Prod* 2018, 81, 1604-1609.
Mechsner, et al., *Bioorganic & Medicinal Chemistry* 2019, 27, 2991-2997.
Maeda, et al., *J Nat Prod* 2020, 83, 210-215.
Wang, et al., *Angewandte Chemie International Edition* 2020, 59, 18166-18171.
Zang, et al., *Angewandte Chemie International Edition* 2016, 55, 10253-10257.
Wei, et al., *Angewandte Chemie International Edition* 2020, 59, 16561-16571.
Suzuki, et al., *Angew Chem Int Ed* 2008, 47, 1887-1889.
Fujiwara, et al., *Journal of the American Chemical Society* 2011, 133, 3292-3295.
Rodo, et al., *European Journal of Organic Chemistry* 2016, 2016, 1982-1993.
Feng, et al., *Organic & Biomolecular Chemistry* 2018, 16, 2647-2665.
Viault, et al., *European Journal of Organic Chemistry* 2011, 2011, 1233-1241.

We claim:
1. A method for asymmetric cis-dihydroxylation of a quinone comprising:
(i) maintaining a reaction mixture at a temperature for a period of time sufficient to form a product,
wherein the reaction mixture comprises the quinone, one or more iron-based catalyst(s), and a solvent,
wherein the product comprises a cis-diol,
wherein the one or more iron-based catalyst(s) have the structure of:

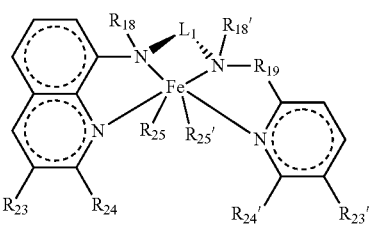

Formula XIII or a stereoisomer thereof, wherein:

(a) $L_1$ is

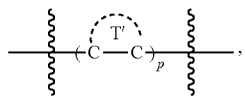

each occurrence of T' is an unsubstituted C6 monocyclic group and p is 1;

(b) $R_{18}$ and $R_{18}'$ are independently a substituted or unsubstituted C1-C6 alkyl;

(c) $R_{19}$ is an unsubstituted methylene;

(d) $R_{23}$ and $R_{23}'$ are hydrogen;

(e) $R_{24}$ and $R_{24}'$ are independently unsubstituted C1-C2 alkyl;

(d) $R_{25}$ and $R_{25}'$ are independently a triflate or halide; and (e) the substituents, when present, are independently a substituted or unsubstituted alkyl, a substituted or unsubstituted alkenyl, a substituted or unsubstituted alkynyl, a carbonyl, a halide, a hydroxyl, an aroxy, an alkylthio, an arylthio, a cyano, an isocyano, an alkoxyl, a nitro, a carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof; and wherein the cis-diol has an enantiomeric excess from about 80% to 100%, as determined by chiral HPLC.

2. The method of claim 1 further comprising adding an oxidant into the reaction mixture prior to and/or during step (i).

3. The method of claim 2, wherein the total mole amount of the oxidant in the reaction mixture is in a range from about 1-time to about 10-time of the total mole amount of the quinone.

4. The method of claim 1, wherein the quinone has a structure of:

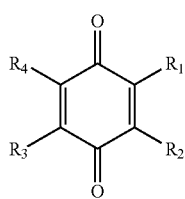

Formula I wherein:

(a) $R_1$-$R_4$ are independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and (b) the substituents, when present, are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

5. The method of claim 4, wherein at least one of $R_1$-$R_4$, at least two of $R_1$-$R_4$, or at least three of $R_1$-$R_4$ is an or are electron-donating group(s).

6. The method of claim 4, wherein at least one of $R_1$-$R_4$ is hydrogen.

7. The method of claim 4, wherein $R_1$-$R_4$ are independently a hydrogen, a substituted or unsubstituted alkyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic group, a substituted or unsubstituted aralkyl, an alkoxyl, or a carbonyl, or two neighboring R groups form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

8. The method of claim 4, wherein $R_1$-$R_4$ are independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

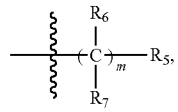

$R_5$ is a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ are independently a hydrogen or a substituted or unsubstituted alkyl, and m is an integer from 1 to 10, or two neighboring R groups together with the carbon atoms to which they are attached form a substituted or unsubstituted aryl or a substituted or unsubstituted polyaryl.

9. The method of claim 4, wherein $R_1$-$R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

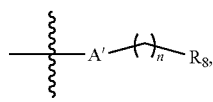

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or two neighboring R groups together with the carbon atoms to which they are attached form a substituted or unsubstituted aryl or a substituted or unsubstituted polyaryl.

10. The method of claim 4, wherein the quinone has a structure of:

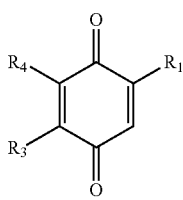

Formula III wherein $R_1$, $R_3$, and $R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

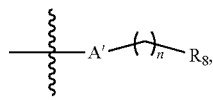

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or $R_3$ and $R_4$ together with the carbon atoms to which they are attached form a substituted or unsubstituted aryl or a substituted or unsubstituted polyaryl.

11. The method of claim 4, wherein the quinone has a structure of:

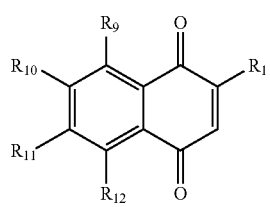

Formula IV wherein:
(a) $R_1$ is a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

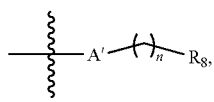

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8; and (b) $R_9$-$R_{12}$ are independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

12. The method of claim 11, wherein $R_9$-$R_{12}$ are independently a hydrogen, a halide, a hydroxyl, an aroxy, an alkoxyl, or $R_{11}$ and $R_{12}$ together with the carbon atoms to which they are attached form a substituted or unsubstituted cycloalkenyl, a substituted or unsubstituted polycycloalkenyl, a substituted or unsubstituted aryl or a substituted or unsubstituted polyaryl.

13. The method of claim 4, wherein the quinone has a structure of:

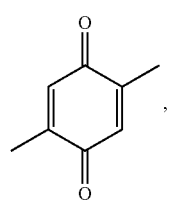

1a

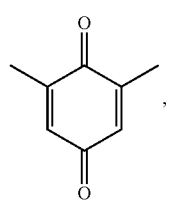

1b

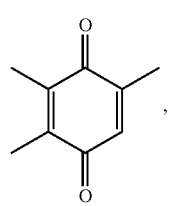

1c

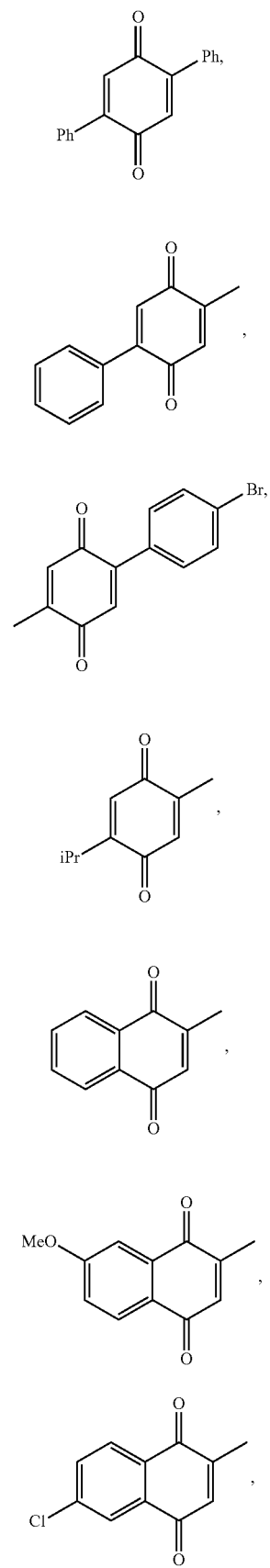
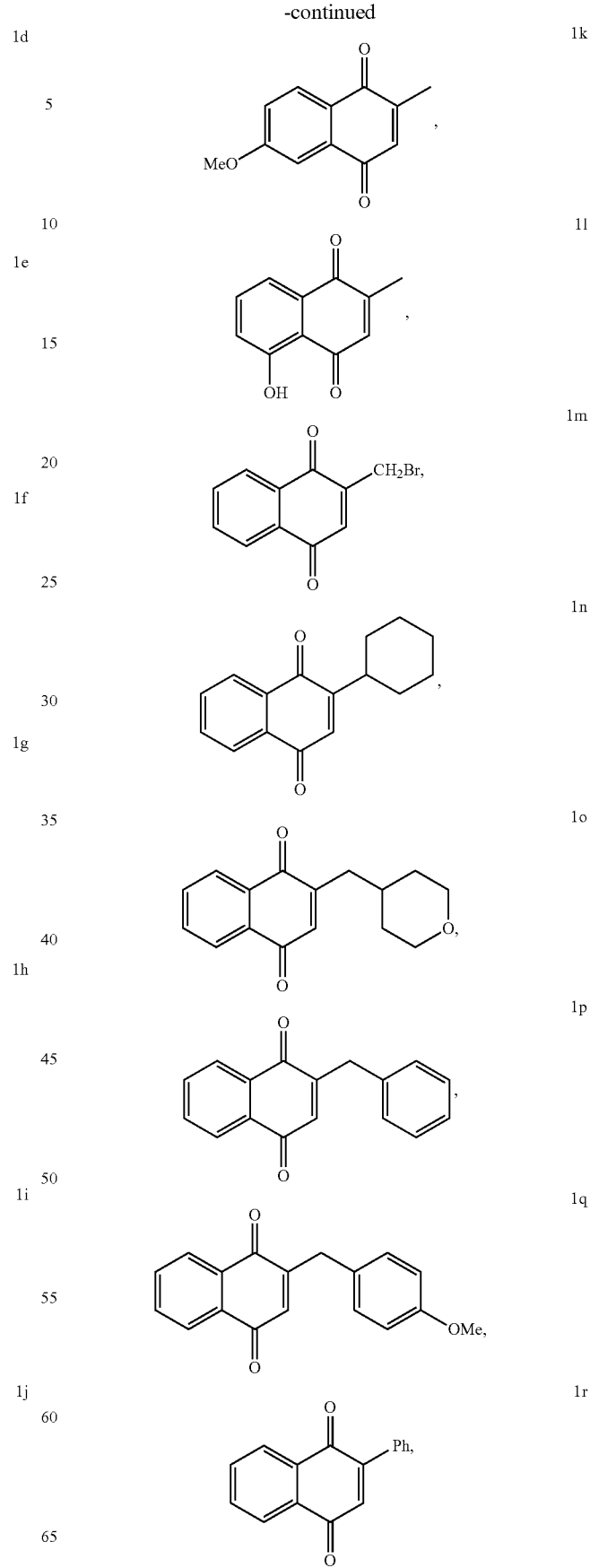

-continued
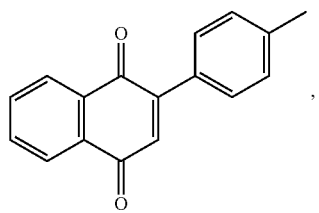  1s
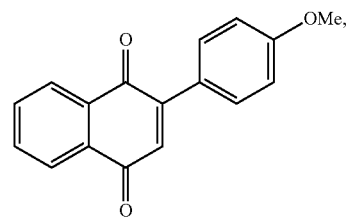  1t
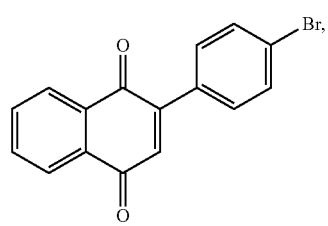  1u
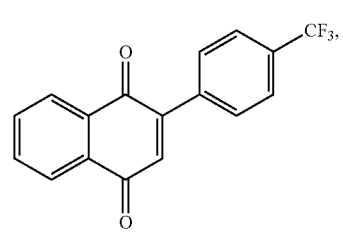  1v
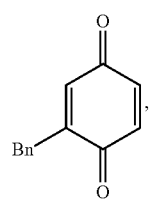  3b
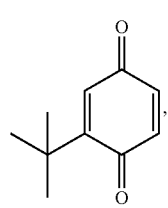  3c
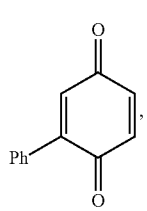  3d
-continued
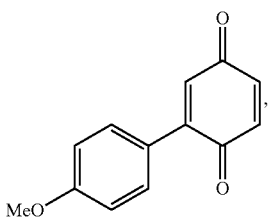  3e
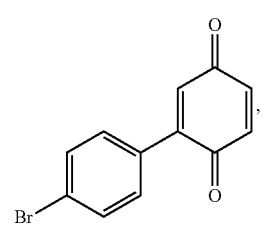  3f
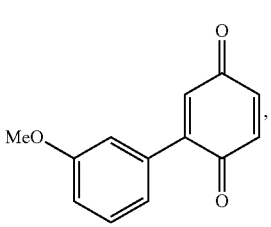  3g
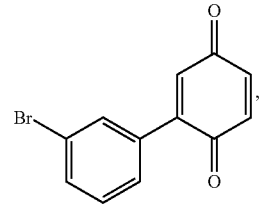  3h
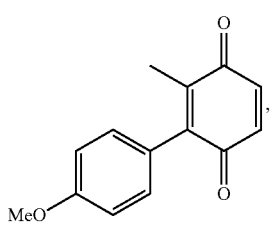  3i
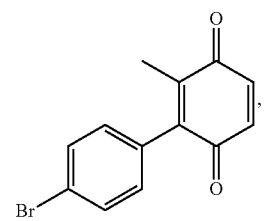  3j
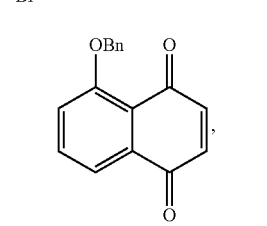  3k -continued

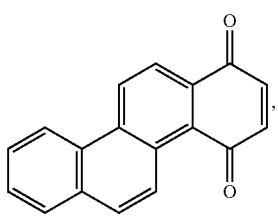
31

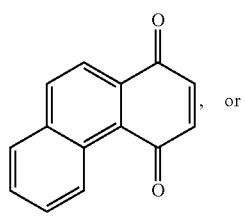
3m

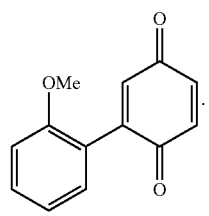
3n

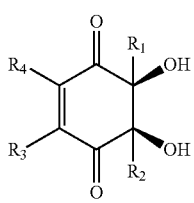

14. The method of claim 1, wherein the cis-diol has a structure of:

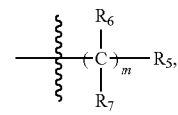

Formula V wherein:
(a) $R_1$-$R_4$ are independently a hydrogen, a substituted or unsubstituted alkyl, a substituted or unsubstituted alkenyl, a substituted or unsubstituted alkynyl, a substituted or unsubstituted aryl, a substituted or unsubstituted polyaryl, a substituted or unsubstituted heteroaryl, a substituted or unsubstituted heteropolyaryl, a substituted or unsubstituted cyclic group, a substituted or unsubstituted heterocyclic, a substituted or unsubstituted aralkyl, a halide, a hydroxyl, an alkoxyl, an amino, an amido, an aminocarbonyl, a carbonyl, a nitrile, or a thiol, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group; and
(b) the substituents, when present, are independently a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, an oxo, a silyl, a sulfinyl, a sulfonyl, a sulfonic acid, a phosphonium, a phosphanyl, a phosphoryl, a phosphonyl, or a thiol, or a combination thereof.

15. The method of claim 14, wherein $R_1$-$R_4$ are independently a hydrogen, a substituted or unsubstituted $C_1$-$C_{10}$ alkyl, a substituted or unsubstituted aryl, a substituted or unsubstituted heteroaryl, a substituted or unsubstituted cyclic group, a substituted or unsubstituted heterocyclic group, an alkoxyl, or

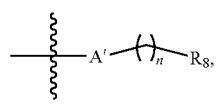

$R_5$ is a substituted or unsubstituted aryl, a substituted or unsubstituted heteroaryl, a substituted or unsubstituted polyaryl, a substituted or unsubstituted heteropolyaryl, a substituted or unsubstituted cyclic group, or a substituted or unsubstituted heterocyclic group, $R_6$ and $R_7$ are independently a hydrogen or a substituted or unsubstituted alkyl, and m is an integer from 1 to 10, or two neighboring R groups together with the carbon atoms to which they are attached form a substituted or unsubstituted aryl or a substituted or unsubstituted polyaryl.

16. The method of claim 14, wherein $R_1$-$R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

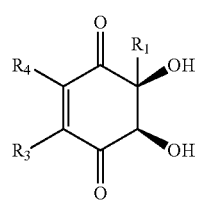

A' is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or two neighboring R groups together with the carbon atoms to which they are attached form a substituted or unsubstituted aryl or a substituted or unsubstituted polyaryl.

17. The method of claim 14, wherein the cis-diol has a structure of:

Formula VII wherein $R_1$, $R_3$, and $R_4$ are independently a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

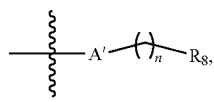

$A'$ is a single bond or an oxygen, $R_8$ is a substituted or unsubstituted phenyl, a substituted or unsubstituted cycloalkyl, or a substituted or unsubstituted heterocycloalkyl, and n is an integer from 1 to 8, or $R_3$ and $R_4$ together with the carbon atoms to which they are attached form a substituted or unsubstituted aryl or a substituted or unsubstituted polyaryl.

18. The method of claim 14, wherein the cis-diol has a structure of:

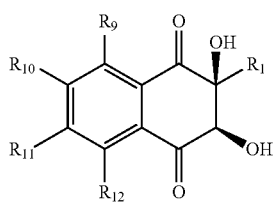

Formula VIII wherein:
(a) $R_1$ is a hydrogen, an unsubstituted $C_1$-$C_6$ alkyl, a substituted or unsubstituted phenyl, a substituted or unsubstituted cycloalkyl, a substituted or unsubstituted cycloalkenyl, a substituted or unsubstituted heterocycloalkyl, a $C_1$-$C_6$ haloalkyl, or

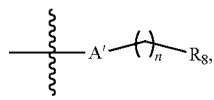

$A'$ is a single bond or an oxygen, $R_8$ is a substituted or unsubstituted phenyl, a substituted or unsubstituted cycloalkyl, or a substituted or unsubstituted heterocycloalkyl, and n is an integer from 1 to 8; and (b) $R_9$-$R_{12}$ are independently a hydrogen, a substituted or unsubstituted alkyl, a substituted or unsubstituted alkenyl, a substituted or unsubstituted alkynyl, a substituted or unsubstituted cyclic group, a substituted or unsubstituted heterocyclic group, a substituted or unsubstituted aryl, a substituted or unsubstituted heteroaryl, a substituted or unsubstituted polyaryl, a substituted or unsubstituted polyheteroaryl, a substituted or unsubstituted aralkyl, a carbonyl, a halide, a hydroxyl, a phenoxy, an aroxy, an alkylthio, a phenylthio, an arylthio, a cyano, an isocyano, an alkoxyl, a nitro, a carboxyl, an amino, an amido, or a sulfhydryl, or two neighboring R groups together with the carbon atoms to which they are attached form a substituted or unsubstituted aryl, a substituted or unsubstituted polyaryl, a substituted or unsubstituted heteroaryl, a substituted or unsubstituted heteropolyaryl, a substituted or unsubstituted cyclic group, or a substituted or unsubstituted heterocyclic group.

19. The method of claim 18, wherein $R_9$-$R_{12}$ are independently a hydrogen, a halide, a hydroxyl, an aroxy, an alkoxyl, or $R_{11}$ and $R_{12}$ together with the carbon atoms to which they are attached form a substituted or unsubstituted cycloalkenyl, a substituted or unsubstituted polycycloalkenyl, a substituted or unsubstituted aryl or a substituted or unsubstituted polyaryl.

20. The method of claim 14, wherein the cis-diol has a structure of:

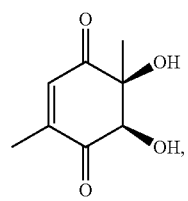

2a

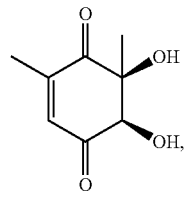

2b

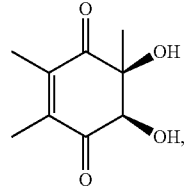

2c

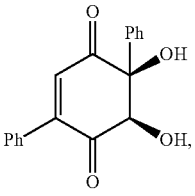

2d

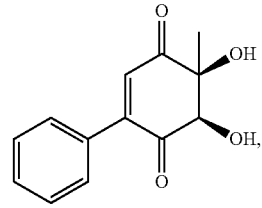

2e

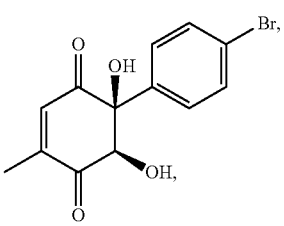

2f

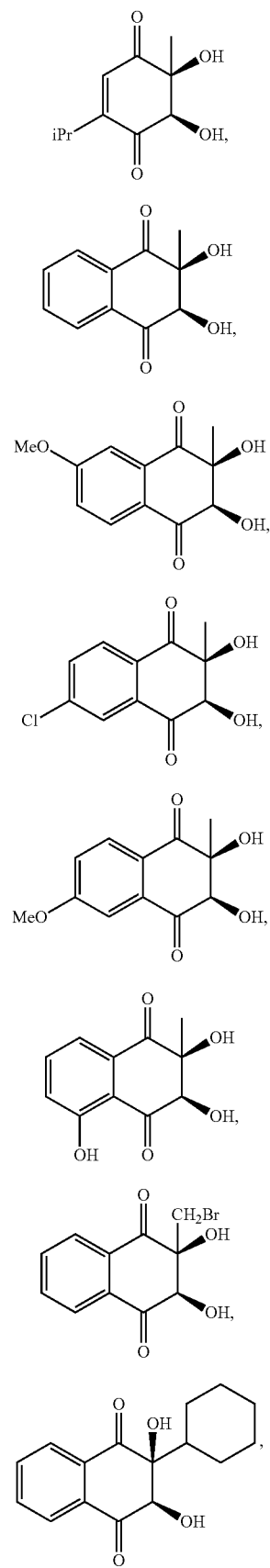
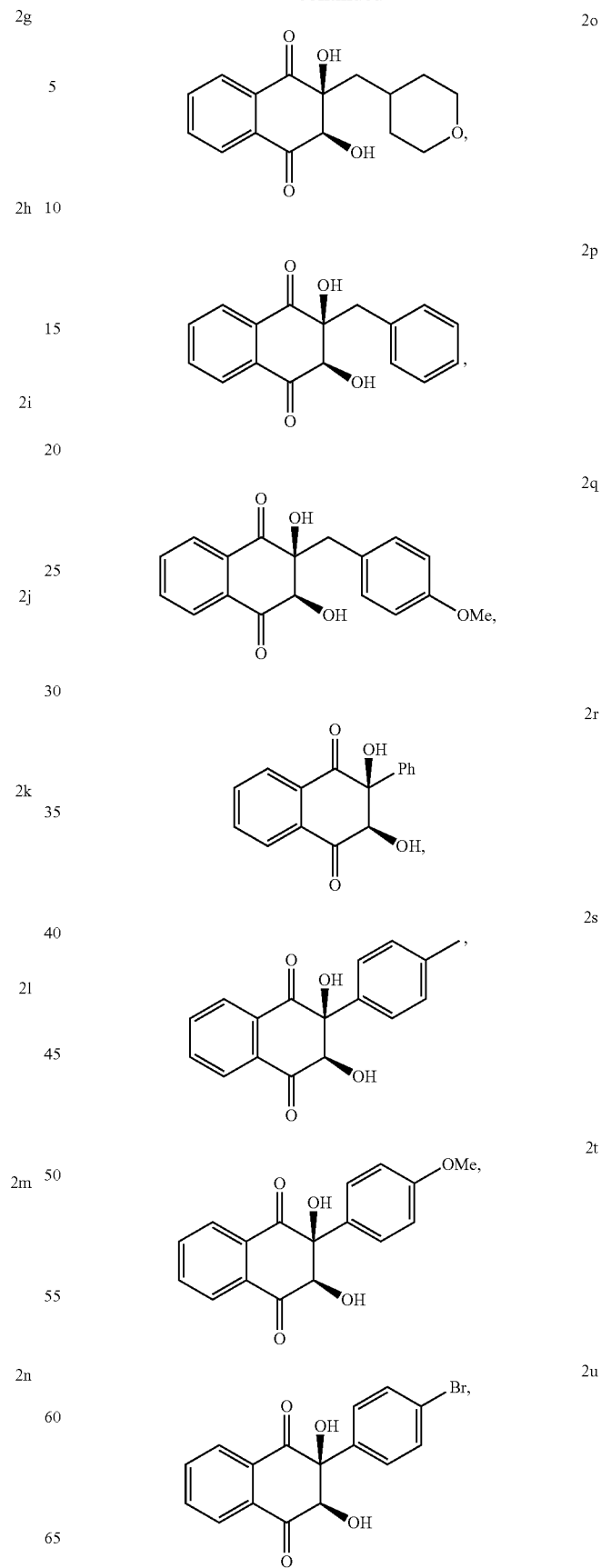

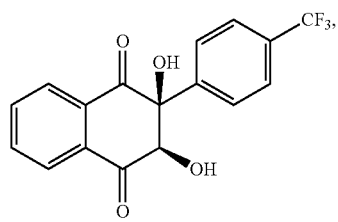 2v
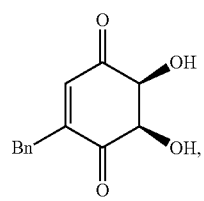 4b
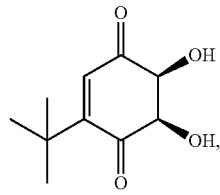 4c
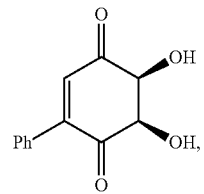 4d
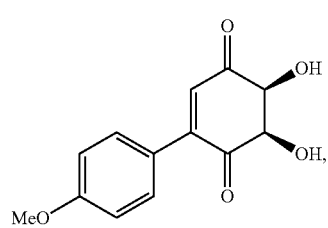 4e
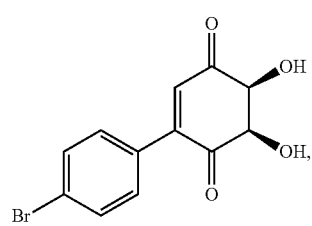 4f
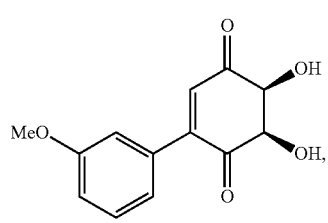 4g
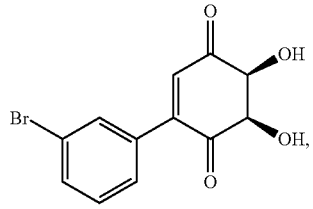 4h
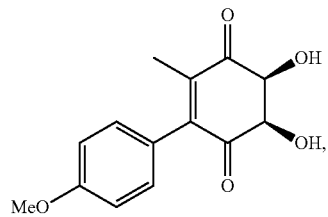 4i
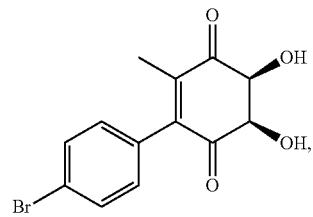 4j
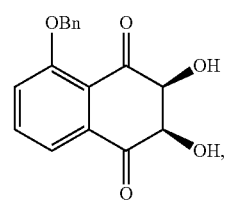 4k
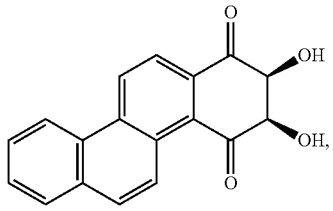 4l
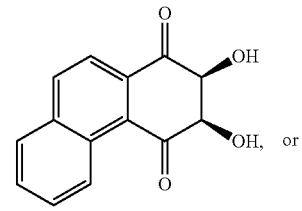 4m, or
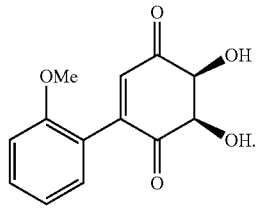 4n 21. The method of claim 1,
(a) wherein the total amount of the one or more iron-based catalyst(s) in the reaction mixture is up to 10 mol %;
(b) wherein the solvent is an alcohol or acetonitrile, or a combination thereof;
(c) wherein the reaction mixture is maintained at room temperature for a period of time in a range from about 20 minutes to about 3 hours; or
(d) a combination thereof.

22. The method of claim 1 further comprising adding one or more additive(s) into the reaction mixture prior to and/or during step (i), stirring the reaction mixture prior to and/or during step (i), and/or purifying the product subsequent to step (i).

23. The method of claim 1,
(a) wherein the cis-diol has a yield of at least 30%;
(b) wherein the cis-diol has a yield that is at least 4-times higher than the yield of the same cis-diol(s) formed from the same reaction, using the same amount or a higher amount of $OsO_4$ or AD-mix-α/β compared to the total amount of the iron-based catalyst;
(c) wherein the cis-diol has an enantiomeric excess that is at least 3-times higher than the enantiomeric excess of the same cis-diol formed from the same reaction, using the same loading or a higher loading of $OsO_4$ or AD-mix-a/p compared to the total amount of the iron-based catalyst; or
(e) a combination thereof.

24. The method of claim 1, wherein the catalyst has a structure of:

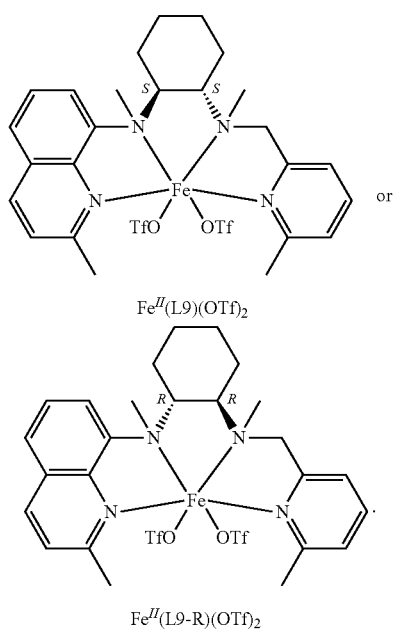

25. The method of claim 1, wherein $R_{24}$ and $R_{24}'$ are methyl.
26. The method of claim 1, wherein $R_{18}$ and $R_{18}'$ are independently an unsubstituted $C_1$-$C_6$ alkyl.
27. The method of claim 1, wherein $R_{25}$ and $R_{25}'$ are independently a triflate or chloride.
28. The method of claim 1, wherein when present, the substituents are independently an unsubstituted alkyl.

* * * * *